(12) United States Patent
Rouwendal et al.

(10) Patent No.: US 8,829,276 B2
(45) Date of Patent: Sep. 9, 2014

(54) MAMMALIAN-TYPE GLYCOSYLATION IN PLANTS BY EXPRESSION OF NON-MAMMALIAN GLYCOSYLTRANSFERASES

(75) Inventors: Gerard Johan Adolph Rouwendal, Heteren (NL); Dionisius Elisabeth Antonius Florack, Wageningen (NL); Hendrik Jan Bosch, Wageningen (NL)

(73) Assignee: Stichting Dienst Landbouwkundig Onderzoek, Wageningen (NL)

( * ) Notice: Subject to any disclaimer, the term of this patent is extended or adjusted under 35 U.S.C. 154(b) by 747 days.

(21) Appl. No.: 12/596,063

(22) PCT Filed: Apr. 17, 2008

(86) PCT No.: PCT/IB2008/000944
§ 371 (c)(1),
(2), (4) Date: Oct. 15, 2009

(87) PCT Pub. No.: WO2008/125972
PCT Pub. Date: Oct. 23, 2008

(65) Prior Publication Data
US 2011/0067146 A1 Mar. 17, 2011
US 2012/0036596 A9 Feb. 9, 2012
US 2012/0210466 A9 Aug. 16, 2012

(30) Foreign Application Priority Data
Apr. 17, 2007 (EP) .................... 07106337

(51) Int. Cl.
C12N 15/82 (2006.01)
A01H 5/00 (2006.01)
C12N 9/10 (2006.01)
C12P 21/00 (2006.01)

(52) U.S. Cl.
CPC .......... *C12N 15/8257* (2013.01); *C12N 9/1051* (2013.01); *C12N 15/8245* (2013.01); *C12P 21/005* (2013.01); *C07K 2319/00* (2013.01); *C12N 15/8246* (2013.01)
USPC ........... 800/288; 800/295; 800/298; 435/468; 435/419

(58) Field of Classification Search
None
See application file for complete search history.

(56) References Cited

U.S. PATENT DOCUMENTS

| | | | |
|---|---|---|---|
| 4,956,282 A | 9/1990 | Goodman et al. | |
| 5,202,422 A | 4/1993 | Hiatt et al. | |
| 5,294,593 A * | 3/1994 | Khan ........................... | 504/100 |
| 5,639,947 A | 6/1997 | Hiatt et al. | |
| 5,874,271 A | 2/1999 | Nishikawa et al. | |
| 5,879,912 A | 3/1999 | Roth | |
| 5,939,288 A | 8/1999 | Thornburg | |
| 5,955,282 A * | 9/1999 | Hillman et al. .............. | 435/6.16 |
| 5,959,177 A | 9/1999 | Hein et al. | |
| 6,046,040 A | 4/2000 | Nishiguchi et al. | |
| 6,054,304 A | 4/2000 | Taniguchi et al. | |
| 6,331,418 B1 | 12/2001 | Roth | |
| 6,344,600 B1 | 2/2002 | Merot et al. | |
| 6,388,068 B1 | 5/2002 | Satoh et al. | |
| 6,602,684 B1 | 8/2003 | Umana et al. | |
| 6,653,459 B1 | 11/2003 | Von Schaewen et al. | |
| 6,998,267 B1 | 2/2006 | Seki et al. | |
| 7,388,081 B2 | 6/2008 | Seki et al. | |
| 7,601,891 B2 | 10/2009 | Bakker et al. | |
| 7,781,647 B2 | 8/2010 | Bakker et al. | |
| 7,897,842 B2 | 3/2011 | Bakker et al. | |
| 8,058,508 B2 | 11/2011 | Bakker et al. | |
| 8,106,169 B2 | 1/2012 | Briggs et al. | |
| 8,193,415 B2 | 6/2012 | Bakker et al. | |
| 8,241,909 B2 | 8/2012 | Seki et al. | |
| 2001/0055584 A1 | 12/2001 | McKenzie et al. | |
| 2002/0019342 A1 | 2/2002 | Bayer | |
| 2002/0174453 A1 | 11/2002 | Danielle et al. | |
| 2004/0072290 A1 | 4/2004 | Umana et al. | |
| 2004/0181827 A1 | 9/2004 | Schaewen et al. | |
| 2004/0214273 A1 | 10/2004 | Fujiyama et al. | |
| 2005/0143564 A1 | 6/2005 | Seki et al. | |
| 2005/0144670 A1 | 6/2005 | Fujiyama et al. | |
| 2005/0223430 A1 | 10/2005 | Bakker et al. | |
| 2006/0253928 A1 | 11/2006 | Bakker et al. | |
| 2007/0089201 A1 | 4/2007 | Briggs et al. | |
| 2007/0214519 A1 | 9/2007 | Fujiyama et al. | |
| 2008/0003680 A1 | 1/2008 | Bakker et al. | |
| 2008/0034456 A1 | 2/2008 | Fujiyama et al. | |
| 2008/0124798 A1 | 5/2008 | Seki et al. | |

(Continued)

FOREIGN PATENT DOCUMENTS

| | | |
|---|---|---|
| AU | 1681300 | 6/2000 |
| DE | 19754622 | 6/1999 |

(Continued)

OTHER PUBLICATIONS

Shaper, J. H. Beta-1,4-galactosyltransferase (1996) Swiss-Prot Accession Q92074; one page.*
Palacpac et al. Stable expression of human beta1,4-galactosyltransferase in plant cells modifies N-linked glycosylation patterns. (1999) PNAS; vol. 96; pp. 4692-4697.*
Shaper, J. H. (1996) GenBank Accession U19890.*
Huether et al. Glyco-engineering of moss lacking plant-specific sugar residues. (2005) Plant Biology; vol. 7; pp. 292-299.*
Ramasamy et al. UDP-Gal:betaBlcNAc beta 1,4-galactosyltransferase 1, membrane-bound form [*Homo sapiens*]. (2005) GenBank Accession NP_001488; pp. 1-5.*

(Continued)

*Primary Examiner* — Cathy Kingdon Worley
(74) *Attorney, Agent, or Firm* — Wolf, Greenfield & Sacks, P.C.

(57) ABSTRACT

The present invention relates to non-mammalian β-1,4-galactosyltransferases that can be used in their wild-type or in modified forms. The invention further relates to transformed plants and plant cells expressing non-mammalian β-1,4-galactosyltransferase and methods to produce glycoproteins with altered and preferably mammalian-type glycosylation. The invention additionally provides nucleic acid molecules and expression vectors of non-mammalian β-1,4-galactosyltransferases.

23 Claims, 5 Drawing Sheets

(56) References Cited

U.S. PATENT DOCUMENTS

| | | | |
|---|---|---|---|
| 2010/0122365 A1 | 5/2010 | Bakker et al. | |
| 2011/0030108 A1 | 2/2011 | Bakker et al. | |
| 2011/0070649 A1 | 3/2011 | Seki et al. | |
| 2012/0010155 A1 | 1/2012 | Bakker et al. | |
| 2012/0011600 A1 | 1/2012 | Bakker et al. | |
| 2012/0060239 A1 | 3/2012 | Fujiyama et al. | |
| 2012/0237972 A1 | 9/2012 | Bakker et al. | |

FOREIGN PATENT DOCUMENTS

| | | |
|---|---|---|
| EP | 0 351 313 A2 | 1/1990 |
| EP | 0 550 756 A1 | 7/1993 |
| EP | 0 737 745 A1 | 10/1996 |
| EP | 0 816 503 A1 | 7/1998 |
| EP | 1 243 647 | 9/2002 |
| JP | 2000-245470 | 9/2000 |
| JP | 2000-287692 | 10/2000 |
| WO | WO 87/00865 | 2/1987 |
| WO | WO 92/18537 | 10/1992 |
| WO | WO 94/12646 | 6/1994 |
| WO | WO 95/02683 | 1/1995 |
| WO | WO 95/21248 | 8/1995 |
| WO | WO 97/04122 | 2/1997 |
| WO | WO 98/31826 | 7/1998 |
| WO | WO 98/31828 | 7/1998 |
| WO | WO 99/09187 | 2/1999 |
| WO | WO 99/24584 | 5/1999 |
| WO | WO 99/29879 | 6/1999 |
| WO | WO 99/38987 | 8/1999 |
| WO | WO 99/38990 | 8/1999 |
| WO | WO 99/51185 | 10/1999 |
| WO | WO 00/28792 | 5/2000 |
| WO | WO 00/29603 | 5/2000 |
| WO | WO 00/34490 | 6/2000 |
| WO | WO 00/49153 | 8/2000 |
| WO | WO 00/52136 | 9/2000 |
| WO | WO 01/29241 | 4/2001 |
| WO | WO 01/29242 | 4/2001 |
| WO | WO 01/31044 | 5/2001 |
| WO | WO 01/31045 | 5/2001 |
| WO | WO 01/49821 | 7/2001 |
| WO | WO 01/49831 | 7/2001 |
| WO | WO 01/62912 | 8/2001 |
| WO | WO 01/64901 | 9/2001 |
| WO | WO 01/81591 | 11/2001 |
| WO | WO 01/82912 | 11/2001 |
| WO | WO 02/00879 | 1/2002 |
| WO | WO 02/057468 | 7/2002 |
| WO | WO 02/007067 | 9/2002 |
| WO | WO 03/001187 | 2/2003 |
| WO | WO 03/007661 | 9/2003 |
| WO | WO 03/007861 | 9/2003 |
| WO | WO 03/007863 | 9/2003 |
| WO | WO 2004/005083 | 6/2004 |

OTHER PUBLICATIONS

Weinstein et al. Primary structure of B-galactoside a2,6-sialyltransferase. (1987) JBC; vol. 262; pp. 17735-17743.*

Chrispeels, M., Glycobiology of Plant Cells, Essentials of Glycobiology, Ch. 20; Varki et al., 1st ed. (1999) Cold Spring Harbor Laboratory Press, NY.

Terashima et al., "Effect of Osmotic Pressure on Human α1-Antitrypsin Production by Plant Cell Culture," Biochemical Engineering Journal 4 (1999) 31-36.

Genbank Submission; NIH/NCBI, Accession No. AJ277603. Bakker et al. Apr. 28, 2000.

Genbank Submission; Accession No. Q92074. Shaper J.H. Nov. 1, 1996.

Genbank Submission; Accession No. U19890. Shaper J. H. Aug. 3, 1996.

Genbank Submission; Accession No. BC124813. Aug. 5, 2006.

Genbank Submission; Accession No. Q08B99. Strausberg et al. Oct. 31, 2006.

Aoki et al. Golgi retention of a trans-Golgi membrane protein, galactosyl-transferase, requires cysteine and histidine residues within the membrane-anchoring domain. (1992) Cell Biology 89, 4319-4323.

Asano et al., Growth retardation and early death of beta-1,4-galactosyltransferase knockout mice with augmented proliferation and abnormal differentiation of epithelial cells. EMBO J. Apr. 15, 1997;16(8):1850-7.

Bailey et al. Metabolic engineering of N-linked glycoform synthesis systems in Chinese hamster ovary (CHO) cells (1997) Animal Cell Technology, pp. 489-494.

Bakker et al., Galactose-extended glycans of antibodies produced by transgenic plants. Proc Natl Acad Sci U S A. Feb. 27, 2001;98(5):2899-904.

Bakker et al., An Arabidopsis thaliana Cdna complements the N-acetylglucosaminyltransferase I deficiency of CHO Lec1 cells. Biochem Biophys Res Commun. Aug. 11, 1999;261(3):829-32.

Borisjuk et al., Production of Recombinant Proteins in Plant Root Exudates. Nat. Biotechnology 17(5): 466-469 (1999).

Boyd et al. The effect of the removal of sialic acid, galactose and total carbohydrate on the functional activity of Campath-1H (1995) Mol Imm. 32, 1311-8.

Cabanes-Macheteau et al., N-Glycosylation of a mouse IgG expressed in transgenic tobacco plants. Glycobiology. Apr. 1999;9(4):365-72.

Choi et al., Use of combinatorial genetic libraries to humanize N-linked glycosylation in the yeast Pichia pastoris. Proc Natl Acad Sci U S A. Apr. 29, 2003;100(9):5022-7. Epub Apr. 17, 2003.

Chrispeels and Faye, The production of recombinant glycoproteins with defined non-immunogenic glycans. In: Transgenic plants: a production system for industrial and pharmaceutical proteins. John Wiley Pub, UK. 1996:99-113.

Colley "Golgi localization of glycosyltransferases: more questions than answers" (1997) Glycobiology 7(1):1-13.

Cousin et al. "Human variant sex hormone-binding globulin (SHBG) with an additional carbohydrate chain has a reduced clearance rate in rabbit." (1998) J of Clin. Endocrin. and Metab. 83: 245-240.

De Vries et al. Isolation of total and polysomal RNA from plant tissues. (1991) Plant Mol. Biology B6/1-13.

Dieryck et al. Human Haemoglobin from transgenic tobacco (1997) Nature 386, 29-30.

Dinter and Berger, The regulation of cell- and tissue-specific expression of glycans by glycosyltransferases. Adv Exp Med Biol. 1995;376:53-82.

Elbers et al., Influence of growth conditions and developmental stage on N-glycan heterogeneity of transgenic immunoglobulin G and endogenous proteins in tobacco leaves. Plant Physiol. Jul. 2001;126(3):1314-22.

Essl et al., The N-terminal 77 amino acids from tobacco N-acetylglucosaminyltransferase I are sufficient to retain a reporter protein in the Golgi apparatus of Nicotiana benthamiana cells. FEBS Lett. Jun. 18, 1999;453(1-2):169-73.

Faye et al Affinity purification of antibodies specific for Asn-linked glycans containing alpha 1—> 3 fucose or beta—> 2 xylose. (1993) Anal Biochem 209, 104-8.

Fischer and Evans, Molecular farming of pharmaceutical proteins. Transgenic Research. 2000;9:279-299.

Fischer et al. Molecular farming of recombinant antibodies in plants. (1999) Biol. Chem. 380:825-839.

Fitchette Laine et al. N-glycans harboring the Lewis a epitope are expressed at the surface of plant cells. (1997) Plan J 12, 1411-7.

Florack et al. Expression of giant silkmoth cecropin B genes in tobacco. (1995) Transgenic Research 4, 132-141.

Fuchs et al., Purification and characterization of microbially expressed neomycin phosphotransferase II (NPTII) protein and its equivalence to the plant expressed protein. Biotechnology (N Y). Dec. 1993;11(13):1537-42.

Fujiyama et al., In vivo conversion of a glycan to human compatible type by transformed tobacco cells. Biochem Biophys Res Commun. Nov. 30, 2001;289(2):553-7.

Gasser and Fraley, Genetically Engineering Plants for Crop Improvement. Science. Jun. 16, 1989;244(4910):1293-1299.

(56) References Cited

OTHER PUBLICATIONS

Gleeson "Targeting of proteins to the Golgi apparatus" (1998) Histochem Cell Biol. 109: 517-532.

Gomez and Chrispeels, Complementation of an *Arabidopsis thaliana* mutant that lacks complex asparagine-linked glycans with the human cDNA encoding N-acetylglucosaminyltransferase I. Proc Natl Acad Sci U S A. Mar. 1, 1994;91(5):1829-33.

Grabenhorst and Conradt, The cytoplasmic, transmembrane, and stem regions of glycosyltransferases specify their in vivo functional sublocalization and stability in the Golgi. J Biol Chem. Dec. 17, 1999;274(51):36107-16.

Hamilton et al., Production of complex human glycoproteins in yeast. Science. Aug. 29, 2003;301(5637):1244-6.

Handa et al., The alpha 1→3 fucosylation at the penultimate GlcNAc catalyzed by fucosyltransferase VII is blocked by internally fucosylated residue in sialosyl long-chain poly-LacNAc: enzymatic basis for expression of physiological E-selectin epitope. Biochem Biophys Res Commun. Feb. 4, 1998;243(1):199-204.

Herman and Horvitz, Three proteins involved in *Caenorhabditis elegans* vulval invagination are similar to components of a glycosylation pathway. Proc Natl Acad Sci U S A. Feb. 2, 1999;96(3):974-9.

Hein et al., Evaluation of immunoglobulins from plant cells. Biotechnol Prog. Sep.-Oct. 1991;7(5):455-61.

Hess et al., Transformation experiments by pipetting *Agrobacterium* into the spikelets of wheat (*Triticum aestivum* L.). Plant Science 1990;72:233-44.

Hiei et al., Efficient transformation of rice (*Oryza sativa* L.) mediated by Agrobacterium and sequence analysis of the boundaries of the T-DNA. Plant J. Aug. 1994;6(2):271-82.

Hiei et al., Transformation of rice mediated by *Agrobacterium tumefaciens*. Plant Mol Biol. Sep. 1997;35(1-2):205-18.

Hollister et al. Stable expression of mammalian β1,4-galactosyltransferase extends the N-glycosylation pathway in insect cells. (1998) Glycobiology 8(5): 473-480.

Hollister et al., Engineering the protein N-glycosylation pathway in insect cells for production of biantennary, complex N-glycans. Biochemistry. Dec. 17, 2002;41(50):15093-104.

Horsch et al. A simple and general method for transferring genes into plants. (1985) Science 227, 1229-1231.

Ihara et al., cDNA cloning, expression, and chromosomal localization of human N-acetylglucosaminyltransferase III (GnT-III). J Biochem (Tokyo). Jun. 1993;113(6):692-8.

Ihara et al "Ectopic Expression of N-acetylglucosaminyltransferase III in transgenic hepatocytes disrupts apolipoprotein B secretion and induces aberrant cellular morphology with lipid storage." Proc Natl Acad Sci USA 1998 95:2526-2530.

Ioffe and Stanley, Mice lacking N-acetylglucosaminyltransferase I activity die at mid-gestation, revealing an essential role for complex or hybrid N-linked carbohydrates. Proc Natl Acad Sci U S A. Jan. 18, 1994;91(2):728-32.

Ishida et al., High efficiency transformation of maize (*Zea mays* L.) mediated by *Agrobacterium tumefaciens*. Nat Biotechnol. Jun. 1996;14(6):745-50.

Jähne et al., Genetic engineering of ceral crop plants: a review. Euphyica. Kluwer Academic Publishers. 1995:85:35-44.

James et al., Production and characterization of biologically active human GM-CSF secreted by genetically modified plant cells. Protein Expr Purif. Jun. 2000;19(1):131-8.

Jarvis and Finn Modifying the insect cell N-glycosylation pathway with immediate early baculovirus expression vectors. (1996) Nat Biotechnol 14, 1288-92.

Jenkins et al., Getting the glycosylation right: implications for the biotechnology industry. Nat Biotechnol. Aug. 1996;14(8):975-81.

Johnson and Chrispeels Substrate specificities of N-acetylglucosaminyl-, fucosyl-, and xylosyltransferases that modify glycoproteins in the Golgi apparatus of bean cotyledons. (1987) Plant Physiology 84, 1301-1308.

Kang et al. "Salt tolerance of *Arabidopsis thaliana* requires maturation of N-glycosylated proteins in the Golgi apparatus." PNAS 2008 105(15):5933-5938.

Kawar et al., Insect cells encode a class II alpha-mannosidase with unique properties. J Biol Chem. May 11, 2001;276(19):16335-40. Epub Feb. 9, 2001.

Kieliszewski et al., Tandem mass spectrometry and structural elucidation of glycopeptides from a hydroxyproline-rich plant cell wall glycoprotein indicate that contiguous hydroxyproline residues are the major sites of hydroxyproline O-arabinosylation. J Biol Chem. Feb. 10, 1995;270(6):2541-9.

Kihlberg et al. "Glysocylated peptide hormones: pharmacological properties and conformation studies of analogues of [1-Desamino,8-D-arginine]vasopressin." J. Med. Chem.; 38:161-169, (1995).

Kitagawa et al. Molecular cloning and expression of glucuronyltransferase I involved in the biosynthesis of the glycosaminoglycan-protein linkage region of proteoglycans. (1998) JBC 273:6615-6618.

Kleene et al., Expression of soluble active human beta 1,4 galactosyltransferase in *Saccharomyces cerevisiae*. Biochem Biophys Res Commun. May 30, 1994;201(1):160-7.

Krezdorn et al "Human beta 1,4 galactosyltransferase and alpha 2,6 sialyltransferase expressed in *Saccharomyces cerevisiae* are retained as active enzymes in the endoplasmic reticulum" Eur J Biochem. Mar. 15, 1994;220(3):809-17.

Ku et al., High-level expression of maize phosphoenolpyruvate carboxylase in transgenic rice plants. Nat Biotechnol. Jan. 1999;17(1):76-80.

Leiter et al., Purification, cDNA cloning, and expression of GDP-L-Fuc:Asn-linked GlcNAc alpha1,3-fucosyltransferase from mung beans. J Biol Chem. Jul. 30, 1999;274(31):21830-9.

Lerouge et al., Control of the N-Glycosylation of therapeutic glycoproteins produced in transgenic plants: a new challenge for glycobiologists. Molecular Farming of Plants and Animals for Human and Veterinary Medicine. Chapter 4, 2002;73-109.

Lerouge et al., N-glycoprotein biosynthesis in plants: recent developments and future trends. Plant Mol Biol. Sep. 1998;38(1-2):31-48.

Lerouge et al., N-glycosylation of recombinant pharmaceutical glycoproteins produced in transgenic plants: towards an humanisation of plant N-glycans. Curr Pharm Biotechnol. Dec. 2000;1(4):347-54.

Li et al., Cloning, expression and characterization of a cDNA (6A8) encoding a novel human alpha-mannosidase. Eur J Biochem. Dec. 2000;267(24):7176-83. Erratum in: Eur J Biochem Nov. 2001;268(21):5653.

Ma et al. Generation and assembly of secretory antibodies in plants (1995) Science 268, 716-9.

Madson et al., Altered xyloglucans of *Arabidopsis thaliana* mutants bind normally to cellulose in vivo and in vitro. Poster from Plant Biology(Rockville) Jul. 27, 2001 Abstract #527.

Magnuson et al., Secretion of biologically active human interleukin-2 and interleukin-4 from genetically modified tobacco cells in suspension culture. Protein Expr Purif. Jun. 1998;13(1):45-52.

Magnuson et al., Enhanced recovery of a secreted mammalian protein from suspension culture of genetically modified tobacco cells. Protein Expr Purif. Mar. 1996;7(2):220-8.

Maras et al., In vitro conversion of the carbohydrate moiety of fungal glycoproteins to mammalian-type oligosaccharides—evidence for N-acetylglucosaminyltransferase-I-accepting glycans from *Trichoderma reesei*. Eur J Biochem. Nov. 1, 1997;249(3):701-7.

Masri et al., Identification of the full-length coding sequence for human galactosyltransferase (beta-N-acetylglucosaminide: beta 1,4-galactosyltransferase). Biochem Biophys Res Commun. Dec. 15, 1988;157(2):657-63.

Matsumoto et al. Characterization of a human glycoprotein (erythropoietin) produced in cultured tobacco cells. Mol. Biol. 27, 1163-1172, (1995).

Melo et al. Identification of the human Lewis(a) carbohydrate motif in a secretory peroxidase from a plant cell suspension culture (*Vaccinium myrtillus* L.) FEBS Lett 415, 186-91, (1997).

Milland et al. "The cytoplasmic tail of α1,2-fucosyltransferase contains a sequence for golgi localization" (2001) J. Biol. Chem. 276(15):12012-12018.

Miyake et al., Purification of human erythropoietin. J Biol Chem. Aug. 10, 1977;252(15):5558-64.

(56) References Cited

OTHER PUBLICATIONS

Miyoshi et al., The alpha1-6-fucosyltransferase gene and its biological significance. Biochim Biophys Acta. Dec. 6, 1999;1473(1):9-20.
Mokrzycki-Issartel et al., A transient tobacco expression system coupled to MALDI-TOF-MS allows validation of the impact of differential targeting on structure and activity of a recombinant therapeutic glycoprotein produced in plants. FEBS Lett. Sep. 25, 2003;552(2-3):170-6.
Munro "Localization of proteins to the Golgi apparatus" (1998) Trends Cell Biol. 8(1): 11-15.
Naigai et al., "N-Glycosylation is Requisite for the Enzyme Activity and Golgi Retention of N-Acetylglucosaminyltransferase III." Glycobiology 7(6):769-776 (1997).
Palacpac et al., Stable expression of human beta1,4-galactosyltransferase in plant cells modifies N-linked glycosylation patterns. Proc Natl Acad Sci U S A. Apr. 13, 1999;96(8):4692-7.
Palacpac et al., Structures of N-linked oligosaccharides of glycoproteins from tobacco BY2 suspension cultured cells. Biosci Biotechnol Biochem. Jan. 1999;63(1):35-9.
Philipp et al., "Characterization of nuclear membranes and endoplasmic reticulum isolated from plant tissue" JCB 1976 68:11-29.
Rayon et al. Characterization of N-Glycans from *Arabidopsis*. Application to a Fucose-Deficient Mutant (1999) Plant Physiology 119, 725-733.
Rayon et al., N-Glycosylation of phytohemagglutinin expressed in bean cotyledons or in transgenic tobacco plants. Plant Physiol Biochem. 1996;34:273-81.
Rishi et al. "Molecular Farming in Plants: A Current Perspective." (2001) J. Plant Biochem. & Biotech 10: 1-12.
Rothman, Protein sorting by selective retention in the endoplasmic reticulum and Golgi stack. Cell. Aug. 14, 1987;50(4):521-2.
Saint-Jore-Dupas et al. "Plant N-Glycan Processing Enzymes Employ Different Targeting Mechanisms for Their Spatial Arrangement along the Secretory Pathway." The Plant Cell 2006 18:3182-3200.
Saito et al. Integration and expression of a rabbit liver cytochrome P-450 gene in transgenic *Nicotiana tabacum* (1991) Proc. Natl. Acad. Sci. 88, 7041-7045.
Sakai et al., Fatty Acid acylation of apoE by human monocyte/marophages and helptocytes. Apr. 1998; 417. Abstract.
Sakai et al., Human glycosyltransferase expression and intracellular/intercellular glycoprotein sugar chain structure in cultured tobacco BY2 cells. Corrected title: Expression of human β 1,4-galatosyltransferase in tobacco BY2 cells modifies glycosylation patterns of intracellular and extracellular glycoproteins. IC Biotech. Osaka, Nara Institute. Mar. 1998. Abstract.
Sakai et al., "Expression of Human β1,4-Galactosyltransferase in Tobacco BY2 Cells Modifies Glycosylation Patterns of Intracellular and Extracellular Glycoproteins," Translation of Abstract from the Ann. Meeting of Japan Society for Bioscience, Biotechnology, and Agrochemistry, Published Mar. 1998. (Additional translation of Sakai et al previously submitted).
Schachter, The 'yellow brick road' to branched complex N-glycans. Glycobiology. Nov. 1991;1(5):453-61.
Scherer et al., "Action and Inhibition of Endogenous Phospholipases during Isolation of Plant Membranes" Plant Physiol 1978 62:933-37.
Schindler et al. Arabinogalactan proteins in maize coleoptiles: developmental relationship to cell death during xylem differentiation but not to extention growth. (1995) Plant JU 7, 25-36.
Seveno et al., Glycoprotein Sialylation in plants? Nat Biotechnol. Nov. 2004;22(11):1351-2.
Shah et al., Sialylated endogenous glycoconjugates in plant cells. Nat Biotechnol. Dec. 2003;21(12):1470-1. Epub Nov. 9, 2003.
Shaper et al. Bovine galactosyltransferase: identification of a clone by direct immunological screening of a CDNA expression library. (1986) Proc Natl Acad Sci USA 83, 1573-7.
Smant et al. Potato root diffusate-induced secretion of soluble, basic proteins originating from the subventral esophageal glands of potato cyst nematodes (1997) Phytopathology 87, 839-845.

Stanley and Ioffe Glycosyltransferase mutants: key to new insights in glycobiology (1995) Faseb j 9, 1436-44.
Stanley et al. CHO cells provide access to novel N-glycans and developmentally regulated glycosyltransferases. (1996) Glycobiology 6, 695-9.
Staudacher E, "Functional purification and characterization of GDP-fucose: beta-N-acetylglucosamine (Fuc to Asn linked GlcNAc) alpha 1,3-fucosyltransferase from mung beans." Glycoconj J. Dec. 1995;12(6):780-6.
Staudacher E, "Strict order of (Fuc to Asn-linked GlcNAc) fucosyltransferases forming core-difucosylated structures." Glycoconj J. Apr. 1998;15(4):355-60.
Strasser et al., Molecular cloning of CDNA encoding N-acetylglucosaminyltransferase II from *Arabidopsis thaliana*. Glycoconj J. Dec. 1999;16(12):787-91.
Strasser et al., "Molecular cloning and functional expression of beta 1,2-sylosyltransferase cDNA from *Arabidopsis thaliana*[1]" Febs Letters, Elsevier, Amsterdam, NL, Apr. 2000 472(1): 105-108.
Strasser et al. "Molecular basis of N-acetylglucosaminyltransferase I deficiency in *Arabidopsis thaliana* plants lacking complex N-glycans." Biochem J. 2005 387:385-391.
Sturm et al. "Subcellular localization of glycosidases and glycosyltransferases involved in the processing of N-linked oligosaccharides" (1987) Plant Physiol. 85(3):741-745.
Takahashi et al., Xylose-containing common structural unit in N-linked oligosaccharides of laccase from sycamore cells. Biochemistry. 1986;25(2):388-95.
Tang et al., The transmembrane domain of N-glucosaminyltransferase I contains a Golgi retention signal. J Biol Chem. May 15, 1992;267(14):10122-6.
Taniguchi et al., A glycomic approach to the identification and characterization of glycoprotein function in cells transfected with glycosyltransferase genes. Proteomics. Feb. 2001;(2):239-47.
Terayama et al., Cloning and functional expression of a novel glucuronyltransferase involved in the biosynthesis of the carbohydrate epitope HNK-1. Proc Natl Acad Sci U S A. Jun. 10, 1997;94(12):6093-8.
Terayama et al., "Purification and Characterization of a Glucuronyltransferase Involved in the Biosynthesis of the HNK-1 Epitope on Glycoproteins from Rat Brain." The Journal of Biological Chemistry 273(46):30295-30300 (1998).
Thanavala et al. Immunogenicity of transgenetic plant derived hepatitis B surface antigen. (1995) Proc Natl Acad Sci USA 92, 3358-3361.
Umana et al. Engineered glycoforms of an antineuroblastoma IgG1 with optimize antibody-dependent cellular cytotoxic activity. (1999) Nature Biotech. 17: 176-180.
Van Engelen et al., Coordinate expression of antibody subunit genes yields high levels of functional antibodies in roots of transgenic tobacco. Plant Mol Biol. Dec. 1994;26(6):1701-10.
Van Engelen et al. pBINPLUS: an improved plant transformation vector based on pBIN19. (1995) Transgenetic Res 4, 288-90.
Van Ree et al., Beta(1,2)-xylose and alpha(1,3)-fucose residues have a strong contribution in IgE binding to plant glycoallergens. J Biol Chem. Apr. 14, 2000;275(15):11451-8.
Vitale and Chrispeels, Transient N-acetylglucosamine in the biosynthesis of phytohemagglutinin: attachment in the Golgi apparatus and removal in protein bodies. J Cell Biol. Jul. 1984;99(1 pt 1):133-40.
Voelker et al., In vitro mutated phytohemagglutinin genes expressed in tobacco seeds: role of glycans in protein targeting and stability. Plant Cell. Jan. 1989;1(1):95-104.
Von Schaewen et al. Isolation of a mutant *Arabidopsis* plant that lacks N-acetyl glucosaminyl transferase I and is unable to synthesize Golgi-modified complex N-linked glycans. (1993) Plant Physiol 102, 1109-18.
Warner, T.G., Metabolic engineering glycosylation: biotechnology's challenge to the glycobiologist in the next millenium; Carbohydrates in chemistry and biology, part II vol. 4. editors Earnst et al. (2000) Wiley-VCH. 1042-64.
Wee et al., Targeting of active sialyltransferase to the plant Golgi apparatus. Plant Cell. Oct. 1998;10(10):1759-68.

(56) References Cited

OTHER PUBLICATIONS

Whitelam GC., The production of recombinant proteins in plants. (1995) J. Sci. Food Agric., 68:1-9.

Wiebauer et al., Nuclear pre-mRNA processing in plants: distinct modes of 3' splice-site selection in plants and animals (1988) MCB: vol. 8 pp. 2042-2051.

Wilson et al., Core alpha1,3-fucose is a key part of the epitope recognized by antibodies reacting against plant N-linked oligosaccharides and is present in a wide variety of plant extracts. Glycobiology. Jul. 1998;8(7):651-61.

Wilson et al., Cloning and expression of cDNAs encoding alpha1,3-fucosyltransferase homologues from *Arabidopsis thaliana*. Biochim Biophys Acta. Jul. 2, 2001;1527(1-2):88-96.

Wright and Morrison, Effect of glycosylation on antibody function: implications for genetic engineering. Trends Biotechnol. Jan. 1997;15(1):26-32.

Yamaguchi et al., Genomic structure and promoter analysis of the human alpha1, 6-fucosyltransferase gene (FUT8). Glycobiology. Jun. 2000;10(6):637-43.

Yamaguchi and Fukuda Golgi retention mechanism of β-1,4-Galactosyltransferase (1995) J of Biol Chemistry 270(20): 12170-12176.

Yin et al., [Obtaining transgenic rice plants and their progenies using *Agrobacterium tumefaciens*] Yi Chuan Xue Bao. Dec. 1998;25(6):517-24. Chinese.

Yoshida et al., Molecular biology and application of plant peroxidase genes. Appl Microbiol Biotechnol. Feb. 2003;60(6):665-70. Epub Dec. 18, 2002.

Yoshida et al., Expression of β1 4 galactosyltransferase in tobacco culture cell. Program for Congress of the Society for Bioscience and Bioengineering of Japan. Sep. 15, 1995;1-5.

Yosida et al., "Challenge for production of human-compatible glycoprotein therapeutics in yeast", Bioscience and Industry, vol. 54, pp. 420-422 (1996).

Zhang et al., Transformation of tobacco using human β-1 , 4 galactosyltransferase gene and regeneration of transgenic plants. Annual reports of IC Biotech. 1995;18:241-7.

Zhang et al., *Agrobacterium*-mediated transformation of elite indica and japonica rice cultivars. Mol Biotechnol. Dec. 1997;8(3):223-31.

Zhang and Wang, Quantitative analysis and process monitoring of site-specific glycosylation microheterogeneity in recombinant human interferon-gamma from Chinese hamster ovary cell culture by hydrophilic interaction chromatography. J Chromatogr B Biomed Sci Appl. Aug. 7, 1998;712(1-2):73-82.

Zhu et al., Beta 1,4 N-acetylgalactosaminyltransferase (GM2/GD2/GA2 synthase) forms homodimers in the endoplasmic reticulum: a strategy to test for dimerization of Golgi membrane proteins. Glycobiology. Oct. 1997;7(7):987-96.

Genbank Submission; Accession No. ADL27179. Hillman J. L. et al. May 20, 2004.

Davies et al., Expression of GnTIII in a recombinant anti-CD20 CHO production cell line: Expression of antibodies with altered glycoforms leads to an increase in ADCC through higher affinity for FC gamma RIII. Biotechnol Bioeng. Aug. 20, 2001;74(4):288-94.

Fast et al., The role of the carbohydrate chains of Gal beta-1,4-GlcNAc alpha 2,6-sialyltransferase for enzyme activity. Biochim Biophys Acta. Oct. 6, 1993;1202(2):325-30.

Fitchette-Laine et al., Chapter 19: Analysis of *N*- and *O*-Glycosylation of plant proteins. Methods in Biotechnology, vol. 3. Cunningham and Porter, eds. Humana Press. 1998: 271-90.

Giddings, Transgenic plants as protein factories. Curr Opin Biotechnol. Oct. 2001;12(5):450-4.

Ikeda et al., Kinetic basis for the donor nucleotide-sugar specificity of beta1, 4-N-acetylglucosaminyltransferase III. J Biochem. Oct. 2000;128(4):609-19.

Rayon et al., The protein N-glycosylation in plants. Journal Exper Botany. Sep. 1998. 49(326):1463-72.

Sakai et al., Human glycosyltransferase expression and intracellular/intercellular glycoprotein sugar chain structure in cultured tobacco BY2 cells. IC Biotech. Osaska, Nara Institute. Mar. 1998. Abstract. Original with English Abstract.

Udagama-Randeniya et al., Electrophoretic analysis of coniferyl alcohol oxidase and related laccases. Electrophoresis. Aug.-Sep. 1994;15(8-9):1072-7.

* cited by examiner

Figure 1

Mammalian extension — TM

```
human      -MRLREPLLSGSAAMPGASLQRACRLLVAVCALHLGVTLVYYLAGRDLSRLPQLVGVSTP            (SEQ ID No. 30)
mouse      -MRFREQFLGGSAAMPGATLQRACRLLVAVCALHLGVTLVYYLSGRDLSRLPQLVGVSST            (SEQ ID No. 31)
bovine     -MKFREPLLGGSAAMPGASLQRACRLLVAVCALHLGVTLVYYLAGRDLRRLPQLVGVHPP            (SEQ ID No. 32)
chicken    ---MKEP------ALPGTSLQRACRLLVAFCALHLSATLLYYLAGSSLTPP-----------          (SEQ ID No. 33)
zebrafish  ----MPDSTGNFSL-----LQRTCSLVVLLCFLHIFVTVIYYMRNSDS--RPAFA------          (SEQ ID No. 34)
frog       MKEPQLPVSNLTAALPGASLQKACKFVVVFCSLHFCVVLIYYLSGADFGILQFFR------          (SEQ ID No. 35)
                  :   **::  :** . * **::  . ..*-*: .  .

human      LQGGSNSAAAIGQSSGELRTGARPPPLGASSQRP----GGDSSPVVDSGPGPASNLT              (SEQ ID No. 36)
mouse      LQGGTNGAAASKQPPGEQRPRGARPPPLGVSPKPRP---GLDSSPGAASGPGLKSNLS              (SEQ ID No. 37)
bovine     LQGSSHGAAAIGQPSGELRLRGVAPPPLQNSSKPRSRAPSNLDAYSHPGPGPGPGSNLT             (SEQ ID No. 38)
chicken    ---RSPEPPPRRPPPANLSLPPSRPPPPP---AARPRP---------GP-VSAQPR                (SEQ ID No. 39)
zebrafish  ---QNQQQRPTIHRKLAEQRGTTEDSRPAANASSNGQ------------------                 (SEQ ID No. 40)
frog       ---QNQQSQLAYKQNYTISNATMRAISTKGRTKEPKE------------------                 (SEQ ID No. 41)
                                                   ::               .
```

Figure 5

```
Full-length alignment between two sequences
>>NM_001017730                                                    (214 aa)
 s-w opt: 505  Z-score: 616.1  bits: 121.8 E(): 1.7e-32
Smith-Waterman score: 505; 43.564% identity (49.162% ungapped) in 202 aa overlap
(1-183:1-198)

10        20        30        40        50
DGAL   MPDSTGNFSLLQRTCSLVVLLCFLHIFVTVIYMRNSD------SRPAFAQNQQQRPTI
       : :::.:: :   : ::::: ::::.:.:::  ::          :::: .:.:   :
NM_001 MSESVGFFT----KACVVLVLLCGLHLIVALIFYLSESPLAKFRNYRHISFISDMVNSQT-
                10        20        30        40        50

60        70        80        90       100
DGAL   HRKLAEQRGTTED----SRPAANAS------SNGQELQICPEEPPRLVGPLRVEFSDPI
       :.:::::::: ::    :::: :         ::::::::::::::::::::::::::
NM_001 HGELGQADNETLDVAVYKRIYNNETVIIGDVEKPAEVLESCPETSPLLVGQLRVEFSTPV
                60        70        80        90       100       110

110       120       130       140       150       160
DGAL   TLEMVRTENSVLQEGGRFRPPDCIARQKVAMIIPFRNRDEHLKFWLYYLHPILQRQQLDY
       ::::::::::::::::::::::::::::::::::::::::::::::::::::::::::::
NM_001 DFNLVRQGNKHLTMGGRYTPTKCVALQKVAMITPYRNREEHLKYWLYYLHPILKRQLLDY
                120       130       140       150       160       170

170       180       190       200       210       220
DGAL   GVYVINQDGEDTFNRA-KLLNIGYAEALKEYDYDCFVFSDVDLIPMDDRNIYKCYNQPRH  (SEQ ID No. 42)
       :.:::::::::::::: :::::::::::::::::::::::::::::::::::::::::::
NM_001 GIYIEQDGENTPNKTLKSLTICILGLSLRISVTLMVE                         (SEQ ID No. 43)
                180       190       200       210
```

MAMMALIAN-TYPE GLYCOSYLATION IN PLANTS BY EXPRESSION OF NON-MAMMALIAN GLYCOSYLTRANSFERASES

RELATED APPLICATIONS

This application is a national stage filing under 35 U.S.C. 371 of International Application PCT/IB2008/000944 designating the United States of America, and filed Apr. 17, 2008. This application claims the benefit of European Application 07106337.4 filed Apr. 17, 2007. The entire teachings of the referenced applications are incorporated herein by reference in their entirety. International Application PCT/IB2008/000944 was published under PCT Article 21(2) in English.

FIELD OF THE INVENTION

The invention relates to the field of glycoprotein processing in transgenic plants, in particular in such plants as used for the production of recombinant biopharmaceutical proteins.

BACKGROUND OF THE INVENTION

Recombinant protein production constitutes an important application of transgenic plants. In addition to the yield and the favorable cost of the field production of recombinant proteins, transgenic plants present certain advantages over other production systems, such as bacteria, yeasts, and animal cells. Indeed, they are devoid of agents infectious to humans, and can accumulate the proteins of interest in storage tissues, such as seeds or tubers. This facilitates their handling, their transportation and their storage at ambient temperature, while affording the possibility of subsequent extraction. Moreover, the transgenic plant, or some of its parts, can be utilized as vector of medicaments or of vaccines.

Although the advantages of plants as factories of proteinaceous substances are explained mostly in the light of biopharmaceuticals, plants are also useful for production of other proteins, e.g., industrial enzymes and the like, because of their capability of glycosylation leading e. g. to higher stability. Today, the utilization of plants for the production of heterologous glycoproteins for therapeutic and other use is investigated in soy, tobacco, potato, rice and rapeseed, and the glycoproteins produced therein include monoclonal antibodies, hormones, vaccine antigens, enzymes and blood proteins. Some of these proteins have already proven their efficacy in humans.

A drawback of glycoprotein production in plants relates to the glycosylation pattern of the glycoproteins produced in plants. Like other heterologous expression systems, plants exhibit a different glycosylation profile compared to mammals. In contrast to bacteria, having no N-linked glycans, and yeast, having only N-linked glycans of the high mannose type, plants are able to produce proteins with N-linked glycans of the complex type. However, plant glycoproteins have complex N-linked glycans containing β1,2-xylose and α1,3-fucose residues not found in mammals. Moreover, plant glycoproteins lack the characteristic galactose-containing complex N-glycans found in mammals.

In short, analyses of glycoproteins from plants have indicated that, although similarities exist, several steps in the glycosylation pathways of plants and mammals are different, particularly in the synthesis of complex glycans. The complex glycans of plants are generally much smaller and contain beta-1,2 xylose or alpha-1,3 fucose residues attached to the $Man_3(GlcNAc)_2$ core. Such residues on glycoprotein are known to be immunogenic, which causes problems for certain applications of recombinant proteins carrying these sugars.

SUMMARY OF THE INVENTION

Although some plant-based systems for the production of glycoproteins have been proposed or are in use there is a need for improved plant-based systems for the production of humanized proteins. In certain embodiments, the present invention provides such improved plant-based systems.

Previously proposed plant-based systems, such as described in e.g., WO01/31045 (the entire contents is incorporated herein), utilized mammalian β1,4-galactosyltransferase for the production of humanized proteins.

It has now been discovered that certain, previously uncharacterized glycosyltransferases such as those derived from the non-mammals, chicken and zebrafish, exhibiting homology to certain parts of characterized mammalian β1,4-galactosyltransferases, show unexpected improvements over previous methods in the production of humanized proteins.

According to one aspect of the invention, methods of producing a transgenic plant or a transgenic plant cell which is capable of adding galactose residues in β-1,4-linkage to N-linked glycans are provided. These methods comprise inserting a nucleic acid molecule coding for a non-mammalian β-1,4-galactosyltransferase into a plant or a plant cell and selecting a transgenic plant or transgenic plant cell that has taken up the nucleic acid molecule coding for a non-mammalian β-1,4-galactosyltransferase and expresses the nucleic acid molecule, thereby producing a transgenic plant or transgenic plant cell capable of adding galactose residues in β-1,4-linkage to N-linked glycans. In certain embodiments the non-mammalian β-1,4-galactosyltransferase comprises either chicken or zebrafish β-1,4-galactosyltransferase 1. In certain embodiments the chicken β-1,4-galactosyltransferase 1 comprises SEQ ID NO:2, whereas the zebrafish β-1,4-galactosyltransferase 1 comprises SEQ ID NO:14. In some embodiments the non-mammalian β-1,4-galactosyltransferase of chicken or zebrafish is extended with an amino acid sequence capable of directing localisation of the non-mammalian β-1,4-galactosyltransferase in the Golgi apparatus. In some embodiments the non-mammalian β-1,4-galactosyltransferase is extended at the N-terminus with an amino acid sequence corresponding to the N-terminal amino acid sequence of a mammalian β1,4-galactosyltransferase 1. In certain embodiments the N-terminal amino acid sequence comprises at least the sequence [K/R]-X-[K/R] in the first 10 N-terminal amino acids, wherein [K/R] represents either a lysine or arginine residue and X can be any amino acid. In certain embodiments the N-terminal amino acid sequence is MRLREPLLSGSAA (SEQ ID NO: 21). In some embodiments the cytoplasmic-transmembrane-stem region (CTS) of the non-mammalian β-1,4-galactosyltransferase is replaced by the CTS of another Golgi-localized protein. In some embodiments the CTS is derived from a mammalian or plant Golgi-localized protein. In some embodiments the CTS is derived from a mammalian sialyltransferase. In certain embodiments the CTS is derived from rat α2,6-sialyltransferase.

According to another aspect of the invention, methods of producing a heterologous glycoprotein comprising one or more galactosylated N-linked glycans are provided, comprising inserting into a plant or plant cell a nucleic acid molecule encoding a non-mammalian β-1,4-galactosyltransferase and a nucleic acid molecule encoding a heterologous glycoprotein, thereby producing a transgenic plant or a transgenic plant cell and maintaining the transgenic plant or a transgenic plant cell under conditions appropriate for expression of the nucleic acid molecules, whereby a heterologous glycoprotein comprising one or more galactosylated N-linked glycans is produced.

In certain embodiments the non-mammalian β-1,4-galactosyltransferase is chicken β-1,4-galactosyltransferase or zebrafish β-1,4-galactosyltransferase. In certain embodiments the chicken β-1,4-galactosyltransferase or zebrafish β-1,4-galactosyltransferase is extended at the N-terminus with an amino acid sequence corresponding to the N-terminal amino acid sequence of a mammalian β-1,4-galactosyltransferase 1. In certain embodiments the CTS of the chicken β-1,4-galactosyltransferase or zebrafish β-1,4-galactosyltransferase is replaced by the CTS of another Golgi-localized protein.

In certain embodiments the methods further comprise at least partially isolating the heterologous glycoprotein from the transgenic plant or transgenic plant cell. In certain embodiments the glycoprotein comprises one or more galactose residues on one or more N-glycans. In some embodiments the N-glycans of the glycoprotein are essentially devoid of xylose, fucose, or both xylose and fucose residues. In certain embodiments the nucleic acid molecule encoding a heterologous glycoprotein encodes a hormone; a cytokine, a vaccine; an adhesion molecule, or an antibody or a functional fragment thereof.

In certain embodiments the plant or plant cell additionally comprises a nucleic acid molecule encoding at least one selection marker expressible in a plant or a plant cell. In certain embodiments the plant or plant cell is or is derived from *Nicotiana* ssp. In some embodiments the nucleic acid molecules are inserted via microinjection, PEG transformation, *Agrobacterium* mediated transformation, electroporation, ballistic particle bombardment, direct gene transfer, liposome fusion, in planta transformation, calcium phosphate precipitation, agrofiltration, or virus infection.

According to another aspect of the invention, methods of producing a transgenic plant or a transgenic plant cell which is capable of adding galactose residues in β-1,4-linkage to N-linked glycans are provided, wherein the non-mammalian β-1,4-galactosyltransferase is encoded by a nucleic acid that is at least 85% identical to chicken β1,4-galactosyltransferase nucleic acid sequence (SEQ ID NO:1) or zebrafish β1,4-galactosyltransferase nucleic acid sequence (SEQ ID NO:13). In other embodiments the nucleic acid is at least 90%, 95%, or 98% identical to either chicken β1,4-galactosyltransferase nucleic acid sequence (SEQ ID NO:1) or zebrafish β1,4-galactosyltransferase nucleic acid sequence (SEQ ID NO:13).

According to another aspect of the invention, methods of producing a transgenic plant or a transgenic plant cell which is capable of adding galactose residues in β-1,4-linkage to N-linked glycans are provided, wherein the amino acid sequence of the enzymatically active domain of the non-mammalian β-1,4-galactosyltransferase is at least 85% identical to that of the chicken β1,4-galactosyltransferase amino acid sequence (SEQ ID NO:2) or to that of zebrafish β1,4-galactosyltransferase amino acid sequence (SEQ ID NO:14). In other embodiments the amino acid sequence of the enzymatically active domain of the non-mammalian β-1,4-galactosyltransferase is at least 90%, 95%, or 98% identical to that of the chicken β1,4-galactosyltransferase amino acid sequence (SEQ ID NO:2) or to that of zebrafish β1,4-galactosyltransferase amino acid sequence (SEQ ID NO:14). In certain embodiments the amino acid sequence of non-mammalian β-1,4-galactosyltransferase additionally comprises a mammalian extension. In some embodiments the mammalian extension is MRLREPLLSGSAA (SEQ ID NO:21). In certain embodiments the CTS of non-mammalian β-1,4-galactosyltransferase is replaced with the CTS from another Golgi-localized protein, and wherein the amino acid sequence of the enzymatically active domain of non-mammalian β-1,4-galactosyltransferase is at least 85% identical to chicken β1,4-galactosyltransferase amino acid sequence (SEQ ID NO:2) or to that of zebrafish β1,4-galactosyltransferase amino acid sequence (SEQ ID NO:14). In other embodiments the amino acid sequence of the enzymatically active domain of non-mammalian β-1,4-galactosyltransferase is at least 90%, 95%, or 98% identical to chicken β1,4-galactosyltransferase amino acid sequence (SEQ ID NO:2) or to that of zebrafish β1,4-galactosyltransferase amino acid sequence (SEQ ID NO:14). In certain embodiments the CTS from another Golgi-localized protein is the CTS from rat α2,6-sialyltransferase.

According to yet another aspect of the invention, methods of producing a transgenic plant or a transgenic plant cell which is capable of adding galactose residues in β-1,4-linkage to N-linked glycans are provided, wherein the plant or plant cell produces a glycoprotein comprising hybrid-type N-linked glycans lacking both β1,2-xylose and α1,3-fucose residues. In certain embodiments the amount of hybrid-type N-linked glycans lacking both β1,2-xylose and α1,3-fucose residues produced is twice the amount produced by a plant cell or plant expressing wild-type human β1,4-galactosyltransferase. In other embodiments the amount of hybrid-type N-linked glycans lacking both β1,2-xylose and α1,3-fucose residues produced is five times, ten times, or fifty times the amount produced by a plant cell or plant expressing wild-type human β1,4-galactosyltransferase. In certain embodiments the plant or plant cell produces a glycoprotein comprising bi-antennary N-glycans comprising at least one galactosylated GlcNAc residue. In those embodiments the amount of bi-antennary N-glycans comprising at least one galactosylated GlcNAc residue produced is two times, five times, ten times, or fifty times the amount produced by a plant cell or plant expressing wild-type human β1,4-galactosyltransferase.

According to yet another aspect of the invention, glycoproteins produced according to the methods described herein are provided.

According to another aspect of the invention, plants produced according to the method described herein, or parts of such plants, are provided. In certain embodiments the plant is a part of a plant selected from the group consisting of seeds, embryos, callus tissue, leaves, roots, shoots, pollen, and microspores.

According to another aspect of the invention, plant cells produced according to the methods described herein are provided. In certain embodiments the plant cells are grown in suspension culture. In certain embodiments the plant cells grown in suspension culture are selected from a group consisting of *N. tabacum* BY2, *Daucus carota* and *Arabidopsis thaliana* cell suspension. In certain embodiments the plant cells are part of a moss selected from a group consisting of *Bryophytaea, Physcomitrella patens, Funaria hygrometrica,* and *Ceratodon purpureus.*

According to another aspect of the invention, nucleic acids are provided, encoding a polypeptide comprising the amino acid sequence of chicken β-1,4-galactosyltransferase 1 (SEQ ID NO:2) or zebrafish β-1,4-galactosyltransferase 1 (SEQ ID NO:14) and an extension at the N-terminus thereof, wherein the extension is an amino acid sequence corresponding to the N-terminal amino acid sequence of a mammalian β1,4-galactosyltransferase 1, wherein the N-terminal amino acid sequence comprises at least the sequence [K/R]-X-[K/R] in the first 10 N-terminal amino acids, wherein [K/R] represents either a lysine or arginine residue and X can be any amino acid. In certain embodiments the amino acid sequence is MRLREPLLSGSAA (SEQ ID NO: 21). In certain embodiments the amino acid sequence comprises SEQ ID NO: 8 or SEQ ID NO:15. In certain embodiments the nucleic acid encoding a polypeptide comprising the amino acid sequence of chicken β-1,4-galactosyltransferase 1 (SEQ ID NO:2) or zebrafish β-1,4-galactosyltransferase 1 (SEQ ID NO:14), wherein the CTS of the chicken β-1,4-galactosyltransferase or zebrafish β-1,4-galactosyltransferase is replaced by the CTS of another Golgi-localized protein. In certain embodiments the CTS is derived from a mammalian or plant Golgi-localized protein. In certain embodiments the CTS is derived from a mammalian sialyltransferase. In certain embodiments the CTS is derived from rat α2,6-sialyltransferase. In certain embodiments the amino acid sequence comprises SEQ ID NO: 11 or SEQ ID NO:18.

According to yet another aspect of the invention, nucleic acids are provided, encoding a polypeptide comprising an amino acid sequence of a non-mammalian β-1,4-galactosyltransferase, wherein the amino acid sequence of the enzymatically active domain of the non-mammalian β-1,4-galactosyltransferase is at least 90% identical to that of the chicken β-1,4-galactosyltransferase 1 (SEQ ID NO:2) or zebrafish β-1,4-galactosyltransferase 1 (SEQ ID NO:14) and an extension at the N-terminus thereof, wherein the extension is an amino acid sequence corresponding to the N-terminal amino acid sequence of a mammalian β1,4-galactosyltransferase 1, wherein the N-terminal amino acid sequence comprises at least the sequence [K/R]-X-[K/R] in the first 10 N-terminal amino acids, wherein [K/R] represents either a lysine or arginine residue and X can be any amino acid. In other embodiments the sequence identity is at least 95% or 98%.

According to yet another aspect of the invention, expression vectors comprising nucleic acid molecules described herein are provided. In some embodiments the nucleic acid molecules are linked to regulatory elements sufficient for transcription of the nucleic acid molecule in eukaryotic or prokaryotic cells.

According to another aspect of the invention, host cells are provided comprising nucleic acid molecules described herein which are linked to heterologous regulatory elements sufficient for transcription in plant cells or comprising vectors described herein.

LEGENDS TO THE DRAWINGS

FIG. 1 depicts sequence alignments (Clustal W) of β1,4-galactosyltransferases of various mammalian (human, mouse, bovine) and non-mammalian (chicken, zebrafish, frog) origins. "Mammalian extension" is an amino-terminal region specific to mammals not found in non-mammalian orthologs of β1,4-galactosyltransferase (boxed, solid lines). "TM" marks the transmembrane region (boxed, dashed lines).

FIG. 5 depicts an amino acid sequence comparison of Dgal (SEQ Dgal, SEQ ID NO:14) with putative zebrafish β1,4-GalT1 as published (Machingo et al., *Dev Biol* 297, 471-82, 2006; NM_001017730).

DETAILED DESCRIPTION OF THE INVENTION

Figure 2:
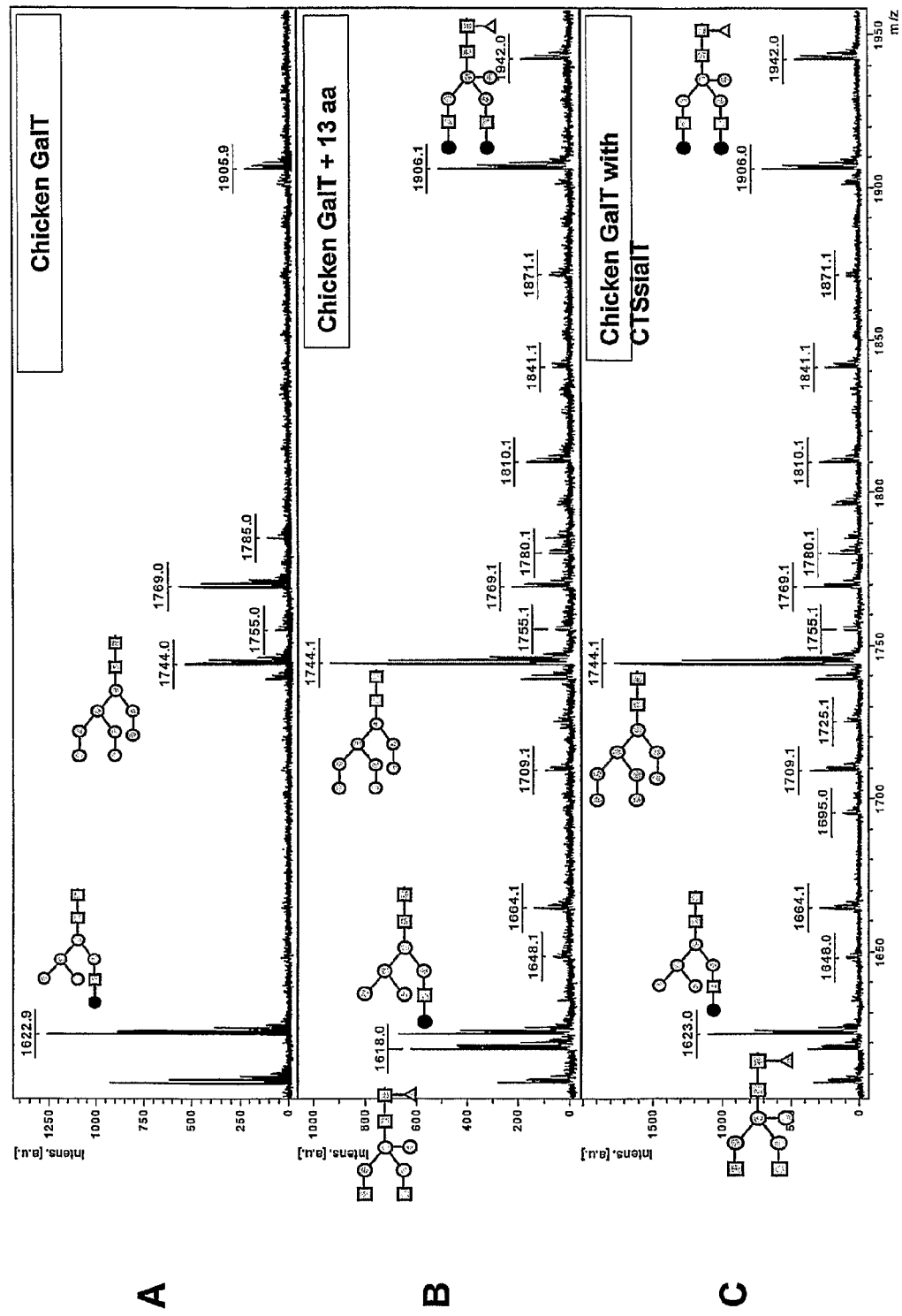
FIG. 2 depicts results from Maldi-TOF analyses of N-glycans purified from transgenic plants expressing the chicken gene. From top to bottom, normal chicken gene (chicken GalT), 13 amino acid N-terminus human GalT-chicken GalT, and SialT-CTS-chicken GalT.

The Golgi apparatus is an organelle where complex glycan formation takes place and is the site of the glycosylation machinery. The key mediators of glycosylation are the glycosyltransferases. One of the best studied Golgi-associated glycosyltransferase is β1,4-galactosyltransferase 1 (GalT). β1,4-galactosyltransferase 1 consists of a cytosolic tail, a transmembrane domain (TMD) and a catalytic domain. Numerous genes of glycosyl transferases of mammals have already been cloned. The ease of transformation of plant systems, allowed researchers to "complement" the Golgi apparatus of plants by glycosyltransferases from mammals in order to "humanize" or "mammalize" the glycans of the glycoproteins they produce.

The use of non-mammalian β1,4-galactosyltransferases (GalT) has hitherto not been reported for the production of mammalized or humanized glycoproteins in plants.

It has now been discovered that certain, previously uncharacterized non-mammalian β1,4-galactosyltransferases, such as those derived from chicken and zebrafish, can be utilized for terminal galactosylation of N-linked glycoproteins in plants, and that these non-mammalian β1,4-galactosyltransferases show unexpected improvements over previous methods in the production of humanized proteins. For example chicken β1,4-galactosyltransferase produces mostly hybrid-type N-linked glycans lacking both β1,2-xylose and α1,3-fucose residues.

It was further found that non-mammalian β1,4-galactosyltransferases from chicken and zebrafish are shorter than mammalian β-1,4-galatosyltransferases and lack an amino-terminal region present in mammalian β1,4-galactosyltransferases. These non-mammalian β-1,4-galatosyltransferases can be extended at the amino-terminus with an amino acid sequence corresponding to the amino-terminus of a mammalian β1,4-galactosyltransferase, the "mammalian extension." These modified versions of the non-mammalian β1,4-galactosyltransferases produce certain N-linked glycans to a higher degree compared to human β1,4-galactosyltransferase. For example, zebrafish GalT having substituted its amino-terminal for the CTS region of rat sialyltransferase, produces mainly biantennary, double galactosylated N-glycans.

The invention, in some embodiments, provides unmodified or modified non-mammalian GalTs from chicken and fish that are used to produce mammalized glycoproteins in plants. Mammalized glycoproteins produced in plants or plant cells expressing such non-mammalian β1,4-galactosyltransferases are also provided in certain embodiments.

Definitions

The term "nucleic acid" as used herein, includes reference to a deoxyribonucleotide or ribonucleotide polymer, i.e., a polynucleotide, in either single- or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids). A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including among other things, simple and complex cells.

"Nucleic acid molecules coding for" or "nucleic acid molecules encoding" as used herein are not limited to individual or separate molecules, for example nucleic acid molecules as separate entities, wherein each entity comprises one nucleic acid molecules, it also encompasses that one or more nucleic acid molecules may be linked in one contiguous sequence, which may be separated by any intervening sequence. The order and orientation of the nucleic acid molecules in one contiguous sequence is not limited to any specific configuration, e.g. the nucleic acid molecules may be linked to the same promoter, or a different promoter, may be mono- or bidirectional, and may be directly adjacent or separated by intervening sequence. Various such configurations are known in the art. Additional nucleic acid molecules may be combined in one contiguous sequence, or may be provided as separate entities. For example, in certain embodiments plants or plant cells are provided comprising nucleic acid molecules comprising a non-mammalian β-1,4-galactosyltransferase, a heterologous glycoprotein and one or more selection markers. These nucleic acid molecules may be provided in the form of one, two, three, or more vectors, as described herein.

The terms "polypeptide," "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The essential nature of such analogues of naturally occurring amino acids is that, when incorporated into a protein, that protein is specifically reactive to antibodies elicited to the same protein but consisting entirely of naturally occurring amino acids. The terms "polypeptide," "peptide" and "protein" are also inclusive of modifications including, but not limited to, glycosylation, lipid attachment, sulfation, gamma-carboxylation of glutamic acid residues, hydroxylation and ADP-ribosylation.

A "coding" or "encoding" sequence is the part of a gene that codes for the amino acid sequence of a protein, or for a functional RNA such as a tRNA or rRNA and specifically refers to the fact that the nucleic acid sequence comprises the information for translation into the specified protein. A nucleic acid encoding a protein may comprise non-translated sequences (e.g., introns) within translated regions of the nucleic acid, or may lack such intervening non-translated sequences (e.g., as in cDNA). The information by which a protein is encoded is specified by the use of codons. Typically, the amino acid sequence is encoded by the nucleic acid using the "universal" genetic code. However, variants of the universal code, such as are present in some plant, animal, and fungal mitochondria, the bacterium *Mycoplasma capricolum*, or the ciliate Macronucleus, may be used when the nucleic acid is expressed therein. When the nucleic acid is prepared or altered synthetically, advantage can be taken of known codon preferences of the intended host where the nucleic acid is to be expressed. For example, although nucleic acid sequences of the present invention may be expressed in both monocotyledonous and dicotyledonous plant species, sequences can be modified to account for the specific codon preferences and GC content preferences of monocotyledons or dicotyledons as these preferences have been shown to differ.

"Expression" refers to the transcription of a gene into structural RNA (rRNA, tRNA) or messenger RNA (mRNA) with subsequent translation into a protein.

The term "non-mammalian" in relation to a protein or nucleic acid refers to such compounds derived from a non-mammal, including, e.g., a non-mammalian vertebrate, such as a bird (e.g., a chicken or duck) or a fish, and a non-mammalian invertebrate. Very suitable sources of non-mammalian β-1,4-galactosyltransferases (and coding sequences) are chicken and fish.

The term "mammalian" in relation to a protein or nucleic acid refers to such compounds derived from a mammal, e.g., a human, a non-human primate, a mouse, pig, cow, goat, cat, rabbit, rat, guinea pig, hamster, horse, monkey, sheep, wallaby, platypus or other non-human mammal.

The term "β-1,4-galactosyltransferase," refers to the glycosyltransferase EC 2.4.1.38 (β-1,4-GalT1) that is required for the biosynthesis of the backbone structure from type 2 chain (Galβ1→4GlcNAc), which appears widely on N-linked glycans, i.e., which enzyme has galactosylating activity on i.a. N-linked glycans. The type 2 chain is particularly important in the synthesis of sialyl lewis x and SSEA-1, which play a role in the immune system and early embryogenesis, respectively. Mammalian β-1,4-galactosyltransferase are provided herein (e.g., from human, mouse, rat), as well as orthologs of β-1,4-galactosyltransferase from non-mammalian species, such as chicken and fish.

The term "sequence identity" as used herein denotes the presence of identity between two or more polynucleotides or between two or more polypeptides. Polynucleotides or polypeptides have "identical" sequences if the sequence of nucleotides or amino acids, respectively, of one polynucleotide or polypeptide is the same when aligned for maximum correspondence to another polynucleotide or polypeptide. Sequence comparison between two or more polynucleotides or polypeptides is generally performed by comparing portions of two sequences over a comparison window to identify and compare local regions of sequence similarity. The comparison window is generally from about 20 to 200 contiguous nucleotides or from about 7 to 70 contiguous amino acids. The "percentage of sequence identity" for polynucleotides or polypeptides, such as 50, 60, 70, 80, 90, 95, 98, 99 or 100 percent sequence identity may be determined by comparing two optimally aligned sequences over a comparison window, wherein the portion of the polynucleotide or polypetide sequence in the comparison window may include additions or deletions (i.e., gaps) as compared to the reference sequence (which does not comprise additions or deletions) for optimal alignment of the two sequences. The percentage is calculated by: (a) determining the number of positions at which the identical nucleic acid base or amino acid residue occurs in both sequences to yield the number of matched positions; (b) dividing the number of matched positions by the total number of positions in the window of comparison; and (c) multiplying the result by 100 to yield the percentage of sequence homology. Optimal alignment of sequences for comparison may be conducted by computerized implementations of known algorithms, or by inspection. Algorithms and software suitable for use in aligning sequences for comparison and calculation of sequence homology or identity will be known to those skilled in the art. Significant examples of such tools are the Pearson and Lipman search based FASTA and BLAST programs, details of these may be found in Altschul et al (1997), Nucleic Acid Res. 25:3389-3402; Altschul et al (1990), J. Mol. Biol. 215: 403-10; Pearson and Lipman (1988), Proc. Natl. Acad. Sci. USA 85:2444-8; Lipman and Pearson (1985), Science 227:1435-41). Other suitable programs include the PILEUP, LINEUP, GAP, BESTFIT and FASTA programs in the GCG® Wisconsin Package® of the University of Wisconsin Genetics Computer Group, Madison, Wis., USA, now offered through Accelrys Inc. Details of the above programs are available on the internet through 'http://www.ncbi.nlm.nih.gov/BLAST' or mirror sites and "http://www.accelrys.com/products/gcg_wisconsin_package." Thus such homology and identity percentages can be ascertained using publicly or commercially available software packages or by computer servers on the internet. By the term "identity" is meant that the stated percentage of the claimed amino acid sequence or nucleic acid sequence is to be found in the reference sequence in the same relative positions when the sequences are optimally aligned, notwithstanding the fact that the sequences may have deletions or additions in certain positions requiring introduction of gaps to allow alignment of the highest percentage of amino acids or bases. Preferably the sequence are aligned by using 10 or less gaps, i.e., the total number of gaps introduced into the two sequences when added together is 10 or less. The length of such gaps is not of particular importance but generally will be no more than 10, and preferably no more than 5 amino acids, or 30 and preferably no more than 15 bases.

The term "degeneracy of the genetic code" refers to the fact that a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations." Every nucleic acid sequence herein that encodes a polypeptide also, by reference to the genetic code, describes every possible silent variation of the nucleic acid.

The term "complementary" in "complementary strand" means that the nucleic acid strand has a sequence of nucleotides which forms a hydrogen-bonded duplex with another sequence of nucleotides according to Watson-Crick base-pairing rules. For example, the complementary base sequence for 5'-AAGGCT-3' is 3'-TTCCGA-5'.

The term "galactosylated N-linked glycan" refers to the common core of an N-linked oligosaccharide unit in glycoproteins that consists of a chitobiose core with at least three mannoses and at least one N-acetylglucosamine residue and that is further extended with at least one galactose residue on a N-acetylglucosamine at the nonreducing end.

The term "antibody" includes reference to antigen binding forms of antibodies (e.g., Fab, F(ab)2). The term "antibody" frequently refers to a polypeptide substantially encoded by an immunoglobulin gene or immunoglobulin genes, or fragments thereof which specifically bind and recognize an analyte (antigen). However, while various antibody fragments can be defined in terms of the digestion of an intact antibody, one of skill will appreciate that such fragments may be synthesized de novo either chemically or by utilizing recombinant DNA methodology. Thus, the term antibody, as used herein, also includes antibody fragments such as single chain Fv, chimeric antibodies (i.e., comprising constant and variable regions from different species), humanized antibodies (i.e., comprising a complementarity determining region (CDR) from a non-human source) and heteroconjugate antibodies (e. g., bispecific antibodies).

The term "antibody heavy or light chain" are used in their art-recognized meaning.

The term "functional fragment" refers to a shortened version of the protein which is a functional variant or functional derivative. A "functional variant" or a "functional derivative" of a protein is a protein the amino acid sequence of which can be derived from the amino acid sequence of the original protein by the substitution, deletion and/or addition of one or more amino acid residues in a way that, in spite of the change in the amino acid sequence, the functional variant retains at least a part of at least one of the biological activities of the original protein that is detectable for a person skilled in the art. A functional variant is generally at least 50% homologous (preferably the amino acid sequence is at least 50% identical), at least 70% homologous or at least 90% homologous to the protein from which it can be derived. A functional variant may also be any functional part of a protein. In certain embodiments, the function is galactosyltransferase activity. In some embodiments the amino acid sequence differs from SEQ ID NO:2 (the protein sequence of chicken galactosyltransferase) or SEQ ID NO:14 (the protein sequence of zebrafish galactosyltransferase) mainly or only by conservative substitutions. In some embodiments the protein comprises an amino acid sequence having 65% or more, 75% or more, 85% or more, 90% or more, or 95% or more, sequence identity with SEQ ID NO:2 or SEQ ID NO: 14 and in certain embodiments 100% identity with those sequences. "Functional" as used herein also includes functional in plants.

The expression "conservative substitutions" as used with respect to amino acids relates to the substitution of a given amino acid by an amino acid having similar biochemical characteristics. Thus, in some embodiments, where an amino acid in the sequence of SEQ ID NO:2 or SEQ ID NO: 14 has a hydrophobic group, a conservative substitution replaces it by another amino acid also having a hydrophobic group; other such biochemical similarities are those where the characteristic group is hydrophilic, cationic, anionic or contains a thiol or thioether. Such substitutions are well known to those of ordinary skill in the art, i.e. see U.S. Pat. No. 5,380,712. Conservative amino acid substitutions may be made, for example within the group of aliphatic non-polar amino acids (Gly, Ala, Pro, Ile, Leu, Val), the group of polar uncharged amino acids (Cys, Ser, Thr, Met, Asn, Gln), the group of polar charged amino acids (Asp, Glu, Lys, Arg) or the group of aromatic amino acids (His, Phe, Tyr, Trp).

The term "selection marker" refers to a polynucleotide sequence encoding a metabolic trait which allows for the separation of transgenic and non-transgenic organisms and may refer to the provision of antibiotic resistance. A selectable marker is for example the aphL1 encoded kanamycin resistance marker, the nptII gene, the gene coding for hygromycin resistance. Other resistance markers are well known in the art. Other selection markers are for instance reporter genes such as chloramphenicol acetyl transferase, β-galactosidase, luciferase and green fluorescence protein. Identification methods for the products of reporter genes include, but are not limited to, enzymatic assays and fluorimetric assays. Reporter genes and assays to detect their products are well known in the art and are described, for example in Current Protocols in Molecular Biology, eds. Ausubel et al., Greene Publishing and Wiley-Interscience: New York (1987) and periodic updates.

As used herein, the term "vector" includes reference to a nucleic acid used in transfection of a host cell and into which can be inserted a polynucleotide. Vectors are often replicons. Expression vectors permit transcription of a nucleic acid inserted therein.

As used herein, the term "operably linked" refers to a functional linkage or juxtaposition wherein the components so described are in a relationship permitting them to function in their intended manner. A control sequence "operably linked" to another control sequence and/or to a coding sequence is ligated in such a way that transcription and/or expression of the coding sequence is achieved under conditions compatible with the control sequence. Generally, operably linked means that the nucleic acid sequences being linked are contiguous and, where necessary to join two protein coding regions, contiguous and in the same reading frame.

By "host cell" is meant a cell which contains a vector and supports the replication and/or expression of the vector. Host cells may be prokaryotic cells such as E. coli, or eukaryotic cells such as plant, yeast, insect, amphibian, or mammalian cells.

As used herein, "heterologous" in reference to a nucleic acid is a nucleic acid that originates from a foreign species, or, if from the same species, is modified from its native form in composition and/or genomic locus by intervention. For example, a promoter operably linked to a heterologous structural gene is from a species different from that from which the structural gene was derived, or, if from the same species, one or both are modified from their original form. A heterologous protein may originate from a foreign species or, if from the same species, is modified from its original form by intervention.

The term "regulatory sequence" or "control sequence" is defined herein to include any component which is necessary or advantageous for expression of a coding sequence. A regulatory sequence may be native or foreign to the coding sequence. Such regulatory sequences include, but are not limited to, a leader, a polyadenylation sequence, a propeptide sequence, a promoter, a signal sequence, and a transcription terminator. Such sequences are well known in the art. At a minimum, the regulatory sequences include a promoter, or certain promoter elements and transcriptional and translational stop signals. The regulatory sequences may be provided with linkers for the purpose of introducing specific restriction sites facilitating ligation of the regulatory sequences with the coding region of the nucleic acid sequence encoding a polypeptide.

The term "promoter" is used herein for its art-recognized meaning to denote a portion of a gene containing DNA sequences that provide for the binding of RNA polymerase and initiation of transcription. Promoter sequences are commonly, but not always, found in the 5' non-coding regions of genes. A "plant promoter" is a promoter capable of initiating transcription in plant cells whether or not its origin is a plant cell. Exemplary plant promoters include, but are not limited to, those that are obtained from plants, plant viruses, and bacteria which comprise genes expressed in plant cells such as Agrobacterium or Rhizobium. Examples of suitable promoters are the 35S promoter of Cauliflauwer mosaic virus and derivatives thereof, the ferredoxin promoter, the nopaline synthase (nos), mannopine synthase (mas) and octopine synthase (ocs) promoters (EP 0 122 791, EP 0 126 546, EP 0 145 338), the ubiquitin promoter (EP 0 342 926), the cassava vein mosaic virus promoter and the chrysanthemum promoter for the short subunit of Rubisco.

The term "transgenic plant or plant cell" includes reference to a plant or plant cell which comprises within its genome a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. Also, it is possible that the heterologous polynucleotide is not or not stably integrated in the genome of the transformed plant. In that case, the gene can be 'transiently' expressed, implying that expression occurs for a given time, after which the introduced polynucleotide is lost from the cell. For the purposes of this invention, a transgenic plant or plant cell also includes plants or plant cells which transiently express the heterologous polypeptide. "Transgenic" is used herein to include any cell, cell line, callus, tissue, plant part or plant, the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

The term "insertion" in the context of introducing a nucleic acid into a cell, means "transfection" or "transformation" or "transduction" and includes reference to the incorporation of a nucleic acid into a eukaryotic or prokaryotic cell where the nucleic acid may be incorporated into the genome of the cell (e.g., chromosome, plasmid, plastid or mitochondrial DNA), converted into an autonomous replicon, or transiently expressed (e.g., transfected mRNA).

As used herein, the term "plant" includes (reference to) whole plants, plant organs (e.g., leaves, stems, roots, etc.), seeds and plant cells and progeny of same. Plant cell(s), as used herein includes, without limitation, seeds, embryos, meristematic regions, callus tissue, leaves, roots, shoots, gametophytes, sporophytes, pollen, and microspores. In some embodiments plant cells are grown in suspension culture. In some embodiments plant cells are capable of regenerating a whole plant. The class of plants which can be used in the methods of the invention is generally as broad as the class of higher plants amenable to transformation techniques, including both monocotyledonous and dicotyledonous plants. As used herein when referring to plants the whole spectrum of plants ranging from algae to trees is intended unless otherwise specified. Preferred plants are Nicotiana ssp., preferably N. tabacum or N. benthamiana.

The term "specifically recognizing", includes reference to a binding reaction between an antibody and a protein having an epitope recognized by the antigen binding site of the antibody. This binding reaction is determinative of the presence of a protein having the recognized epitope amongst the presence of a heterogeneous population of proteins and other biologics. Thus, under designated immunoassay conditions, the specified antibodies bind to an analyte having the recognized epitope to a substantially greater degree (e.g., at least 2-fold over background) than to substantially all analytes lacking the epitope which are present in the sample. Specific binding to an antibody under such conditions may require an antibody that is selected for its specificity for a particular protein. For example, antibodies raised to the polypeptides described herein, e.g., SEQ ID NOS. 2, 4, 7, 9, 11, 14, 16, 18 and 20 can be selected to obtain antibodies specifically recognizing these polypeptides. The proteins or polypeptides used as immunogens can be in native conformation or denatured so as to provide a linear epitope. A variety of immunoassay formats may be used to select antibodies specifically recognizing a particular protein (or other analyte). For example, solid-phase ELISA immunoassays are routinely used to select monoclonal antibodies specifically immunoreactive with a protein. See Harlow and Lane, Antibodies, A Laboratory Manual, Cold Spring Harbor Publications, New York (1988), for a description of immunoassay formats and conditions that can be used to determine selective reactivity.

Nucleic Acid Molecules and Cellular Expression Systems

Although a nucleic acid molecule encoding a polypeptide described herein can be expressed in any cellular expression system, such as plants, yeast, bacteria, non-mammalian and mammalian cellular expression systems, the nucleic acid molecules are preferably expressed in plants or plant cells, which may be grown in suspension.

In some embodiments, the present invention provides plants or plant cells comprising functional proteins providing N-glycan biosynthesis, wherein the protein is a non-mammalian β-1,4-galactosyltransferase, e.g., from chicken or fish origin. In other embodiments, said non-mammalian β-1,4-galactosyltransferases are extended at the N-terminus with an N-terminal extension sequence facilitating localization with respect to the Golgi-apparatus to enable the intended function of the enzyme. The N-terminal extension sequence generally consists of a cytosolic tail comprising a Golgi-localization signal sequence and a transmembrane domain. Such an N-terminal sequence (designated as "CTS") can be derived from a mammalian β-1,4-galactosyltransferase, from a mammalian sialyltransferase or from any other Golgi-localized protein and fused to the catalytic domain of a non-mammalian GalT, e.g., from chicken or fish origin, and expressed in plant cells or plants.

The N-terminal cytoplasmic, transmembrane region (referred to as CTS region herein) of glycosyltransferases determines the localisation of the enzyme in the ER or Golgi membrane. To provide natural or desirable glycosylation, glycosyltransferases can be expressed in plants as they occur in mammals, but can also be expressed as a fusion protein between two, or part of two, different glycosyltransferases. In this case the localisation is determined by one enzyme and the catalytic activity by a second enzyme. As an example, a fusion between the cytoplasmic, transmembrane and stem region of a rat sialyltransferase and the catalytic domain of mammalian galactosyltransferase, such as provided, for example, in SEQ ID NO: 10 and SEQ ID NO: 17, provides an enzyme with galactosyltransferase activity and localisation of the sialyltransferase.

The usable N-terminal extensions of mammalian GalT enzymes are characterised in that they have a length of about 10-20 amino acids and that they contain the motif [K/R]-X-[K/R] (in which K/R means either a lysine or an arginine residue and X can be any amino acid) in the first 10 amino-terminal amino acids of the cytosolic tail sequence.

In certain embodiments, the N-terminal amino acid sequence extension comprises the first 13 amino acid residues of the human β-1,4-galactosyltransferase polypeptide 1 sequence, i.e., MRLREPLLSGSAA (SEQ ID NO:21), see FIG. 1. In other embodiments, the CTS of the non-mammalian GalT is replaced with the CTS from another Golgi-localized protein; the replacement could for example be derived from the CTS from the rat α2,6-sialyltransferase (Genbank accession M18769).

In certain embodiments the plant cells or plants express a functional non-mammalian β1,4-galactosyltransferase that is at least 85% identical to chicken β1,4-galactosyltransferase nucleic acid sequence (SEQ ID NO:1). In other embodiments the functional non-mammalian β1,4-galactosyltransferase is 90%, 91%, 92%, 93%, 94%, 95%, 96%, 97%, 98%, or 99% identical to chicken β1,4-galactosyltransferase nucleic acid sequence (SEQ ID NO:1).

In certain embodiments nucleic acids and vectors thereof are provided that are 85%, 90%, 91%, 92%, 93%, 94%, 95%, 96%, 97%, 98%, or 99% identical to chicken β1,4-galactosyltransferase nucleic acid sequence (SEQ ID NO:1).

In certain embodiments the plant cells or plants express a functional non-mammalian β1,4-galactosyltransferase that is at least 65% identical to chicken β1,4-galactosyltransferase amino acid sequence (SEQ ID NO:2). In other embodiments the functional non-mammalian β1,4-galactosyltransferase is 75%, 85%, 90%, 91%, 92%, 93%, 94%, 95%, 96%, 97%, 98%, or 99% identical to chicken β1,4-galactosyltransferase amino acid sequence (SEQ ID NO:2).

In certain embodiments the plant cells or plants express a functional non-mammalian β1,4-galactosyltransferase that is at least 65% identical to chicken β1,4-galactosyltransferase amino acid sequence (SEQ ID NO:2) and comprises a modified N-terminus comprising a mammalian extension. The mammalian extension may comprise, for example, the first 13 amino acid residues of the human β-1,4-galactosyltransferase polypeptide 1 sequence, i.e., MRLREPLLSGSAA (SEQ ID NO:21), or the CTS of the non-mammalian GalT is replaced with the CTS from another Golgi-localized protein; the replacement could for example be derived from the CTS from the rat α2,6-sialyltransferase (Genbank accession M18769). In other embodiments the functional non-mammalian β1,4-galactosyltransferase comprising the mammalian extension is 75%, 85%, 90%, 91%, 92%, 93%, 94%, 95%, 96%, 97%, 98%, or 99% identical to chicken β1,4-galactosyltransferase amino acid sequence (SEQ ID NO:2).

In certain embodiments nucleic acids and vectors thereof are provided comprising a mammalian extension or altered CTS region as described above, that are 85%, 90%, 91%, 92%, 93%, 94%, 95%, 96%, 97%, 98%, or 99% identical to chicken β1,4-galactosyltransfer nucleic acid sequence (SEQ ID NO:1) with regards to the chicken β1,4-galactosyltransferase nucleic acid sequence only; that is sequence identity is not established over the mammalian extension or altered CTS region.

In certain embodiments the plant cells or plants express a functional non-mammalian β1,4-galactosyltransferase that is at least 85% identical to zebrafish β1,4-galactosyltransferase nucleic acid sequence (SEQ ID NO:13). In other embodiments the functional non-mammalian β1,4-galactosyltransferase is 90%, 91%, 92%, 93%, 94%, 95%, 96%, 97%, 98%, or 99% identical to zebrafish β1,4-galactosyltransferase nucleic acid sequence (SEQ ID NO:13).

In certain embodiments nucleic acids and vectors thereof are provided that are 85%, 90%, 91%, 92%, 93%, 94%, 95%, 96%, 97%, 98%, or 99% identical to zebrafish β1,4-galactosyltransferase nucleic acid sequence (SEQ ID NO:13).

In certain embodiments the plant cells or plants express a functional non-mammalian β1,4-galactosyltransferase that is at least 65% identical to zebrafish β1,4-galactosyltransferase amino acid sequence (SEQ ID NO:14). In other embodiments the functional non-mammalian β1,4-galactosyltransferase is 75%, 85%, 90%, 91%, 92%, 93%, 94%, 95%, 96%, 97%, 98%, or 99% identical to zebrafish β1,4-galactosyltransferase amino acid sequence (SEQ ID NO:14).

In certain embodiments the plant cells or plants express a non-mammalian β1,4-galactosyltransferase that is at least 65% identical to zebrafish β1,4-galactosyltransferase amino acid sequence (SEQ ID NO:14) and comprises a modified N-terminus comprising a mammalian extension. In other embodiments the functional non-mammalian β1,4-galactosyltransferase comprising the mammalian extension is 75%, 85%, 90%, 91%, 92%, 93%, 94%, 95%, 96%, 97%, 98%, or 99% identical to zebrafish β1,4-galactosyltransferase amino acid sequence (SEQ ID NO:14).

In certain embodiments the plant cells or plants express a non-mammalian β1,4-galactosyltransferase that is at least 65% identical to zebrafish β1,4-galactosyltransferase amino acid sequence (SEQ ID NO:14), wherein the CTS of the zebrafish β1,4-galactosyltransferase is replaced with the CTS from another Golgi-localized protein. In other embodiments the functional non-mammalian β1,4-galactosyltransferase comprising the mammalian extension is 75%, 85%, 90%, 91%, 92%, 93%, 94%, 95%, 96%, 97%, 98%, or 99% identical to zebrafish β1,4-galactosyltransferase amino acid sequence (SEQ ID NO:14).

In certain embodiments nucleic acids and vectors thereof are provided comprising a mammalian extension or altered CTS region as described above, that are 85%, 90%, 91%, 92%, 93%, 94%, 95%, 96%, 97%, 98%, or 99% identical to zebrafish β1,4-galactosyltransferase nucleic acid sequence (SEQ ID NO:13) with regards to the zebrafish β1,4-galactosyltransferase nucleic acid sequence only; that is sequence identity is not established over the mammalian extension or altered CTS region.

In some embodiments the non-mammalian β-1,4-galactosyltransferase is chicken or fish β-1,4-galactosyltransferase, while the N-terminal extension is derived from human β-1,4-galactosyltransferase gene or the CTS is derived from rat sialyltransferase. In certain embodiments the chicken β-1,4-galactosyltransferase has the amino acid sequence of SEQ ID NO:2 and the fish β-1,4-galactosyltransferase is derived from zebrafish (*Danio rerio*) and has the amino acid sequence of SEQ ID NO: 14. In certain embodiments, the enzyme is encoded by the nucleic acid of SEQ ID NO:1 and SEQ ID NO:13, respectively.

In some embodiments plant cells or plants are provided that express non-mammalian β1,4-galactosyltransferases, such as those derived from chicken and fish. In certain embodiments the plant cells or plants express functional wild-type chicken β1,4-galactosyltransferase (SEQ ID NO:2). In some embodiments the above mentioned plant cell or plant produces at least hybrid-type N-linked glycans (i.e., N-glycans at least comprising the trimannosylated chitobiose core, one additional mannose and a galactosylated GlcNAc residue at the nonreducing end on the α1,3-arm of the N-glycan) lacking both β1,2-xylose and α1,3-fucose residues. In certain embodiments the total amount of hybrid-type N-linked glycans lacking both β1,2-xylose and α1,3-fucose residues is 2-fold increased over the amount produced by a plant cell or plant expressing wild-type human β1,4-galactosyltransferase. In other embodiments the amount is increased by 3-, 4-, 5-, 6-, 7-, 8-, 9-, 10-, 15-, 20-, 50-, 100-, 250-, 500-, 1000-, or 10,000-fold increased.

In other embodiments the plant cells or plants express chicken β1,4-galactosyltransferase comprising a 13 amino acid extension at the N-terminus (SEQ ID NO:9). In some embodiments the above mentioned plant cell or plant produces at least hybrid-type N-linked glycans lacking both β1,2-xylose and α1,3-fucose residues. In certain embodiments the total amount of hybrid-type N-linked glycans lacking both β1,2-xylose and α1,3-fucose residues is 2-fold increased over the amount produced by a plant cell or plant expressing wild-type human β1,4-galactosyltransferase. In other embodiments the amount is increased by 3-, 4-, 5-, 6-, 7-, 8-, 9-, 10-, 15-, 20-, 50-, 100-, 250-, 500-, 1000-, or 10,000-fold increased.

In other embodiments the plant cells or plants express chicken β1,4-galactosyltransferase comprising a sialyltransferase CTS extension at the N-terminus (SEQ ID NO:11). In some embodiments the above mentioned plant cell or plant produces at least hybrid-type N-linked glycans lacking both β1,2-xylose and α1,3-fucose residues, as well as bi-antennary N-glycans comprising at least one galactosylated GlcNAc residue (i.e., N-glycans with at least one galactosylated GlcNAc residue at the non-reducing end in addition to the trimannosylated chitobiose core). In certain embodiments the total amount of hybrid-type N-linked glycans lacking both β1,2-xylose and α1,3-fucose residues and/or bi-antennary N-glycans comprising at least one galactosylated GlcNAc residue is 2-fold increased over the amount produced by a plant cell or plant expressing wild-type human β1,4-galactosyltransferase. In other embodiments the amount is increased by 3-, 4-, 5-, 6-, 7-, 8-, 9-, 10-, 15-, 20-, 50-, 100-, 250-, 500-, 1000-, or 10,000-fold increased.

In certain embodiments the plant cells or plants express wild-type zebrafish β1,4-galactosyltransferase (SEQ ID NO:14). In some embodiments the above mentioned plant cell or plant produces at least bi-antennary N-linked glycans, as well as bi-antennary N-glycans comprising at least one galactosylated GlcNAc residue. In certain embodiments the total amount of bi-antennary N-linked glycans and/or bi-antennary N-glycans comprising at least one galactosylated GlcNAc residue is 2-fold increased over the amount produced by a plant cell or plant expressing wild-type human β1,4-galactosyltransferase. In other embodiments the amount is increased by 3-, 4-, 5-, 6-, 7-, 8-, 9-, 10-, 15-, 20-, 50-, 100-, 250-, 500-, 1000-, or 10,000-fold increased.

In other embodiments the plant cells or plants express zebrafish β1,4-galactosyltransferase comprising a 13 amino acid extension at the N-terminus (SEQ ID NO:16). In some embodiments the above mentioned plant cell or plant produces at least bi-antennary N-linked glycans, as well as bi-antennary N-glycans comprising at least one galactosylated GlcNAc residue. In certain embodiments the total amount of bi-antennary N-linked glycans and/or bi-antennary N-glycans comprising at least one galactosylated GlcNAc residue is 2-fold increased over the amount produced by a plant cell or plant expressing wild-type human β1,4-galactosyltransferase. In other embodiments the amount is increased by 3-, 4-, 5-, 6-, 7-, 8-, 9-, 10-, 15-, 20-, 50-, 100-, 250-, 500-, 1000-, or 10,000-fold increased.

In other embodiments the plant cells or plants express zebrafish β1,4-galactosyltransferase comprising a sialyltransferase CTS extension at the N-terminus (SEQ ID NO:18). In some embodiments the above mentioned plant cell or plant produces at least bi-antennary N-linked glycans, as well as bi-antennary N-glycans comprising at least one galactosylated GlcNAc residue. In certain embodiments the total amount of bi-antennary N-linked glycans and/or bi-antennary N-glycans comprising at least one galactosylated GlcNAc residue is 2-fold increased over the amount produced by a plant cell or plant expressing wild-type human β1,4-galactosyltransferase. In other embodiments the amount is increased by 3-, 4-, 5-, 6-, 7-, 8-, 9-, 10-, 15-, 20-, 50-, 100-, 250-, 500-, 1000-, or 10,000-fold increased.

In certain embodiments the nucleic acids encoding a non-mammalian β-1,4-galactosyltransferase that is extended at the N-terminus with a sequence derived from the N-terminus of a mammalian β1,4-galactosyltransferase 1 or with an N-terminal CTS sequence from a mammalian β-1,4-galactosyltransferase or sialyltransferase, described herein, may alternatively be extended with any other CTS sequence from a Golgi-localized protein from plants, animals or fungi resulting in trans-Golgi localized expression of the non-mammalian GalT catalytic domain to which it is fused at its C-terminus. Such nucleic acids are provided herein.

In certain embodiments the plant cells or plants express in addition to a non-mammalian β-1,4-galactosyltransferase, described herein, a second protein, preferably a mammalian protein to be provided with a galactosylated N-linked glycan, producing a heterologuos glycoprotein of which β1,4-galactosylation of its N-glycans, biantennary or alternatively in a hybrid form is of interest. Such glycoproteins produced in plant cells or plants expressing a non-mammalian β-1,4-galactosyltransferase are also provided herein.

In certain embodiments, said second protein is expressed from a nucleic acid that encodes an antibody heavy and/or light chain or a functional fragment thereof.

The skilled person is well acquainted with expression of recombinant nucleic acids in cellular expression systems, such as for example plant cells that can generate whole plants. An expression vector may be used for expression of recombinant nucleic acids in cellular expression systems. In certain embodiments, such a vector will comprise a DNA encoding a non-mammalian β-1,4-galactosyltransferase or an enzymatically active derivative or part thereof that optionally is extended at the N-terminus or in which its own CTS is replaced with an N-terminal CTS sequence from another Golgi-localized protein in such a way that it will have galactosylating activity on N-linked glycans. A suitable vector may further comprise regulatory elements such as a promotor, and optionally at least one selection marker expressible in said cellular expression system. The expression vector may further encode at least one further DNA encoding a mammalian glycoprotein which can be glycosylated.

In certain embodiments a plants or plant cell is provided that has been provided with a functional non-mammalian enzyme (optionally with N-terminal extension derived from a mammalian GalT or in which the endogenous CTS has been replaced with another CTS from a Golgi-localized protein from plants) providing N-glycan biosynthesis that is normally not present in plants thereby for example providing the capacity to extend an N-linked glycan by the addition of a galactose. In certain embodiments expression is transient while in other embodiments, plants or plant cells are provided wherein expression of non-mammalian β-1,4-galactosyltransferase or an enzymatically active derivative or part thereof, and optionally of an additional heterologous protein that may be glycosylated, is stable. In certain embodiments a third protein is additionally expressed by a plant cell or plant. Such a third protein may be an enzyme which further processes the glycosylation of said galactosylated second protein. In certain embodiments, a plant cell or plant may comprise two nucleic acids encoding for a monomer of a dimeric or multimeric protein. In certain embodiments separate nucleic acids are provided for both an antibody light and heavy chain or functional fragment thereof or for any other dimeric or multimeric protein of interest. Of course, it is not necessary that a full protein is expressed. In certain embodiments a plant cell or plant according to the invention expresses only a fragment, preferably a functional fragment of said second mammalian glycoprotein, said fragment having at least one activity of the whole protein and further being characterized by for example a truncated polypeptide chain, or a not fully extended glycan, for example only extended with galactose. Such glycoproteins or fragments thereof are also provided herein.

The addition of plant-specific residues such as β1,2-xylose and α1,3-fucose residues to glycoproteins produced in plants makes such glycoproteins less suited for pharmaceutical use, because of the undesirable antigenic and immunogenic characteristics of β1,2-xylose and α1,3-fucose residues in mammals. To substantially limit the number of β1,2-xylose and α1,3-fucose residues on plant produced glycoproteins or to achieve a complete lack of these residues, strategies are required that modify the genome of plant cells in such a manner that the synthesized glycoproteins display humanized or mammalized characteristics.

In certain embodiments, plant cells or plants are provided, wherein a second protein, and preferably a second mammalian protein or functional fragment thereof, comprises an extended N-linked glycan that is devoid of xylose and/or of fucose. Plant-derived galactosylated glycoproteins still may contain xylose and fucose residues. In certain embodiments, non-mammalian β1,4-galactosyltransferase or a modified mersion thereof described elsewhere herein, is therefore expressed in plants in such a way that the enzyme acts in the Golgi apparatus on the natural substrates, that is, subsequent to the action of N-acetylglucosaminyltransferase I, Golgi-mannosidase II and N-acetylglucosaminyltransferase II, and in plants, provided that these enzymes are not inhibited in another way, subsequent to or during the action of xylosyltransferase and fucosyltransferase. A galactosylated protein obtained from a plant is herein referred to as plant-derived. Such plant-derived galactosylated proteins are also provided herein.

To mammalize the glycosylation of plants for the production of tailor-made glycoproteins in plants xylosyltransferases and fucosyltransferases may be knocked out or silenced and at least one of several mammalian glycosyltransferases has to be expressed. Providing the xylosyltransferase and fucosyltransferase knock-outs and thereby reducing the unwanted glycosylation potential of plants is a feasible option because for example an *Arabidopsis thaliana* mutant mutated in the gene encoding N-acetylglucosaminyltransferase I was completely viable. As N-acetylglucosaminyltransferase I is the enzyme initiating the formation of complex glycans this plant completely lacks the xylose and fucose residues containing complex glycans.

In certain embodiments plants or plant cells are provided wherein a non-mammalian β-1,4-galactosyltransferase or an enzymatically active derivative or part thereof, an additional heterologous protein that may be glycosylated, and optionally additionally a third protein providing further N-glycan biosynthesis are expressed, and wherein the genes encoding enzymes responsible for xylose and/or fucose addition are knocked-out or wherein expression of these genes is silenced using antisense or RNAi technology. Methods for gene knockouts in plants or gene silencing through RNAi are well known in the art.

RNA interference (RNAi) is a mechanism that inhibits gene expression at the stage of translation or by hindering the transcription of specific genes. Small interfering RNA strands (siRNA) are key to the RNAi process, and have complementary nucleotide sequences to the targeted RNA strand. Specific RNAi pathway proteins, such as dicer (RISC), are guided by the siRNA to the targeted messenger RNA (mRNA), where they cleave the target into smaller portions that can no longer be translated into protein. RNA interference is a vital part of the immune response to viruses and other foreign genetic material, especially in plants.

RNA interference has been used for applications in plant biotechnology, for example in the engineering of food plants that produce lower levels of natural plant toxins, in tomato plants to reduce the levels of allergens, and in tomatoes to fortify the plant with dietary antioxidants (Sunilkumar G. et al. (2006) *Proc Natl Acad Sci USA* 103 (48): 18054-9; Siritunga D, Sayre R (2003) *Planta* 217 (3): 367-73; Le L. et al. (2006) *Plant Biotechnol J* 4 (2): 231-42; Niggeweg R. et al. (2004) *Nat Biotechnol* 22 (6): 746-54). Such techniques take advantage of the stable and heritable RNAi phenotype in plant stocks.

In other embodiments methods are provided to specifically separate and purify glycoproteins comprising extended N-linked glycan that is devoid of xylose and/or of fucose. Several types of separation techniques exist, such as (im-muno) affinity purification or size-exclusion chromatography or electrophoresis, to mediate the required purification. Such methods are well known in the art (see, e.g., US 2008/0003680).

One of skill in the art will appreciate that the invention is not limited to plants or plant cells but also provides other organisms like animals, fungi or yeast, or cell lines like mammalian cell lines or insect cell lines with the capacity to produce a glycoprotein (essentially nonsialylated) according to the invention wherein said N-linked glycan comprises a galactose.

Generating transiently or stably transformed plants which produce tailored glycoproteins of commercial interest may be established, in some embodiments, by inoculating plant cells or tissues with *Agrobacterium* strains containing a (binary) vector which comprises both nucleotide sequences encoding N-glycosylation modifying enzymes as described herein and genes encoding commercially interesting heterologous glycoproteins. Alternatively, in some embodiments, transiently or stably transformed plants which produce tailored glycoproteins of commercial interest may be generated by simultaneous inoculation (co-transformation) of two or more *Agrobacterium* strains each carrying a vector comprising either nucleotide sequences encoding N-glycosylation modifying enzymes or nucleotide sequences encoding heterologous glycoproteins of commercial interest. Alternatively, in some embodiments, transiently or stably transformed plants which produce tailored glycoproteins of commercial interest can be generated by (multiple) crossing (s) of plants with modified N-glycosylation with plants which express polynucleotides encoding proteins of commercial interest. In all of these procedures, the vector may also comprise a nucleic acid sequence which confers resistance against a selection agent.

In order to obtain satisfactory expression of the proteins involved in N-glycosylation and of the glycoproteins or polypeptides of commercial interest, the nucleotide sequences may be adapted to the specific transcription and translation machinery of the host plant as known to people skilled in the art. For example, silent mutations in the coding regions may be introduced to improve codon usage and specific promoters may be used to drive expression of said genes in relevant plant tissues. Promoters which are developmentally regulated or which can be induced at will, may be used to ensure expression at the appropriate time, for example, only after plant tissues have been harvested from the field and brought into controlled conditions. In all these cases, choice of expression cassettes of the glycosylation modifying proteins and of the glycoproteins of commercial interest should be such that they express in the same cells to allow desired post-translational modifications to the glycoprotein.

In certain embodiments tobacco plants are provided, or a plant related to the genus *Nicotiana* ssp., preferably *N. tabacum* or *N. benthamiana*. In other embodiments other relatively easily transformable plants, such as *Arabidopsis thaliana*, or *Zea mays*, or plants related thereto may be used. For the production of recombinant glycoproteins, use of duckweed offers specific advantages. The plants are in general small and reproduce asexually through vegetative budding. Most duckweed species have all the tissues and organs of much larger plants including roots, stems, flowers, seeds and fronds. Duckweed can be grown cheaply and very fast as a free floating plant on the surface of simple liquid solutions in full containment from which they can easily be harvested. In certain embodiments duckweed is recombinantly provided with a non-mammalian β-1,4-galactosyltransferase or modified version thereof described herein and/or genes encoding commercially interesting heterologous glycoproteins. The duckweed plant may for example comprise the genus *Spirodella*, genus *Wolffia*, genus *Wolffiella*, or the genus *Lemna, Lemna minor, Lemna miniscule* and *Lemna gibba*.

In certain embodiments, expression in tomato fruits is provided. Tomatoes can be easily grown in greenhouses under contained and controlled conditions and tomato fruit biomass can be harvested continuously throughout the year in enormous quantities. The watery fraction containing the glycoproteins of interest can be readily separated from the rest of the tomato fruit which allows easier purification of the glycoprotein. In certain embodiments expression in storage organs of other crops is provided including, but not limited to, the kernels of corn, the tubers of potato and the seeds of rape seed or sunflower, which are attractive alternatives that provide huge biomass in organs for which harvesting and processing technology is readily available.

In some embodiments methods are provided for providing a transgenic plant, such as transgenic *Nicotiana* ssp., preferably *N. tabacum* or *N. benthamiana, Arabidopsis thaliana*, or corn, potato, tomato, or duckweed, which are capable of expressing a recombinant protein, with the capacity to extend an N-linked glycan with galactose comprising crossing said transgenic plant with a plant comprising at least one optionally functional non-mammalian protein, for example, a transporter or an enzyme providing N-glycan biosynthesis that is normally not present in plants, harvesting progeny from said crossing and selecting a desired progeny plant expressing said recombinant protein and expressing a functional non-mammalian enzyme involved in mammalian-like N-glycan biosynthesis that is normally not present in plants. In one embodiment, the method may further comprise selecting a desired progeny plant expressing said recombinant protein comprising an extended N-linked glycan at least comprising galactose.

In some embodiments plants are provided expressing said recombinant glycoprotein comprising an N-linked glycan and expressing non-mammalian enzyme involved in mammalian-like N-glycan biosynthesis. In additional embodiments, the invention also provides for use of a transgenic plant to produce a desired glycoprotein or functional fragment thereof, in particular wherein said glycoprotein or functional fragment thereof comprises an extended N-linked glycan at least comprising galactose.

In some embodiments methods are provided for providing a transgenic plant cell suspension culture, such as transgenic *Nicotiana* spp., preferably *N. tabacum* BY2, *Daucus carota* or *Arabidopsis thaliana* cell suspension, which are capable of expressing a recombinant protein, with the capacity to extend an N-linked glycan with galactose.

In some embodiments methods are provided for providing a transgenic moss, such as transgenic *Bryophytaea*, preferably *Physcomitrella patens*, or *Funaria hygrometrica, Cer-*

*atodon purpureus*, which are capable of expressing a recombinant protein, with the capacity to extend an N-linked glycan with galactose.

In some embodiments methods are provided for obtaining a desired glycoprotein or functional fragment thereof comprising for example an extended N-linked glycan at least comprising galactose. Said methods comprising cultivating a plant as described herein until said plant has reached a harvestable stage, for example when sufficient biomass has grown to allow profitable harvesting, followed by harvesting said plant with established techniques known in the art and fractionating said plant with established techniques known in the art to obtain fractionated plant material and at least partly isolating said glycoprotein from said fractionated plant material.

In some embodiments plant-derived glycoproteins or functional fragments thereof are provided comprising an extended N-linked glycan at least comprising galactose, for example obtained by a method as explained above. Such a plant-derived glycoprotein with an extended glycan at least comprising galactose essentially can be any desired glycoprotein that can be expressed in a plant. For example, antibodies, vaccines, cytokines, FSH, TSH and other hormone glycoproteins, other hormones like EPO, enzymes like antitrypsin or lipase, cellular adhesion molecules like NCAM or collagen can be produced in plants and be provided with essentially mammalian glycosylation patterns.

In some embodiments, the invention provides use of such a plant-derived glycoprotein or functional fragment thereof as described herein for the production of a pharmaceutical composition, for example for the treatment of a patient with an antibody, a hormone, a cytokine, a vaccine antigen, an enzyme, or the like. Such a pharmaceutical composition comprising a glycoprotein or functional fragment thereof is also provided.

Plant Transformation

Expression of proteins, such as for example non-mammalian enzymes providing N-glycan biosynthesis, as well as glycoproteins, such as antibodies, cytokines, vaccines, hormones and the like, can be performed by using methods known in the art. For example, by stable expression via *Agrobacterium*-mediated transformation, electroporation or particle bombardment, or by transient expression using viral vectors such as PVX, for example, or agrofiltration, or other method known in the art. The glycosyltransferases of the invention, capable of glycan biosynthesis, and/or the glycoprotein which undergoes glycosylation may be expressed under control of a specific promoter to facilitate expression in certain tissues or organs. A DNA sequence coding for the desired polypeptide of the non-mammalian glycosyltransferase and/or glycoproteins described herein, for example a cDNA or a genomic sequence encoding a full length protein, may be used to construct a recombinant expression cassette which can be introduced into the desired plant.

Isolated nucleic acids as described herein, e.g. comprising sequences such as SEQ ID NOs: 1, 8, 10, 13, 15 and 17, can be introduced into plants according to techniques known in the art. Generally, recombinant expression cassettes as described above and suitable for transformation of plant cells are prepared. The isolated nucleic acids described herein can then be used for transformation. In this manner, genetically modified plants, plant cells, plant tissue, seed, and the like can be obtained.

Transformation protocols may vary depending on the type of plant cell, i.e., monocot or dicot, targeted for transformation. Suitable methods of transforming plant cells include microinjection (Crossway et al. (1986) Biotechniques 4: 320-334), electroporation (Riggs et al (1986) Proc. Natl. Acad. Sci. USA 83: 5602-5606), *Agrobacterium* mediated transformation (see for example, Zhao et al. U.S. Pat. No. 5,981,840; Hinchee et al. (1988) Biotechnology 6: 915-921), direct gene transfer (Paszkowski et al (1984) EMBO J. 3: 27172722), and ballistic particle acceleration (see, for example, Sanford et al. U.S. Pat. No. 4,945,050; Tomes et al. "Direct DNA Transfer into Intact Plant Cells via Microprojectile Bombardment" In Gamborg and Phillips (Eds.) Plant Cell, Tissue and Organ Culture: Fundamental Methods, Springer-Verlag, Berlin (1995); and McCabe et al. (1988) Biotechnology 6: 923-926).

The cells which have been transformed may be grown into plants in accordance with conventional methods. See, for example, McCormick et al. (1986) Plant Cell Reports, 5: 81-84. These plants may then be grown, and either pollinated with the same transformed strain or different strains, and the resulting hybrid having the desired phenotypic characteristic identified. Two or more generations may be grown to ensure that the subject phenotypic characteristic is stably maintained and inherited and then seeds harvested to ensure the desired phenotype or other property has been achieved.

Transgenic Plant Regeneration

Plant cells transformed with a plant expression vector can be regenerated, e.g., from single cells, callus tissue or leaf discs according to standard plant tissue culture techniques. It is well known in the art that various cells, tissues, and organs from almost any plant can be successfully cultured to regenerate an entire plant. Plant regeneration from cultured protoplasts is described in Evans et al., Protoplasts Isolation and Culture, Handbook of Plant Cell Culture, Macmillan Publishing Company, New York, pp. 124 176 (1983); and Binding, Regeneration of Plants, Plant Protoplasts, CRC Press, Boca Raton, pp. 21-73 (1985).

The regeneration of plants containing the foreign gene introduced by *Agrobacterium* from leaf explants can be achieved as described by Horsch et al., Science, 227: 1229-1231 (1985). In this procedure, transformants are grown in the presence of a selection agent and in a medium that induces the regeneration of shoots in the plant species being transformed as described by Fraley et al., Proc. Natl. Acad. Sci. (U.S.A.), 80: 4803 (1983). This procedure typically produces shoots within two to four weeks and these transformant shoots are then transferred to an appropriate root-inducing medium containing the selective agent and an antibiotic to prevent bacterial growth. Transgenic plants of the present invention may be fertile or sterile.

Regeneration can also be obtained from plant callus, explants, organs, or parts thereof. Such regeneration techniques are described generally in Klee et al., Annu Rev Plant Phys. 38: 467-486 (1987). The regeneration of plants from either single plant protoplasts or various explants is well known in the art. See, for example, Methods for Plant Molecular Biology, A. Weissbach and H. Weissbach, eds., Academic Press, Inc., San Diego, Calif. (1988). This regeneration and growth process includes the steps of selection of transformant cells and shoots, rooting the transformant shoots and growth of the plantlets in soil. For maize cell culture and regeneration see generally, The Maize Handbook, Freeling and Walbot, Eds., Springer, New York (1994); Corn and Corn Improvement, 3rd edition, Sprague and Dudley Eds., American Society of Agronomy, Madison, Wis. (1988).

One of skill will recognize that after the recombinant expression cassette is stably incorporated in transgenic plants and confirmed to be operable, it can be introduced into other plants by sexual crossing. Any of a number of standard breeding techniques can be used, depending upon the species to be crossed. In vegetatively propagated crops, mature transgenic plants can be propagated by the taking of cuttings or by tissue culture techniques to produce multiple identical plants.

Selection of desirable transgenics is made and new varieties are obtained and preferably propagated vegetatively for commercial use. In seed propagated crops, mature transgenic plants can be self crossed to produce a homozygous inbred plant. The inbred plant produces seed containing the newly introduced heterologous nucleic acid. These seeds can be grown to produce plants that would produce the selected phenotype.

Parts obtained from the regenerated plant, such as flowers, seeds, leaves, branches, fruit, and the like are included in the invention, provided that these parts comprise cells comprising the isolated nucleic acids described herein. Progeny and variants, and mutants of the regenerated plants are also included within the scope of the invention, provided that these parts comprise the introduced nucleic acid sequences.

Transgenic plants expressing the selectable marker can be screened for transmission of the nucleic acids described herein by, for example, standard immunoblot and DNA detection techniques. Transgenic lines are also typically evaluated on levels of expression of the heterologous nucleic acid. Expression at the RNA level can be determined initially to identify and quantitate expression-positive plants. Standard techniques for RNA analysis can be employed and include PCR amplification assays using oligonucleotide primers designed to amplify only the heterologous RNA templates and solution hybridization assays using heterologous nucleic acid-specific probes. The RNA positive plants can then be analyzed for protein expression by Western immunoblot analysis using the specifically reactive antibodies provided herein. In addition, in situ hybridization and immunocytochemistry according to standard protocols can be performed using heterologous nucleic acid specific polynucleotide probes and antibodies, respectively, to localize sites of expression within transgenic tissue. Generally, a number of transgenic lines are screened for the incorporated nucleic acid to identify and select plants with the most appropriate expression profiles.

In certain embodiments a transgenic plant is provided that is homozygous for the added heterologous nucleic acid; i.e., a transgenic plant that contains two added nucleic acid sequences, one gene at the same locus on each chromosome of a chromosome pair. A homozygous transgenic plant can be obtained by sexually mating (selfing) a heterozygous transgenic plant that contains a single added heterologous nucleic acid, germinating some of the seed produced and analyzing the resulting plants produced for altered expression of a polynucleotide described herein relative to a control plant (i.e., native, non-transgenic). Back-crossing to a parental plant and out-crossing with a non-transgenic plant are also contemplated.

In certain embodiments a process for the production of a transgenic plant or a transgenic plant cell is provided comprising (a) insertion of a DNA into the genome of a plant or a plant cell, said DNA comprising a nucleic acid sequence which encodes a non-mammalian β-1,4-galactosyltransferase, optionally extended with a mammalian N-terminal sequence, as described herein, or encoding said GalT in which its CTS has been replaced with that of another Golgi-localized protein, as described herein, or enzymatically active derivatives or parts thereof, and preferably in addition at least one mammalian protein requiring galactosylation of its N-linked glycan which DNA additionally encodes at least one selection marker expressible in said plant or said plant cell, (b) selection of transgenic plants or plant cells which have taken up said DNA according to (a); and (c) culturing of the desired transgenic plant or the desired transgenic plant cell in a suitable culture medium. The skilled person will understand that term "a protein comprising a galactosylated N-linked glycan" in relation to a nucleic acid molecule encoding said protein merely encodes the polypeptide, whereas the galactosylated N-linked glycan is a result of processing of the protein in the Golgi.

In some embodiments additional methods are provided for producing a transgenic plant that expresses a recombinant GalT protein and a protein comprising a galactosylated N-linked glycan. Such methods may for instance comprise crossing a transgenic plant described herein with another plant, harvesting progeny from said crossing and selecting a desired progeny plant expressing the recombinant GalT protein and expressing a recombinant mammalian glycoprotein, in particular a protein comprising a galactosylated N-glycan, or functional fragment thereof.

Purification of Proteins

In certain embodiments methods for obtaining a desired glycoprotein or functional fragment thereof comprise cultivating a plant described herein until said plant has reached a harvestable stage, harvesting and fractionating the plant to obtain fractionated plant material and at least partly isolating said glycoprotein from said fractionated plant material. In certain embodiment methods for obtaining a desired glycoprotein or functional fragment thereof comprise growing plant cells in cell culture in a fermentor until said cell culture has reached a harvestable stage or the desired glycoprotein can be collected from the medium. The glycoproteins described herein, such as e.g., antibodies, vaccines, cytokines and hormones, may be purified by standard techniques well known to those of skill in the art. Such recombinantly produced proteins may be directly expressed or expressed as a fusion protein. The recombinant protein is purified by a combination of cell lysis (e.g., sonication, French press) and affinity chromatography or other affinity-based method. For fusion products, subsequent digestion of the fusion protein with an appropriate proteolytic enzyme releases the desired recombinant protein.

The proteins described herein, recombinant or synthetic, may be purified to substantial purity by standard techniques well known in the art, including detergent solubilization, selective precipitation with such substances as ammonium sulfate, column chromatography, immunopurification methods, and others. See, for instance, R. Scopes, Protein Purification: Principles and Practice, Springer-Verlag: New York (1982); Deutscher, Guide to Protein Purification, Academic Press (1990). For example, antibodies may be raised to the proteins as described herein. Purification from E. coli can be achieved following procedures described in U.S. Pat. No. 4,511,503. The protein may then be isolated from cells expressing the protein and further purified by standard protein chemistry techniques as described herein. Detection of the expressed protein is achieved by methods known in the art and include, for example, radioimmunoassays, Western blotting techniques or immunoprecipitation.

EXAMPLES

Example 1

Identification of Putative Non-Mammalian β1,4 GalTs

The family of β-1,4-galactosyltransferases (GalT) comprises at least seven members, of which several have been cloned but only very few have been characterized. The β-1, 4-galactosyltransferases of human and bovine origin have been best characterized and were shown to be able to add a galactose residue in β-1,4-linkage to terminal GlcNAc residue on an N-glycan. Putative GalT genes involved in N-glycosylation were identified among non-mammalian species gene sequences based on homology. FIG. 1 shows a Clustal W alignment of mammalian GalT gene sequences (human, mouse and bovine) and non-mammalian putative GalT gene sequences (chicken, zebrafish and frog). Remarkably, the mammalian amino terminus (boxed, solid lines), which is cytosolic and adjacent to the transmembrane region (TM, boxed, dashed lines) and which putatively is involved in Golgi-localization is not conserved in GalT orthologs from non-mammalian origin, such as, for example, chicken and zebrafish (see FIG. 1).

Golgi-localization is thought to be important for GalT activity, which can be 'late' (probably trans-Golgi), meaning GalT catalytic activity occurs after the actions of other glycosyltransferases, such as, for example Man-I, GnT-I, Man-II, GnT-II, XylT and FucT in the plant, producing bi-antennary N-glycans, or GalT catalytic activity occurs 'early' (cis/medial-Golgi) that is before the activity of Man-II, XylT and FucT, thereby preventing the activity of these enzymes, producing in a plant hybrid-type N-glycans that lack fucose and xylose.

Non-mammalian GalT orthologs, for example derived from chicken and zebrafish, have not previously been characterized for their ability to add a galactose residue in β-1,4-linkage to terminal GlcNAc residue on an N-glycan, particularly not when expressed exogenously in plants. The influence of different mammalian amino termini, which may influence intracellular localization, on the production of bi-antennary or hybrid-type N-glycans and the effects on adding plant-specific fucose and xylose residues to N-glycans when expressed fused to a non-mammalian GalT ortholog in a plant has also not been investigated.

Three GalT constructs for each chicken and zebrafish were cloned and tested for N-glycosylation activity: a) wild-type, non-mammalian chicken and zebrafish β-1,4-GalT1; b) fusion proteins of the 13 amino acid conserved mammalian (human) amino terminus (see FIG. 1) extension to non-mammalian chicken and zebrafish β-1,4-GalT1; and c) fusion proteins of the mammalian cytosolic tail and transmembrane domain (CTS) derived from rat sialyltransferase gene to non-mammalian chicken and zebrafish β-1,4-GalT1, replacing the amino terminus of chicken and zebrafish β-1,4-GalT1 with the CTS of rat sialyltransferase (see Examples 2 and 3).

Example 2

Cloning and Expression of Genes Encoding the Full-Length Chicken β1,4-GalT1 Enzyme and Variants Thereof Putative chicken β1,4-GalT1 (GGal; GenBank accession U19890; SEQ Ggal, SEQ ID NO:2) has been cloned earlier, although it was not shown to be capable of galactosylating N-glycans (Shaper et al., *J Biol Chem* 272, 31389-31399, 1997). In our lab, the cDNA fragment comprising residues 114 to 362 (SEQ GgGal114-362, SEQ ID NO:3) has been amplified from chicken spleen total RNA using RT-PCR with primers GgalLEEVAST and GgGaldw (see Table 1). The resulting fragment containing the C-terminus was digested with Xho I and Bam HI and then cloned into plasmid pCASeco, the latter being a pUC19 derivative in which the Hin dIII and Eco RI sites flanking the multiple cloning site have been used to insert the sequence SEQ CASeco at the same time removing these two sites and the Eco 31I-site in the backbone. This plasmid pCASeco was digested with Xho I and Bam HI to accommodate the C-terminal GGal fragment yielding clone GgGalC.

The cDNA fragment containing the N-terminus of the GGal and comprising residues 1 to 113 was produced synthetically using PCR-based methods from long oligos. The GC-rich nature of the natural cDNA fragment hampered straightforward RT-PCR cloning and a codon optimized version of this fragment (SEQ GgGalsyn, SEQ ID NO:6) without amino acid alterations compared to the wild-type sequence was combined with clone GgGalC encoding SEQ GgGal114-362 in such a way as to create a gene (SEQ GgGalhybr, SEQ ID NO:1) encoding the wild-type GGal amino acid sequence (SEQ Ggal, SEQ ID NO:2). The gene as described under SEQ GgGalhybr was then used as starting material to create two variants, one in which its N-terminus is extended with a sequence encoding the 13 amino acid residues of the full-length human β1,4-GalT1 (GenBank accession NM_001497) and another in which the fragment encoding residues 40 to 362 comprising the catalytic domain of the GGal is fused to the C-terminus of the rat α2,6-sialyltransferase (SialT; GenBank accession M18769) N-terminal domain comprising residues 1 to 53, thus including the cytosolic tail, the transmembrane domain and a part of the stem region. The rat SialT-derived sequence contains one silent mutation with regard to the wild-type sequence.

The GGal with 13 amino acid N-terminal extension was made from the hybrid clone encoding GGal (SEQ GgGalhybr, SEQ ID NO:1) using PCR with oligo HsGgGalstart and M13 forward primer (Table 1). The resulting PCR fragment was digested with Bpi I and Xba I and cloned into likewise digested GGal clone. The resulting clone contains a gene with SEQ HsGGal (SEQ ID NO:8).

The variant with a rat SialT N-terminal domain was made from the clone encoding the complete GGal (SEQ GgGalhybr, SEQ ID NO:1) using PCR with oligos GgGal142 and M13 forward primer (Table 1). The resulting fragment was digested with Eco 31I and Bam HI and cloned into pCASeco plasmid containing the rat sequence digested with Nco I and Bam HI. The resulting clone contains a gene with SEQ sialG-Gal (SEQ ID NO:10).

Plant transformation vectors containing the three different GGal genes were made by first cloning the genes digested with Eco 31I and Bam HI into vector pRAP40 digested with Nco I and Bam HI causing the genes to be downstream of the enhanced CaMV 35S promoter and the AMV translational enhancer. pRAP40 is a pUC19 derivative containing the enhanced CaMV 35S promoter and the nos terminator flanked upstream of the promoter by the Asc I site and downstream of the terminator by the Pac I site; the entire cassette including the flanking restriction sites is described under SEQ RAP40 (SEQ ID NO:12). Each of the three cassettes comprising the promoter, one of the three genes and the terminator was then transferred separately to a modified version of binary vector pMOG22 in which the Eco RI and Hin dIII sites of the multiple cloning site have been replaced by Pac I and Asc I, respectively (Goddijn et al., 1993, Plant J 4:863-873). To this end, the pRAP-derived clones were digested with Pac I and Asc I and then cloned into Asc-Pac digested binary vector giving three different vectors ready for plant transformation. After *Agrobacterium tumefaciens*-mediated transformation of *Nicotiana tabacum*, transgenic plants expressing the GGal or its variants were selected by analyzing the N-glycans synthesized by the transformants using methods as described previously by Bakker et al., (Proc Natl Acad Sci USA 98:2899-904, 2001 and Proc Natl Acad Sci USA 103: 7577-82, 2006), for example.

Figure 4:
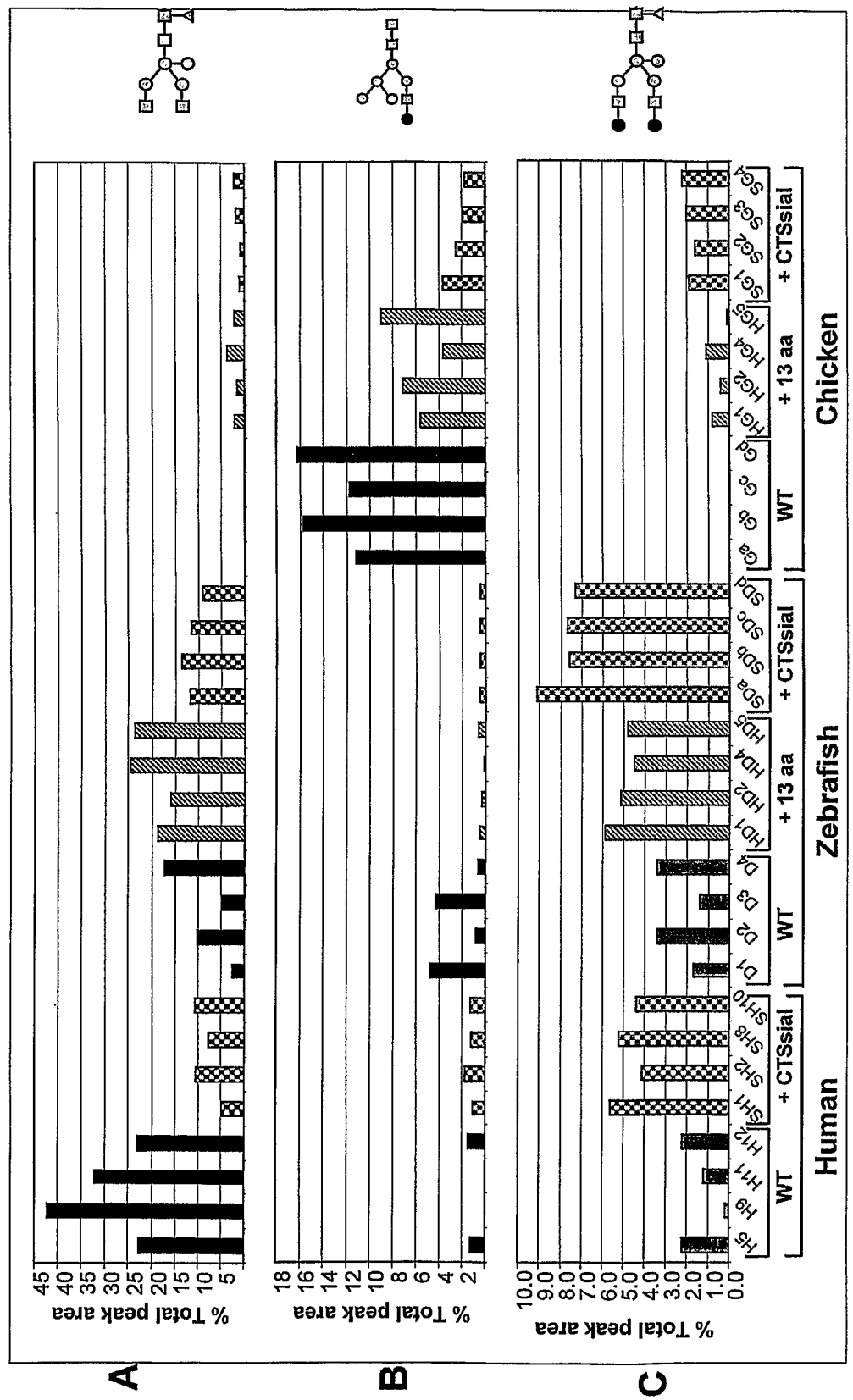
FIG. 4 depicts bar graphs summarizing results from human, zebrafish and chicken GalTs with respect to bi-antennary "wildtype" plant N-glycan (GlcNAc2-Man3-Xyl-Fuc-GlcNAc2-Asn), hybrid type N-glycans with one galactose (and lacking xylose and fucose) and bi-antennary with two galactoses (from top to bottom).

Results from MALDI-TOF analyses, see FIG. 2 and summarized in FIG. 4, right column and Table 3, of N-glycans purified from transgenic plants expressing the chicken gene show that only the chicken gene sequence with either 13 amino acid extension (HsGGal, SEQ ID NO:8) or SialT-CTS (sialGGal, SEQ ID NO:10) expression results in production of full bi-antennary N-glycans with galactose residues. Expression of wild-type chicken GalT gene results in hybrid type N-glycans only. Both 13 amino acid extension (HsGGal, SEQ ID NO:8) or SialT-CTS (sialGGal, SEQ ID NO:10) chicken GalT's also have some hybrid type galactosylated N-glycans.

Remarkably, expression of the three different GGal genes results in the almost complete lack of bi-antennary N-glycans ending in two GlcNAc residues (see Table 3 and FIG. 4, upper panel, right column), instead hybrid-type galactosylated N-glycans with one galactose and lacking both xylose and fucose are predominant, especially for expression of wild-type chicken GalT (see FIG. 4, middle panel, right column). This pattern of N-glycan production is markedly different from that obtained from plants transformed with either human GalT or GalT from zebrafish (see Table 3 and FIG. 4, left and middle column, respectively, and see below).

A reduction in plant-specific xylose and fucose residues, or the complete lack thereof, such as it is seen in the hybrid-type galactosylated N-glycans when wild-type chicken GalT is expressed in plants, is desirable when producing, for example, exogenous therapeutic glycoproteins, since β1,2-xylose and β1,3-fucose residues are not attached to glycoproteins of mammals and act as an allergen.

Example 3

Cloning and Expression of Genes Encoding the Full-Length Zebrafish β1,4-GalT1 Enzyme and Variants Thereof A putative zebrafish β1,4-GalT1 (Machingo et al., *Dev Biol* 297, 471-82, 2006; NM_001017730) has been identified, but its function has not been proven and the inventors believe the identification to be incorrect. Starting from whole zebrafish total RNA, a full-length DGal gene (SEQ Dgal, SEQ ID NO:13) has been amplified using RT-PCR with primers DrGalup and DrGaldw (see Table 2). The resulting fragment was digested with Xba I and Bam HI and then cloned into likewise digested plasmid pCASeco (see above). Sequencing showed that it was virtually identical to unidentified Genbank accession NM_001077259, albeit with three mutations as shown here (start at +1 and non-silent mutations underlined): T126C, T230G, G862C. Amino acid sequence comparison of Dgal (SEQ Dgal, SEQ ID NO:14) with putative zebrafish β1,4-GalT1 as published (Machingo et al., *Dev Biol* 297, 471-82, 2006; NM_001017730) showed that there was little sequence homology at the amino acid level, especially at the N-terminus that is supposedly involved in Golgi-localization, and C-terminus where our clone is significantly longer (see FIG. 5).

The DGal with 13 amino acid N-terminal extension was made from the clone encoding DGal (SEQ Dgal, SEQ ID NO:13) using PCR with oligos HsDrup and DrGaldw (Table 2). The resulting PCR fragment was digested with Acc I and Bpi I and cloned into likewise digested DGal clone. The resulting clone contains a gene with SEQ HsDGal (SEQ ID NO:15).

The variant with a rat SialT N-terminal domain was made from the clone encoding the complete DGal (SEQ Dgal, SEQ ID NO:13) using PCR with oligos DrGal160 and DrGaldw (Table 2). The resulting fragment was digested with Bpi I and Bam HI and cloned into pCASeco plasmid containing the rat sequence digested with Nco I and Bam HI. The resulting clone contains the DGal catalytic domain fused to the N-terminus of the rat SialT gene (SEQ sialDGal, SEQ ID NO:17).

Plant transformation vectors containing the three different DGal genes were made by first cloning the genes digested with Eco 31I and Bam HI into vector pRAP40 digested with Nco I and Bam HI causing the genes to be downstream of the enhanced CaMV 35S promoter. Each of the three cassettes comprising the promoter, one of the three genes and the terminator were then transferred separately to a modified version of binary vector pMOG22 in which the Eco RI and Hin dIII sites of the multiple cloning site have been replaced by Pac I and Asc I, respectively (Goddijn et al., 1993, Plant J 4:863-873). To this end, the pRAP-derived clones was digested with Pac I and Asc I and then cloned into Asc-Pac digested binary vector giving three different vectors ready for plant transformation. After *Agrobacterium tumefaciens*-mediated transformation of *Nicotiana tabacum*, transgenic plants expressing the DGal or its variants were selected by analyzing the N-glycans synthesized by the transformants using methods as described previously by Bakker et al., (Proc Natl Acad Sci USA 98:2899-904, 2001 and Proc Natl Acad Sci USA 103:7577-82, 2006), for example.

Figure 3:
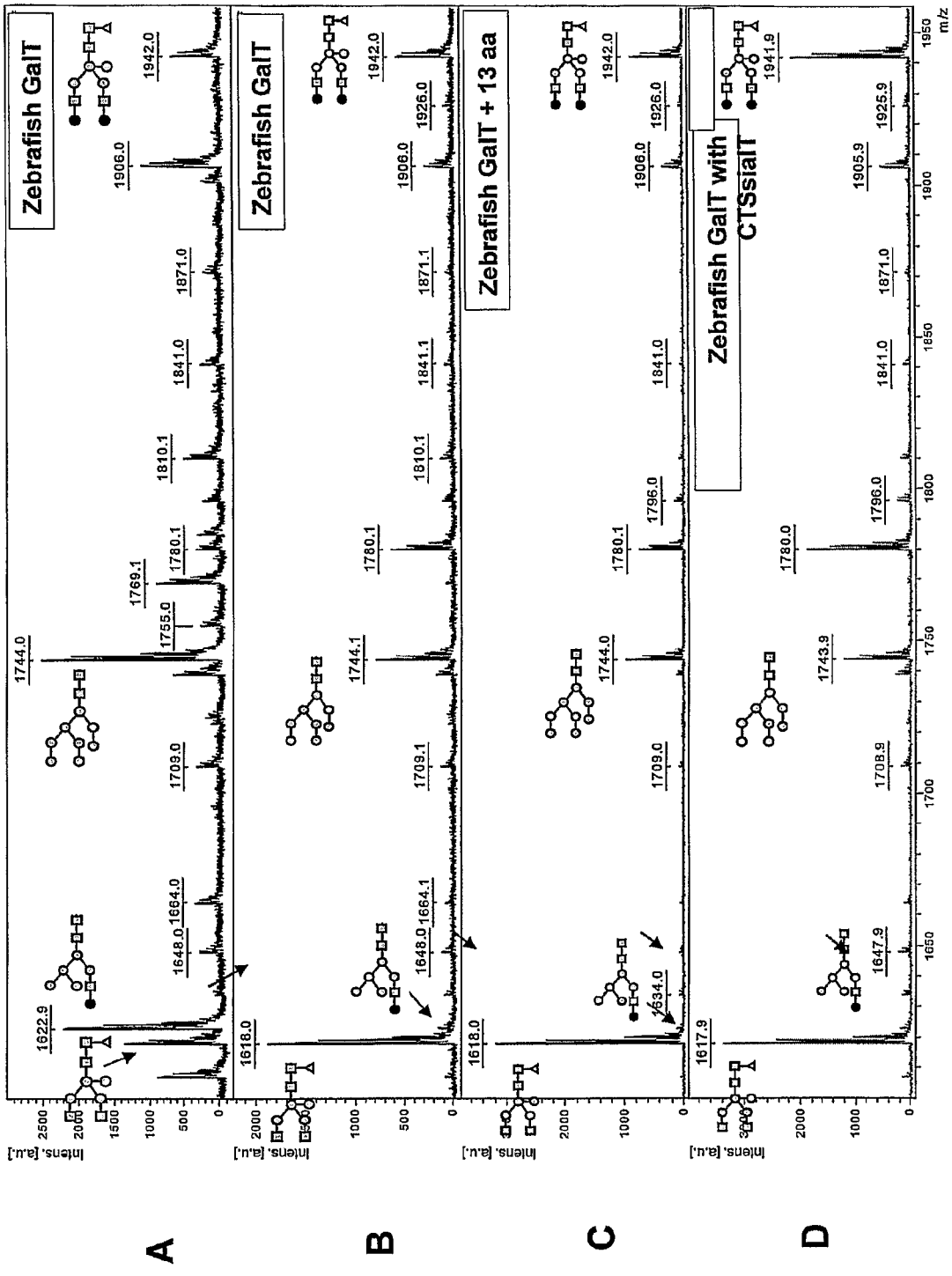
FIG. 3 depicts results from Maldi-TOF analyses of N-glycans purified from transgenic plants expressing zebrafish GalT gene sequences. From top to bottom, normal zebrafish gene (zebrafish GalT, 2 plants), 13 amino acid N-terminus human GalT-zebrafish GalT, and SialT-CTS-zebrafish GalT.

Results from MALDI-TOF analyses, see FIG. 3 and summarized in FIG. 4, middle column and Table 3, of N-glycans purified from transgenic plants expressing the zebrafish GalT gene sequences show that expression of wild-type zebrafish GalT gene sequence results in some hybrid type galactosylated N-glycans but also fully bi-antennary N-glycans with two galactoses. Depending on the plant some plants only have galactosylated bi-antennary N-glycans upon expression of zebrafish wild-type GalT gene sequence (see FIG. 3, uppermost versus $2^{nd}$ from top panel). The amount of double galactosylated bi-antennary N-glycans can be significantly increased by either the 13 aminoacid N-terminus human GalT (HsDGal, SEQ ID NO:15) or SialT-CTS-GalT (sialDGal, SEQ ID NO:17), with the latter having highest amount of galactosylated bi-antennary N-glycans (see Table 3 and FIG. 4, bottom panel, middle column).

Remarkably, galactosylation of double-galactosylated bi-antennary N-glycans obtained through the expression of Sial-CTS-zebrafish GalT in tobacco is 50% increased in SialT-CTS-zebrafish GalT compared to SialT-CTS-human GalT (see Table 3 and FIG. 4, bottom panel, middle column and left column, respectively). The Sial-CTS-zebrafish GalT produces up to 45% of total N-glycans that have one or more galactose residues (see Table 3).

A high yield in total N-glycans that have one or more galactose residues such as it is seen in the bi-antennary N-glycans when Sial-CTS-zebrafish GalT is expressed in plants, is desirable when producing, for example, exogenous therapeutic glycoproteins. Table 1. Oligonucleotides used in Example 1 (5' to 3')

TABLE 1

| Oligonucleotides used in Example 1 (5' to 3') | |
|---|---|
| Name | Sequence |
| GgalLEEVAST | (SEQ ID NO: 22)<br>GTGACCTCGAGGAGGTGGCGAGCACAAACC |

TABLE 1-continued

Oligonucleotides used in Example 1 (5' to 3')

| Name | Sequence |
|---|---|
| GgGaldw | (SEQ ID NO: 23)<br>GTGACGGATCCTTCAGCTGCCGGGCGCTCCGATA |
| HsGgalstart | (SEQ ID NO: 24)<br>GTCAGGTCGACGAAGACAACATGAGGCTTCGGGAGCC<br>TCTCCTCAGCGGCAGCGCCGCT ATGAAGGAGCCAGC<br>CCT |
| GgGal142 | (SEQ ID NO: 25)<br>GTGACGGTCTCACATGACGCCACCTAGAAGTCCTGA |

TABLE 2

Oligonucleotides used in Example 2 (5' to 3')

| Name | Sequence |
|---|---|
| DrGalup | (SEQ ID NO: 26)<br>GTGACTCTAGAAGACAACATGCCGGACTCCACCGGGAACT |
| DrGaldw | (SEQ ID NO: 27)<br>GTGACGGATCCTTCAGGGTTTGCCCACGTCCA |
| DrGal160 | (SEQ ID NO: 28)<br>GTGACGAAGACAACATGCACAGGAAACTGGCGGAGC |
| HsDrup | (SEQ ID NO: 29)<br>GTGACTCTAGAAGACAACATGAGGCTTCGGGAGCCGCTCCT<br>GAGCGGCAGCGCCGCGATGCCGGACTCCACCG |

TABLE 3

Summary of results obtained from MALDI-TOF analysis.

| Construct | Line | 1617.5 | 1622.6 | 1941.7 | Total Galactose |
|---|---|---|---|---|---|
| Zebrafish GalT | D1 | 2.6 | 4.7 | 1.7 | 32.9 |
| Zebrafish GalT | D2 | 10.2 | 0.8 | 3.4 | 23.5 |
| Zebrafish GalT | D3 | 4.7 | 4.3 | 1.4 | 34.2 |
| Zebrafish GalT | D4 | 17.4 | 0.7 | 3.4 | 23.9 |
| Zebrafish GalT + 13 aa | HD1 | 18.8 | 0.5 | 5.9 | 25.2 |
| Zebrafish GalT + 13 aa | HD2 | 15.9 | 0.3 | 5.1 | 23.5 |
| Zebrafish GalT + 13 aa | HD4 | 24.5 | <0.1 | 4.5 | 30.1 |
| Zebrafish GalT with CTSsialT | SDa | 11.9 | 0.5 | 9.1 | 44.8 |
| Zebrafish GalT with CTSsialT | SDb | 13.6 | 0.4 | 7.6 | 29.4 |
| Zebrafish GalT with CTSsialT | SDc | 11.5 | 0.5 | 7.7 | 29.4 |
| Chicken GalT | Ga | ND | 11.2 | ND | 30.5 |
| Chicken GalT | Gb | ND | 15.7 | ND | 33.3 |
| Chicken GalT | Gc | ND | 11.8 | ND | 30.6 |
| Chicken GalT + 13 aa | HG1 | 2.1 | 5.6 | 0.8 | 31.4 |
| Chicken GalT + 13 aa | HG2 | 1.5 | 7.1 | 0.4 | 29.4 |
| Chicken GalT + 13 aa | HG4 | 3.7 | 3.6 | 1.1 | 26.9 |
| Chicken GalT + 13 aa | HG5 | 2.1 | 9 | <0.1 | 30.4 |
| Chicken GalT with CTSsialT | SG1 | 1.1 | 3.6 | 1.9 | 35.5 |
| Chicken GalT with CTSsialT | SG2 | 0.7 | 2.5 | 1.6 | 30.4 |

ND = not detected
Numbers are % total peak area for columns 3-5;
% total galactose is % of total N-glycans having one or more galactose residues (column 6).

SEQ GgGalhybr (SEQ ID NO: 1):
ATGAAGGAGCCAGCCCTCCCAGGTACATCACTTCAGAGGGCTTGCAGGCT

CCTCGTCGCTTTCTGTGCACTTCACCTCTCTGCAACTCTGCTCTACTACC

TCGCAGGTAGTTCTCTCACGCCACCTAGAAGTCCTGAACCTCCACCTAGA

CGACCACCTCCAGCTAACCTCTCTTCCACCATCTAGACCACCTCCTCC

ACCTGCTGCACGTCCACGACCTGGACCTGTTTCAGCACAACCACGTAACC

TCCCAGACTCTGCTCCATCTGGACTTTGTCCTGACCCTTCTCCACTTCTC

GTCGGACCACTTAGAGTTGAGTTCTCTCAGCCTGTGAACCTCGAGGAGGT

GGCGAGCACAAACCCTGAGGTCAGGGAGGGAGGTCGTTTTGCTCCAAAGG

ACTGCAAGGCGCTGCAGAAAGTAGCAATCATCATCCCGTTCCGAAACCGA

GAGGAGCATCTGAAGTACTGGCTCTATTACATGCACCCAATTCTTCAAAG

GCAGCAGCTAGATTATGGAGTGTATGTCATCAACCAGGATGGAGACGAAG

AATTTAACCGTGCTAAACTGCTGAATGTAGGATTCACGGAAGCTTTGAAG

GAGTATGACTATGACTGCTTTGTGTTTAGTGATGTAGACCTGATCCCAAT

GGATGACAGGAACACCTACAAGTGCTACAGCCAACCAAGGCACCTTTCTG

TCTCCATGGATAAATTCGGATTTCGGTTACCCTACAATCAGTATTTTGGA

GGTGTGTCTGCCTTGAGCAAAGAACAATTCACGAAGATCAATGGGTTCCC

AAACAATTACTGGGGCTGGGGAGGCGAAGATGATGACATCTACAACAGGC

TGGTGTTCAAAGGCATGGGCATATCTCGGCCAGATGCTGTCATTGGGAAA

TGCAGAATGATTCGCCACTCGCGTGATCGGAAGAACGAGCCCAACCCGGA

GAGGTTTGACCGTATTGCTCACACCAGGGAGACGATGAGCTCTGATGGCT

TGAACTCGCTCTCCTACGAGGTGCTAAGGACTGACAGGTTCCCTCTGTAC

ACGAGGATCACAGTGGATATCGGAGCGCCCGGCAGCTGA

SEQ Ggal (SEQ ID NO: 2):
MKEPALPGTSLQRACRLLVAFCALHLSATLLYYLAGSSLTPPRSPEPPPR

RPPPANLSLPPSRPPPPPAARPRPGPVSAQPRNLPDSAPSGLCPDPSPLL

VGPLRVEFSQPVNLEEVASTNPEVREGGRFAPKDCKALQKVAIIIPFRNR

EEHLKYWLYYMHPILQRQQLDYGVYVINQDGDEEFNRAKLLNVGFTEALK

EYDYDCFVFSDVDLIPMDDRNTYKCYSQPRHLSVSMDKFGFRLPYNQYFG

GVSALSKEQFTKINGFPNNYWGWGGEDDDIYNRLVFKGMGISRPDAVIGK

CRMIRHSRDRKNEPNPERFDRIAHTRETMSSDGLNSLSYEVLRTDRFPLY

TRITVDIGAPGS

SEQ GgGal114-362 (SEQ ID NO: 3):
CTCGAGGAGGTGGCGAGCACAAACCCTGAGGTCAGGGAGGGAGGTCGTTT
TGCTCCAAAGGACTGCAAGGCGCTGCAGAAAGTAGCAATCATCATCCCGT
TCCGAAACCGAGAGGAGCATCTGAAGTACTGGCTCTATTACATGCACCCA
ATTCTTCAAAGGCAGCAGCTAGATTATGGAGTGTATGTCATCAACCAGGA
TGGAGACGAAGAATTTAACCGTGCTAAACTGCTGAATGTAGGATTCACGG
AAGCTTTGAAGGAGTATGACTATGACTGCTTTGTGTTTAGTGATGTAGAC
CTGATCCCAATGGATGACAGGAACACCTACAAGTGCTACAGCCAACCAAG
GCACCTTTCTGTCTCCATGGATAAATTCGGATTTCGGTTACCCTACAATC
AGTATTTTGGAGGTGTGTCTGCCTTGAGCAAAGAACAATTCACGAAGATC
AATGGGTTTCCAAACAATTACTGGGGCTGGGGAGGCGAAGATGATGACAT
CTACAACAGGCTGGTGTTCAAAGGCATGGGCATATCTCGGCCAGATGCTG
TCATTGGGAAATGCAGAATGATTCGCCACTCGCGTGATCGGAAGAACGAG
CCCAACCCGGAGAGGTTTGACCGTATTGCTCACACCAGGGAGACGATGAG
CTCTGATGGCTTGAACTCGCTCTCCTACGAGGTGCTAAGGACTGACAGGT
TCCCTCTGTACACGAGGATCACAGTGGATATCGGAGCGCCCGGCAGCTGA

SEQ GgGal114-362 (SEQ ID NO: 4):
LEEVASTNPEVREGGRFAPKDCKALQKVAIIIPFRNREEHLKYWLYYMHP
ILQRQQLDYGVYVINQDGDEEFNRAKLLNVGFTEALKEYDYDCFVFSDVD
LIPMDDRNTYKCYSQPRHLSVSMDKFGFRLPYNQYFGGVSALSKEQFTKI
NGFPNNYWGWGGEDDDIYNRLVFKGMGISRPDAVIGKCRMIRHSRDRKNE
PNPERFDRIAHTRETMSSDGLNSLSYEVLRTDRFPLYTRITVDIGAPGS

SEQ CASeco (SEQ ID NO: 5):
GGCGCGCCTCGAGGCGATCGCAGATCTATCGATGCATGCCATGGTACCCG
GGAGCTCGAATTCTAGAAGCTTCTGCAGACGCGTCGACGTCATATGGATC
CGCGAGAGACCTCTTAATTAA SEQ GgGalsyn (SEQ ID NO: 6):
CTCGAGGAGACCGAAGACAACATGAAGGAGCCAGCCCTCCCAGGTACATC
ACTTCAGAGGGCTTGCAGGCTCCTCGTCGCTTTCTGTGCACTTCACCTCT
CTGCAACTCTGCTCTACTACCTCGCAGGTAGTTCTCTCACGCCACCTAGA
AGTCCTGAACCTCCACCTAGACGACCACCTCCAGCTAACCTCTCTCTTCC
ACCATCTAGACCACCTCCTCCACCTGCTGCACGTCCACGACCTGGACCTG
TTTCAGCACAACCACGTAACCTCCCAGACTCTGCTCCATCTGGACTTTGT
CCTGACCCTTCTCCACTTCTCGTCGGACCACTTAGAGTTGAGTTCTCTCA
GCCTGTGAACCTCGAG SEQ GgGalsyn (SEQ ID NO: 7):
MKEPALPGTSLQRACRLLVAFCALHLSATLLYYLAGSSLTPPRSPEPPPR
RPPPANLSLPPSRPPPPPAARPRPGPVSAQPRNLPDSAPSGLCPDPSPLL
VGPLRVEFSQPVNLE SEQ HsGgal (SEQ ID NO: 8):
ATGAGGCTTCGGAGCCTCTCCTCAGCGGCAGCGCCGCTATGAAGGAGCC
AGCCCTCCCAGGTACATCACTTCAGAGGGCTTGCAGGCTCCTCGTCGCTT
TCTGTGCACTTCACCTCTCTGCAACTCTGCTCTACTACCTCGCAGGTAGT
TCTCTCACGCCACCTAGAAGTCCTGAACCTCCACCTAGACGACCACCTCC
AGCTAACCTCTCTCTTCCACCATCTAGACCACCTCCTCCACCTGCTGCAC
GTCCACGACCTGGACCTGTTTCAGCACAACCACGTAACCTCCCAGACTCT
GCTCCATCTGGACTTTGTCCTGACCCTTCTCCACTTCTCGTCGGACCACT
TAGAGTTGAGTTCTCTCAGCCTGTGAACCTCGAGGAGGTGGCGAGCACAA
ACCCTGAGGTCAGGGAGGGAGGTCGTTTTGCTCCAAAGGACTGCAAGGCG
CTGCAGAAAGTAGCAATCATCATCCCGTTCCGAAACCGAGAGGAGCATCT
GAAGTACTGGCTCTATTACATGCACCCAATTCTTCAAAGGCAGCAGCTAG
ATTATGGAGTGTATGTCATCAACCAGGATGGAGACGAAGAATTTAACCGT
GCTAAACTGCTGAATGTAGGATTCACGGAAGCTTTGAAGGAGTATGACTA
TGACTGCTTTGTGTTTAGTGATGTAGACCTGATCCCAATGGATGACAGGA
ACACCTACAAGTGCTACAGCCAACCAAGGCACCTTTCTGTCTCCATGGAT
AAATTCGGATTTCGGTTACCCTACAATCAGTATTTTGGAGGTGTGTCTGC
CTTGAGCAAAGAACAATTCACGAAGATCAATGGGTTCCCAAACAATTACT
GGGGCTGGGGAGGCGAAGATGATGACATCTACAACAGGCTGGTGTTCAAA
GGCATGGGCATATCTCGGCCAGATGCTGTCATTGGGAAATGCAGAATGAT
TCGCCACTCGCGTGATCGGAAGAACGAGCCCAACCCGGAGAGGTTTGACC
GTATTGCTCACACCAGGGAGACGATGAGCTCTGATGGCTTGAACTCGCTC
TCCTACGAGGTGCTAAGGACTGACAGGTTCCCTCTGTACACGAGGATCAC
AGTGGATATCGGAGCGCCCGGCAGCTGA SEQ HsGgal (SEQ ID NO: 9):
MRLREPLLSGSAAMKEPALPGTSLQRACRLLVAFCALHLSATLLYYLAGS
SLTPPRSPEPPPRRPPPANLSLPPSRPPPPPAARPRPGPVSAQPRNLPDS
APSGLCPDPSPLLVGPLRVEFSQPVNLEEVASTNPEVREGGRFAPKDCKA
LQKVAIIIPFRNREEHLKYWLYYMHPILQRQQLDYGVYVINQDGDEEFNR
AKLLNVGFTEALKEYDYDCFVFSDVDLIPMDDRNTYKCYSQPRHLSVSMD
KFGFRLPYNQYFGGVSALSKEQFTKINGFPNNYWGWGGEDDDIYNRLVFK
GMGISRPDAVIGKCRMIRHSRDRKNEPNPERFDRIAHTRETMSSDGLNSL
SYEVLRTDRFPLYTRITVDIGAPGS SEQ sialGGal (SEQ ID NO: 10):
ATGATTCATACCAACTTGAAGAAAAGTTCAGCCTCTTCATCCTGGTCTT
TCTCCTGTTCGCAGTCATCTGTGTTTGGAAGAAAGGGAGCGACTATGAGG
CCCTTACACTGCAAGCCAAGGAGTTCCAGATGCCCAAGAGCCAGGAGAAA
GTGGCCATGACGCCACCTAGAAGTCCTGAACCTCCACCTAGACGACCACC
TCCAGCTAACCTCTCTCTTCCACCATCTAGACCACCTCCTCCACCTGCTG
CACGTCCACGACCTGGACCTGTTTCAGCACAACCACGTAACCTCCCAGAC
TCTGCTCCATCTGGACTTTGTCCTGACCCTTCTCCACTTCTCGTCGGACC
ACTTAGAGTTGAGTTCTCTCAGCCTGTGAACCTCGAGGAGGTGGCGAGCA
CAAACCCTGAGGTCAGGGAGGGAGGTCGTTTTGCTCCAAAGGACTGCAAG
GCGCTGCAGAAAGTAGCAATCATCATCCCGTTCCGAAACCGAGAGGAGCA
TCTGAAGTACTGGCTCTATTACATGCACCCAATTCTTCAAAGGCAGCAGC
TAGATTATGGAGTGTATGTCATCAACCAGGATGGAGACGAAGAATTTAAC -continued

```
CGTGCTAAACTGCTGAATGTAGGATTCACGGAAGCTTTGAAGGAGTATGA
CTATGACTGCTTTGTGTTTAGTGATGTAGACCTGATCCCAATGGATGACA
GGAACACCTACAAGTGCTACAGCCAACCAAGGCACCTTTCTGTCTCCATG
GATAAATTCGGATTTCGGTTACCCTACAATCAGTATTTTGGAGGTGTGTC
TGCCTTGAGCAAAGAACAATTCACGAAGATCAATGGGTTTCCAAACAATT
ACTGGGGCTGGGGAGGCGAAGATGATGACATCTACAACAGGCTGGTGTTC
AAAGGCATGGGCATATCTCGGCCAGATGCTGTCATTGGGAAATGCAGAAT
GATTCGCCACTCGCGTGATCGGAAGAACGAGCCCAACCCGGAGAGGTTTG
ACCGTATTGCTCACACCAGGGAGACGATGAGCTCTGATGGCTTGAACTCG
CTCTCCTACGAGGTGCTAAGGACTGACAGGTTCCCTCTGTACACGAGGAT
CACAGTGGATATCGGAGCGCCCGGCAGCTGA
```

SEQ sialGGal (SEQ ID NO: 11):
```
MIHTNLKKKFSLFILVFLLFAVICVWKKGSDYEALTLQAKEFQMPKSQEK
VAMTPPRSPEPPPRRPPPANLSLPPSRPPPPPAARPRPGPVSAQPRNLPD
SAPSGLCPDPSPLLVGPLRVEFSQPVNLEEVASTNPEVREGGRFAPKDCK
ALQKVAIIPFRNREEHLKYWLYYMHPILQRQQLDYGVYVINQDGDEEFN
RAKLLNVGFTEALKEYDYDCFVFSDVDLIPMDDRNTYKCYSQPRHLSVSM
DKFGFRLPYNQYFGGVSALSKEQFTKINGFPNNYWGWGGEDDDIYNRLVF
KGMGISRPDAVIGKCRMIRHSRDRKNEPNPERFDRIAHTRETMSSDGLNS
LSYEVLRTDRFPLYTRITVDIGAPGS
```

SEQ RAP40 (SEQ ID NO: 12):
```
GGCGCGCCAAGCTTGAATTAATTCTACTCCAAAAATATCAAAGATACAGT
CTCAGAAGACCAAAGGGCAATTGAGACTTTTCAACAAAGGGTAATATCCG
GAAACCTCCTCGGATTCCATTGCCCAGCTATCTGTCACTTTATTGTGAAG
ATAGTGGAAAAGGAAGGTGGCTCCTACAAATGCCATCATTGCGATAAAGG
AAAGGCCATCGTTGAAGATGCCTCTGCCGACAGTGGTCCCAAAGATGGAC
CCCCACCCACGAGGAGCATCGTGGAAAAAGAAGACGTTCCAACCACGTCT
TCAAAGCAAGTGGATTGATGTGATAATTCCGCATGGAGTCAAAGATTCAA
ATAGAGGACCTAACAGAACTCGCCGTAAAGACTGGCGAACAGTTCATACA
GAGTCTCTTACGACTCAATGACAAGAAGAAAATCTTCGTCAACATGGTGG
AGCACGACACACTTGTCTACTCCAAAAATATCAAAGATACAGTCTCAGAA
GACCAAAGGGCAATTGAGACTTTTCAACAAAGGGTAATATCCGGAAACCT
CCTCGGATTCCATTGCCCAGCTATCTGTCACTTTATTGTGAAGATAGTGG
AAAAGGAAGGTGGCTCCTACAAATGCCATCATTGCGATAAAGGAAAGGCC
ATCGTTGAAGATGCCTCTGCCGACAGTGGTCCCAAAGATGGACCCCCACC
CACGAGGAGCATCGTGGAAAAAGAAGACGTTCCAACCACGTCTTCAAAGC
AAGTGGATTGATGTGATATCTCCACTGACGTAAGGGATGACGCACAATCC
CACTATCCTTCGCAAGACCCTTCCTCTATATAAGGAAGTTCATTTCATTT
GGAGAGGGTTTTTATTTTTAATTTTCTTTCAAATACTTCCACCATGGGCG
AGCTCGGTACCCGGGGATCCCCGGGTACCGAGCTCGAATTTCCCGATCG
TTCAAACATTTGGCAATAAAGTTTCTTAAGATTGAATCCTGTTGCCGGTC
TTGCGATGATTATCATATAATTTCTGTTGAATTACGTTAAGCATGTAATA
ATTAACATGTAATGCATGACGTTATTTATGAGATGGGTTTTTATGATTAG
AGTCCCGCAATTATACATTTAATACGCGATAGAAAACAAAATATAGCGCG
CAAACTAGGATAAATTATCGCGCGCGGTGTCATCTATGTTACTAGATCGG
GAATTCCAGATCTGCGGCCGCTTAATTAA
```

SEQ Dgal (SEQ ID NO: 13):
```
TCTAGAAGACAACATGCCGGACTCCACCGGGAACTTCAGCCTCCTGCAGC
GGACCTGCTCTCTGGTGGTGCTGCTGTGCTTCTTACACATCTTTGTCACC
GTCATTTACTACATGAGGAACTCGGACTCTCGGCCAGCCTTCGCCCAGAA
CCAGCAGCAGAGACCGACGATACACAGGAAACTGGCGGAGCAGAGGGGCA
CCACTGAGGACAGCAGACCCGCGGCCAACGCCTCGAGCAACGGCCAGGAG
CTGCAGATCTGCCCAGAGGAGCCGCCGCGCCTGGTGGGTCCTCTGCGTGT
GGAGTTCTCAGACCCGATCACGTTAGAAATGGTGCGGACAGAGAACAGTG
TTCTGCAAGAGGGCGGACGCTTCAGACCCCCAGACTGCATAGCTCGGCAG
AAGGTGGCCATGATCATCCCCTTCCGGAACCGAGACGAGCACCTGAAGTT
CTGGCTCTATTACCTGCACCCCATCCTGCAGCGCCAACAGCTCGACTACG
GCGTCTACGTCATCAACCAGGATGGCGAGGACACGTTTAATCGAGCTAAA
CTCCTGAACATCGGCTATGCGGAGGCGCTGAAGGAGTACGATTACGACTG
TTTTGTGTTCAGCGACGTGGACCTGATCCCGATGGATGACCGCAACATCT
ACAAGTGCTACAATCAGCCCAGACACCTGGCCGTCTCCATGGACAAGTTC
GGCTTCAGGCTGCCGTACACACAGTATTTCGGTGGCGTTTCGTCGCTCAG
CAAAGAGCAGTTCCTGAAGATCAACGGATTCCCCAACAACTACTGGGGCT
GGGGCGGAGAGGACGACGACATCTTCAACAGGATCTCCTCCAGAGGGATG
TCGATATCTAGGCCTGACGGACTCCTGGGTCGCTGTAGGATGATCCGGCA
TGAGAGAGACAAGCAGAACGACCCAAACCCTCAAAGATTTGACCGAATCG
CGCACACAAGGGAAACCATGGCAACTGATGGGATCAATTCGCTAAAATAT
AACGTGGTAAAAATCGAGAAAGACCTGCTCTTCACCAAAATCACAGTGGA
CGTGGGCAAACCCTGA
```

SEQ Dgal (SEQ ID NO: 14):
```
MPDSTGNFSLLQRTCSLVVLLCFLHIFVTVIYYMRNSDSRPAFAQNQQQR
PTIHRKLAEQRGTTEDSRPAANASSNGQELQICPEEPPRLVGPLRVEFSD
PITLEMVRTENSVLQEGGRFRPPDCIARQKVAMIIPFRNRDEHLKFWLYY
LHPILQRQQLDYGVYVINQDGEDTFNRAKLLNIGYAEALKEYDYDCFVFS
DVDLIPMDDRNIYKCYNQPRHLAVSMDKFGFRLPYTQYFGGVSSLSKEQF
LKINGFPNNYWGWGGEDDDIFNRISSRGMSISRPDGLLGRCMIRHERDK
QNDPNPQRFDRIAHTRETMATDGINSLKYNVVKIEKDLLFTKITVDVGKP
```

SEQ HsDGal (SEQ ID NO: 15):
```
TCTAGAAGACAACATGAGGCTTCGGGAGCCGCTCCTGAGCGGCAGCGCCG
CGATGCCGGACTCCACCGGGAACTTCAGCCTCCTGCAGCGGACCTGCTCT
CTGGTGGTGCTGCTGTGCTTCTTACACATCTTTGTCACCGTCATTTACTA
CATGAGGAACTCGGACTCTCGGCCAGCCTTCGCCCAGAACCAGCAGCAGA
GACCGACGATACACAGGAAACTGGCGGAGCAGAGGGGCACCACTGAGGAC
```

```
AGCAGACCCGCGGCCAACGCCTCGAGCAACGGCCAGGAGCTGCAGATCTG
CCCAGAGGAGCCGCCGCGCCTGGTGGGTCCTCTGCGTGTGGAGTTCTCAG
ACCCGATCACGTTAGAAATGGTGCGGACAGAGAACAGTGTTCTGCAAGAG
GGCGGACGCTTCAGACCCCCAGACTGCATAGCTCGGCAGAAGGTGGCCAT
GATCATCCCCTTCCGGAACCGAGACGAGCACCTGAAGTTCTGGCTCTATT
ACCTGCACCCCATCCTGCAGCGCCAACAGCTCGACTACGGCGTCTACGTC
ATCAACCAGGATGGCGAGGACACGTTTAATCGAGCTAAACTCCTGAACAT
CGGCTATGCGGAGGCGCTGAAGGAGTACGATTACGACTGTTTTGTGTTCA
GCGACGTGGACCTGATCCCGATGGATGACCGCAACATCTACAAGTGCTAC
AATCAGCCCAGACACCTGGCCGTCTCCATGGACAAGTTCGGCTTCAGGCT
GCCGTACACACAGTATTTCGGTGGCGTTTCGTCGCTCAGCAAAGAGCAGT
TCCTGAAGATCAACGGATTCCCCAACAACTACTGGGGCTGGGGCGGAGAG
GACGACGACATCTTCAACAGGATCTCCTCCAGAGGGATGTCGATATCTAG
GCCTGACGGACTCCTGGGTCGCTGTAGGATGATCCGGCATGAGAGAGACA
AGCAGAACGACCCAAACCCTCAAAGATTTGACCGAATCGCGCACACAAGG
GAAACCATGGCAACTGATGGGATCAATTCGCTAAAATATAACGTGGTAAA
AATCGAGAAAGACCTGCTCTTCACCAAAATCACAGTGGACGTGGGCAAAC
CCTGA
```

SEQ HsDGal (SEQ ID NO: 16):
MRLREPLLSGSAAMPDSTGNFSLLQRTCSLVVLLCFLHIFVTVIYYMRNS
DSRPAFAQNQQQRPTIHRKLAEQRGTTEDSRPAANASSNGQELQICPEEP
PRLVGPLRVEFSDPITLEMVRTENSVLQEGGRFRPPDCIARQKVAMIIPF
RNRDEHLKFWLYYLHPILQRQQLDYGVYVINQDGEDTFNRAKLLNIGYAE
ALKEYDYDCFVFSDVDLIPMDDRNIYKCYNQPRHLAVSMDKFGFRLPYTQ
YFGGVSSLSKEQFLKINGFPNNYWGWGGEDDDIFNRISSRGMSISRPDGL
LGRCRMIRHERDKQNDPNPQRFDRIAHTRETMATDGINSLKYNVVKIEKD
LLFTKITVDVGKP

SEQ sialDGal (SEQ ID NO: 17):
ATGATTCATACCAACTTGAAGAAAAAGTTCAGCCTCTTCATCCTGGTCTT
TCTCCTGTTCGCAGTCATCTGTGTTTGGAAGAAAGGGAGCGACTATGAGG
CCCTTACACTGCAAGCCAAGGAGTTCCAGATGCCCAAGAGCCAGGAGAAA
GTGGCCATGCACAGGAAACTGGCGGAGCAGAGGGGCACCACTGAGGACAG
CAGACCCGCGGCCAACGCCTCGAGCAACGGCCAGGAGCTGCAGATCTGCC
CAGAGGAGCCGCCGCGCCTGGTGGGTCCTCTGCGTGTGGAGTTCTCAGAC CCGATCACGTTAGAAATGGTGCGGACAGAGAACAGTGTTCTGCAAGAGGG
CGGACGCTTCAGACCCCCAGACTGCATAGCTCGGCAGAAGGTGGCCATGA
TCATCCCCTTCCGGAACCGAGACGAGCACCTGAAGTTCTGGCTCTATTAC
CTGCACCCCATCCTGCAGCGCCAACAGCTCGACTACGGCGTCTACGTCAT
CAACCAGGATGGCGAGGACACGTTTAATCGAGCTAAACTCCTGAACATCG
GCTATGCGGAGGCGCTGAAGGAGTACGATTACGACTGTTTTGTGTTCAGC
GACGTGGACCTGATCCCGATGGATGACCGCAACATCTACAAGTGCTACAA
TCAGCCCAGACACCTGGCCGTCTCCATGGACAAGTTCGGCTTCAGGCTGC
CGTACACACAGTATTTCGGTGGCGTTTCGTCGCTCAGCAAAGAGCAGTTC
CTGAAGATCAACGGATTCCCCAACAACTACTGGGGCTGGGGCGGAGAGGA
CGACGACATCTTCAACAGGATCTCCTCCAGAGGGATGTCGATATCTAGGC
CTGACGGACTCCTGGGTCGCTGTAGGATGATCCGGCATGAGAGAGACAAG
CAGAACGACCCAAACCCTCAAAGATTTGACCGAATCGCGCACACAAGGGA
AACCATGGCAACTGATGGGATCAATTCGCTAAAATATAACGTGGTAAAAA
TCGAGAAAGACCTGCTCTTCACCAAAATCACAGTGGACGTGGGCAAACCC
TGA SEQ sialDGal (SEQ ID NO: 18):
MIHTNLKKKFSLFILVFLLFAVICVWKKGSDYEALTLQAKEFQMPKSQEK
VAMHRKLAEQRGTTEDSRPAANASSNGQELQICPEEPPRLVGPLRVEFSD
PITLEMVRTENSVLQEGGRFRPPDCIARQKVAMIIPFRNRDEHLKFWLYY
LHPILQRQQLDYGVYVINQDGEDTFNRAKLLNIGYAEALKEYDYDCFVFS
DVDLIPMDDRNIYKCYNQPRHLAVSMDKFGFRLPYTQYFGGVSSLSKEQF
LKINGFPNNYWGWGGEDDDIFNRISSRGMSISRPDGLLGRCRMIRHERDK
QNDPNPQRFDRIAHTRETMATDGINSLKYNVVKIEKDLLFTKITVDVGKP SEQ CTS sialT (SEQ ID NO: 19):
ATGATTCATACCAACTTGAAGAAAAAGTTCAGCCTCTTCATCCTGGTCTT
TCTCCTGTTCGCAGTCATCTGTGTTTGGAAGAAAGGGAGCGACTATGAGG
CCCTTACACTGCAAGCCAAGGAATTCCAGATGCCCAAGAGCCAGGAGAAA
GTGGCCATG SEQ CTS sialT (SEQ ID NO: 20):
MIHTNLKKKFSLFILVFLLFAVICVWKKGSDYEALTLQAKEFQMPKSQEK
VAM N-terminal 13 amino acid residues, human β-1,4-
galactosyltransferase 1 (SEQ ID NO: 21)
<u>MRLREPLLSGSAA</u>

---

What is claimed is:

1. A method of producing a transgenic plant system which is capable of adding galactose residues in β1,4-linkage to N-linked glycans, comprising:

(a) inserting a nucleic acid molecule that encodes a non-mammalian β1,4-galactosyltransferase comprising an amino acid sequence identical to the active domain of SEQ ID NO:2 into a plant system, which is a whole plant, a part thereof, or a plant cell; wherein the active domain comprises amino acids 40-362 of SEQ ID NO:2, and wherein the galactosyltransferase further comprises a golgi localization signal sequence; and (b) selecting a transgenic plant system that has taken up the nucleic acid molecule of (a) and expresses the nucleic acid molecule, thereby producing a transgenic plant system capable of adding galactose residues in β1,4-linkage to N-linked glycans.

2. The method of claim 1, wherein the nucleic acid molecule encodes SEQ ID NO: 2, SEQ ID NO:9, or SEQ ID NO:11.

3. The method of claim 1, wherein the non-mammalian β1,4-galactosyltransferase is extended at the N-terminus with an amino acid sequence of about 10-20 amino acids in length corresponding to the N-terminal amino acid sequence of a mammalian β1,4-galactosyltransferase.

4. The method of claim 3, wherein the N-terminal amino acid sequence comprises at least the sequence [K/R]-X-[K/R] in the first 10 N-terminal amino acids, wherein [K/R] represents either a lysine or arginine residue and X can be any amino acid.

5. The method of claim 4, wherein the amino acid sequence is MRLREPLLSGSAA (SEQ ID NO: 21).

6. The method of claim 1, wherein the golgi localization signal sequence comprises the cytoplasmic-transmembrane-stem region (CTS) of a mammalian sialyltransferase.

7. The method of claim 1, wherein the golgi localization signal sequence comprises the cytoplasmic-transmembrane-stem region (CTS) of a plant Golgi-localized protein.

8. The method of claim 1, wherein the transgenic plant or transgenic plant cell produces a glycoprotein comprising hybrid-type N-linked glycans lacking both β1,2-xylose and α1,3-fucose residues.

9. The method of claim 8, wherein the amount of hybrid-type N-linked glycans lacking both β1,2-xylose and α1,3-fucose residues produced is at least twice the amount produced by a plant cell or plant expressing wild-type human β1,4-galactosyltransferase.

10. A transgenic plant system, comprising a nucleic acid molecule encoding a non-mammalian β1,4-galactosyltransferase comprising an amino acid sequence identical to the active domain of SEQ ID NO:2, wherein the active domain comprises amino acids 40-362 of SEQ ID NO:2, and wherein the galactosyltransferase further comprises a golgi localization signal sequence; and wherein the non-mammalian β1,4-galactosyltransferase adds galactose residues in a β1,4-linkage to N-linked glycans in the transgenic plant system, and wherein the transgenic plant system is a whole plant, a part of a plant, or a plant cell.

11. The transgenic plant system of claim 10, which is a part of a plant selected from the group consisting of seed, embryo, callus tissue, leaves, root, shoot, pollen, and microspore.

12. The transgenic plant system of claim 10, which is a transgenic plant cell.

13. The transgenic plant system of claim 12, wherein the transgenic plant cell is grown in suspension culture.

14. The transgenic plant system of claim 13, wherein the transgenic plant cell grown in suspension culture is selected from the group consisting of *N. tabacum* BY2, *Daucus carota* and *Arabidopsis thaliana* cell suspension.

15. The transgenic plant system of claim 13, wherein the transgenic plant cell is from a moss selected from the group consisting of *Bryophytaea, Physcomitrella patens, Funaria hygrometrica*, and *Ceratodon purpureus*.

16. A method of producing a heterologous glycoprotein comprising one or more hybrid-type galactosylated N-linked glycans, comprising:
(a) inserting into a plant system a nucleic acid molecule encoding a heterologous glycoprotein, and a nucleic acid molecule encoding a non-mammalian β1,4-galactosyltransferase comprising an amino acid sequence identical to the active domain of SEQ ID NO:2, wherein the active domain comprises amino acids 40-362 of SEQ ID NO:2, and wherein the galactosyltransferase further comprises a golgi localization signal sequence thereby producing a transgenic plant system, wherein the plant system is a whole plant, a part of a plant, or a plant cell; and
(b) maintaining the transgenic plant system under conditions appropriate for expression of the nucleic acid molecules, whereby a heterologous glycoprotein comprising one or more hybrid-type galactosylated N-linked glycans is produced.

17. The method of claim 16, wherein the non-mammalian β1,4-galactosyltransferase is extended at the N-terminus with an amino acid sequence of about 10-20 amino acids in length corresponding to the N-terminal amino acid sequence of a mammalian β1,4-galactosyltransferase.

18. The method of claim 16, wherein the heterologous glycoprotein is a hormone; a cytokine, a vaccine; an adhesion molecule, an antibody or a functional antibody fragment.

19. The transgenic plant system of claim 10, wherein the non-mammalian β1,4-galactosyltransferase comprises at the N-terminus a mammalian β1,4-galactosyltransferase N-terminal amino acid sequence, which is about 10-20 amino acids in length and comprises at least the sequence [K/R]-X-[K/R] in the first 10 N-terminal amino acids, wherein [K/R] represents either a lysine or arginine residue and X can be any amino acid.

20. The transgenic plant system of claim 19, wherein the mammalian β1,4-galactosyltransferase N-terminal amino acid sequence is MRLREPLLSGSAA (SEQ ID NO: 21).

21. The transgenic plant system of claim 10, wherein the non-mammalian β1,4-galactosyltransferase comprises a cytoplasmic-transmembrane-stem region (CTS) derived from a mammalian sialyltransferase.

22. The transgenic plant of claim 21, wherein the CTS derived from the mammalian sialyltransferase comprises the amino acid sequence of SEQ ID NO:20.

23. The transgenic plant system of claim 10, wherein the non-mammalian β1,4-galactosyltransferase comprises the amino acid sequence of SEQ ID NO:2, SEQ ID NO:9, or SEQ ID NO:11.

* * * * *

SEQUENCE LISTING

<160> NUMBER OF SEQ ID NOS: 43

<210> SEQ ID NO 1
<211> LENGTH: 1089
<212> TYPE: DNA
<213> ORGANISM: Gallus gallus
<220> FEATURE:
<221> NAME/KEY: CDS
<222> LOCATION: (1)..(1089)

<400> SEQUENCE: 1

| | | | | | | | | | | | | | | | | |
|---|---|---|---|---|---|---|---|---|---|---|---|---|---|---|---|---|
| atg | aag | gag | cca | gcc | ctc | cca | ggt | aca | tca | ctt | cag | agg | gct | tgc | agg | 48 |
| Met | Lys | Glu | Pro | Ala | Leu | Pro | Gly | Thr | Ser | Leu | Gln | Arg | Ala | Cys | Arg | |
| 1 | | | | 5 | | | | | 10 | | | | | 15 | | |

| ctc | ctc | gtc | gct | ttc | tgt | gca | ctt | cac | ctc | tct | gca | act | ctg | ctc | tac | 96 |
|---|---|---|---|---|---|---|---|---|---|---|---|---|---|---|---|---|
| Leu | Leu | Val | Ala | Phe | Cys | Ala | Leu | His | Leu | Ser | Ala | Thr | Leu | Leu | Tyr | |
| | | | 20 | | | | | 25 | | | | | 30 | | | |

| tac | ctc | gca | ggt | agt | tct | ctc | acg | cca | cct | aga | agt | cct | gaa | cct | cca | 144 |
|---|---|---|---|---|---|---|---|---|---|---|---|---|---|---|---|---|
| Tyr | Leu | Ala | Gly | Ser | Ser | Leu | Thr | Pro | Pro | Arg | Ser | Pro | Glu | Pro | Pro | |
| | | 35 | | | | | 40 | | | | | 45 | | | | |

| cct | aga | cga | cca | cct | cca | gct | aac | ctc | tct | ctt | cca | cca | tct | aga | cca | 192 |
|---|---|---|---|---|---|---|---|---|---|---|---|---|---|---|---|---|
| Pro | Arg | Arg | Pro | Pro | Pro | Ala | Asn | Leu | Ser | Leu | Pro | Pro | Ser | Arg | Pro | |
| 50 | | | | | 55 | | | | | 60 | | | | | | |

| cct | cct | cca | cct | gct | gca | cgt | cca | cga | cct | gga | cct | gtt | tca | gca | caa | 240 |
|---|---|---|---|---|---|---|---|---|---|---|---|---|---|---|---|---|
| Pro | Pro | Pro | Pro | Ala | Ala | Arg | Pro | Arg | Pro | Gly | Pro | Val | Ser | Ala | Gln | |
| 65 | | | | 70 | | | | | 75 | | | | | 80 | | |

| cca | cgt | aac | ctc | cca | gac | tct | gct | cca | tct | gga | ctt | tgt | cct | gac | cct | 288 |
|---|---|---|---|---|---|---|---|---|---|---|---|---|---|---|---|---|
| Pro | Arg | Asn | Leu | Pro | Asp | Ser | Ala | Pro | Ser | Gly | Leu | Cys | Pro | Asp | Pro | |
| | | | | 85 | | | | | 90 | | | | | 95 | | |

| tct | cca | ctt | ctc | gtc | gga | cca | ctt | aga | gtt | gag | ttc | tct | cag | cct | gtg | 336 |
|---|---|---|---|---|---|---|---|---|---|---|---|---|---|---|---|---|
| Ser | Pro | Leu | Leu | Val | Gly | Pro | Leu | Arg | Val | Glu | Phe | Ser | Gln | Pro | Val | |
| | | | 100 | | | | | 105 | | | | | 110 | | | |

| aac | ctc | gag | gag | gtg | gcg | agc | aca | aac | cct | gag | gtc | agg | gag | gga | ggt | 384 |
|---|---|---|---|---|---|---|---|---|---|---|---|---|---|---|---|---|
| Asn | Leu | Glu | Glu | Val | Ala | Ser | Thr | Asn | Pro | Glu | Val | Arg | Glu | Gly | Gly | |
| | | 115 | | | | | 120 | | | | | 125 | | | | |

| cgt | ttt | gct | cca | aag | gac | tgc | aag | gcg | ctg | cag | aaa | gta | gca | atc | atc | 432 |
|---|---|---|---|---|---|---|---|---|---|---|---|---|---|---|---|---|
| Arg | Phe | Ala | Pro | Lys | Asp | Cys | Lys | Ala | Leu | Gln | Lys | Val | Ala | Ile | Ile | |
| | 130 | | | | | 135 | | | | | 140 | | | | | |

| atc | ccg | ttc | cga | aac | cga | gag | gag | cat | ctg | aag | tac | tgg | ctc | tat | tac | 480 |
|---|---|---|---|---|---|---|---|---|---|---|---|---|---|---|---|---|
| Ile | Pro | Phe | Arg | Asn | Arg | Glu | Glu | His | Leu | Lys | Tyr | Trp | Leu | Tyr | Tyr | |
| 145 | | | | | 150 | | | | | 155 | | | | | 160 | |

| atg | cac | cca | att | ctt | caa | agg | cag | cag | cta | gat | tat | gga | gtg | tat | gtc | 528 |
|---|---|---|---|---|---|---|---|---|---|---|---|---|---|---|---|---|
| Met | His | Pro | Ile | Leu | Gln | Arg | Gln | Gln | Leu | Asp | Tyr | Gly | Val | Tyr | Val | |
| | | | | 165 | | | | | 170 | | | | | 175 | | |

| atc | aac | cag | gat | gga | gac | gaa | gaa | ttt | aac | cgt | gct | aaa | ctg | ctg | aat | 576 |
|---|---|---|---|---|---|---|---|---|---|---|---|---|---|---|---|---|
| Ile | Asn | Gln | Asp | Gly | Asp | Glu | Glu | Phe | Asn | Arg | Ala | Lys | Leu | Leu | Asn | |
| | | | 180 | | | | | 185 | | | | | 190 | | | |

| gta | gga | ttc | acg | gaa | gct | ttg | aag | gag | tat | gac | tat | gac | tgc | ttt | gtg | 624 |
|---|---|---|---|---|---|---|---|---|---|---|---|---|---|---|---|---|
| Val | Gly | Phe | Thr | Glu | Ala | Leu | Lys | Glu | Tyr | Asp | Tyr | Asp | Cys | Phe | Val | |
| | | 195 | | | | | 200 | | | | | 205 | | | | |

| ttt | agt | gat | gta | gac | ctg | atc | cca | atg | gat | gac | agg | aac | acc | tac | aag | 672 |
|---|---|---|---|---|---|---|---|---|---|---|---|---|---|---|---|---|
| Phe | Ser | Asp | Val | Asp | Leu | Ile | Pro | Met | Asp | Asp | Arg | Asn | Thr | Tyr | Lys | |
| | 210 | | | | | 215 | | | | | 220 | | | | | |

| tgc | tac | agc | caa | cca | agg | cac | ctt | tct | gtc | tcc | atg | gat | aaa | ttc | gga | 720 |
|---|---|---|---|---|---|---|---|---|---|---|---|---|---|---|---|---|
| Cys | Tyr | Ser | Gln | Pro | Arg | His | Leu | Ser | Val | Ser | Met | Asp | Lys | Phe | Gly | |
| 225 | | | | | 230 | | | | | 235 | | | | | 240 | |

| ttt | cgg | tta | ccc | tac | aat | cag | tat | ttt | gga | ggt | gtg | tct | gcc | ttg | agc | 768 |
|---|---|---|---|---|---|---|---|---|---|---|---|---|---|---|---|---|
| Phe | Arg | Leu | Pro | Tyr | Asn | Gln | Tyr | Phe | Gly | Gly | Val | Ser | Ala | Leu | Ser | |
| | | | | 245 | | | | | 250 | | | | | 255 | | |

| aaa | gaa | caa | ttc | acg | aag | atc | aat | ggg | ttc | cca | aac | aat | tac | tgg | ggc | 816 |
|---|---|---|---|---|---|---|---|---|---|---|---|---|---|---|---|---|
| Lys | Glu | Gln | Phe | Thr | Lys | Ile | Asn | Gly | Phe | Pro | Asn | Asn | Tyr | Trp | Gly | |
| | | | 260 | | | | | 265 | | | | | 270 | | | |

| tgg | gga | ggc | gaa | gat | gat | gac | atc | tac | aac | agg | ctg | gtg | ttc | aaa | ggc | 864 |
|---|---|---|---|---|---|---|---|---|---|---|---|---|---|---|---|---|
| Trp | Gly | Gly | Glu | Asp | Asp | Asp | Ile | Tyr | Asn | Arg | Leu | Val | Phe | Lys | Gly | |
| | | 275 | | | | | 280 | | | | | 285 | | | | |

| atg | ggc | ata | tct | cgg | cca | gat | gct | gtc | att | ggg | aaa | tgc | aga | atg | att | 912 |
|---|---|---|---|---|---|---|---|---|---|---|---|---|---|---|---|---|
| Met | Gly | Ile | Ser | Arg | Pro | Asp | Ala | Val | Ile | Gly | Lys | Cys | Arg | Met | Ile | |
| | 290 | | | | | 295 | | | | | 300 | | | | | |

| | | | | | | | | | | | | | | |
|---|---|---|---|---|---|---|---|---|---|---|---|---|---|---|
| cgc | cac | tcg | cgt | gat | cgg | aag | aac | gag | ccc | aac | ccg | gag | agg | ttt gac | 960 |
| Arg | His | Ser | Arg | Asp | Arg | Lys | Asn | Glu | Pro | Asn | Pro | Glu | Arg | Phe Asp |
| 305 | | | | 310 | | | | | 315 | | | | | 320 |

| cgt | att | gct | cac | acc | agg | gag | acg | atg | agc | tct | gat | ggc | ttg | aac tcg | 1008 |
| Arg | Ile | Ala | His | Thr | Arg | Glu | Thr | Met | Ser | Ser | Asp | Gly | Leu | Asn Ser |
| | | | 325 | | | | | 330 | | | | | 335 | |

| ctc | tcc | tac | gag | gtg | cta | agg | act | gac | agg | ttc | cct | ctg | tac | acg agg | 1056 |
| Leu | Ser | Tyr | Glu | Val | Leu | Arg | Thr | Asp | Arg | Phe | Pro | Leu | Tyr | Thr Arg |
| | | | 340 | | | | | 345 | | | | | 350 | |

| atc | aca | gtg | gat | atc | gga | gcg | ccc | ggc | agc | tga | | | | | 1089 |
| Ile | Thr | Val | Asp | Ile | Gly | Ala | Pro | Gly | Ser | | | | | |
| | | 355 | | | | | 360 | | | | | | | |

<210> SEQ ID NO 2
<211> LENGTH: 362
<212> TYPE: PRT
<213> ORGANISM: Gallus gallus

<400> SEQUENCE: 2

Met Lys Glu Pro Ala Leu Pro Gly Thr Ser Leu Gln Arg Ala Cys Arg
1               5                   10                  15

Leu Leu Val Ala Phe Cys Ala Leu His Leu Ser Ala Thr Leu Leu Tyr
            20                  25                  30

Tyr Leu Ala Gly Ser Ser Leu Thr Pro Pro Arg Ser Pro Glu Pro Pro
        35                  40                  45

Pro Arg Arg Pro Pro Pro Ala Asn Leu Ser Leu Pro Pro Ser Arg Pro
    50                  55                  60

Pro Pro Pro Pro Ala Ala Arg Pro Arg Pro Gly Pro Val Ser Ala Gln
65                  70                  75                  80

Pro Arg Asn Leu Pro Asp Ser Ala Pro Ser Gly Leu Cys Pro Asp Pro
                85                  90                  95

Ser Pro Leu Leu Val Gly Pro Leu Arg Val Glu Phe Ser Gln Pro Val
            100                 105                 110

Asn Leu Glu Glu Val Ala Ser Thr Asn Pro Glu Val Arg Glu Gly Gly
        115                 120                 125

Arg Phe Ala Pro Lys Asp Cys Lys Ala Leu Gln Lys Val Ala Ile Ile
    130                 135                 140

Ile Pro Phe Arg Asn Arg Glu Glu His Leu Lys Tyr Trp Leu Tyr Tyr
145                 150                 155                 160

Met His Pro Ile Leu Gln Arg Gln Gln Leu Asp Tyr Gly Val Tyr Val
                165                 170                 175

Ile Asn Gln Asp Gly Asp Glu Glu Phe Asn Arg Ala Lys Leu Leu Asn
            180                 185                 190

Val Gly Phe Thr Glu Ala Leu Lys Glu Tyr Asp Tyr Asp Cys Phe Val
        195                 200                 205

Phe Ser Asp Val Asp Leu Ile Pro Met Asp Asp Arg Asn Thr Tyr Lys
    210                 215                 220

Cys Tyr Ser Gln Pro Arg His Leu Ser Val Ser Met Asp Lys Phe Gly
225                 230                 235                 240

Phe Arg Leu Pro Tyr Asn Gln Tyr Phe Gly Gly Val Ser Ala Leu Ser
                245                 250                 255

Lys Glu Gln Phe Thr Lys Ile Asn Gly Phe Pro Asn Asn Tyr Trp Gly
            260                 265                 270

Trp Gly Gly Glu Asp Asp Asp Ile Tyr Asn Arg Leu Val Phe Lys Gly
        275                 280                 285

Met Gly Ile Ser Arg Pro Asp Ala Val Ile Gly Lys Cys Arg Met Ile

```
                    290                 295                 300
Arg His Ser Arg Asp Arg Lys Asn Glu Pro Asn Pro Glu Arg Phe Asp
305                 310                 315                 320

Arg Ile Ala His Thr Arg Glu Thr Met Ser Ser Asp Gly Leu Asn Ser
                325                 330                 335

Leu Ser Tyr Glu Val Leu Arg Thr Asp Arg Phe Pro Leu Tyr Thr Arg
            340                 345                 350

Ile Thr Val Asp Ile Gly Ala Pro Gly Ser
            355                 360

<210> SEQ ID NO 3
<211> LENGTH: 750
<212> TYPE: DNA
<213> ORGANISM: Gallus gallus
<220> FEATURE:
<221> NAME/KEY: CDS
<222> LOCATION: (1)..(750)

<400> SEQUENCE: 3 ctc gag gag gtg gcg agc aca aac cct gag gtc agg gag gga ggt cgt       48
Leu Glu Glu Val Ala Ser Thr Asn Pro Glu Val Arg Glu Gly Gly Arg
1               5                   10                  15 ttt gct cca aag gac tgc aag gcg ctg cag aaa gta gca atc atc atc       96
Phe Ala Pro Lys Asp Cys Lys Ala Leu Gln Lys Val Ala Ile Ile Ile
                20                  25                  30 ccg ttc cga aac cga gag gag cat ctg aag tac tgg ctc tat tac atg      144
Pro Phe Arg Asn Arg Glu Glu His Leu Lys Tyr Trp Leu Tyr Tyr Met
            35                  40                  45 cac cca att ctt caa agg cag cag cta gat tat gga gtg tat gtc atc      192
His Pro Ile Leu Gln Arg Gln Gln Leu Asp Tyr Gly Val Tyr Val Ile
        50                  55                  60 aac cag gat gga gac gaa gaa ttt aac cgt gct aaa ctg ctg aat gta      240
Asn Gln Asp Gly Asp Glu Glu Phe Asn Arg Ala Lys Leu Leu Asn Val
65              70                  75                  80 gga ttc acg gaa gct ttg aag gag tat gac tat gac tgc ttt gtg ttt      288
Gly Phe Thr Glu Ala Leu Lys Glu Tyr Asp Tyr Asp Cys Phe Val Phe
                85                  90                  95 agt gat gta gac ctg atc cca atg gat gac agg aac acc tac aag tgc      336
Ser Asp Val Asp Leu Ile Pro Met Asp Asp Arg Asn Thr Tyr Lys Cys
            100                 105                 110 tac agc caa cca agg cac ctt tct gtc tcc atg gat aaa ttc gga ttt      384
Tyr Ser Gln Pro Arg His Leu Ser Val Ser Met Asp Lys Phe Gly Phe
        115                 120                 125 cgg tta ccc tac aat cag tat ttt gga ggt gtg tct gcc ttg agc aaa      432
Arg Leu Pro Tyr Asn Gln Tyr Phe Gly Gly Val Ser Ala Leu Ser Lys
    130                 135                 140 gaa caa ttc acg aag atc aat ggg ttt cca aac aat tac tgg ggc tgg      480
Glu Gln Phe Thr Lys Ile Asn Gly Phe Pro Asn Asn Tyr Trp Gly Trp
145                 150                 155                 160 gga ggc gaa gat gat gac atc tac aac agg ctg gtg ttc aaa ggc atg      528
Gly Gly Glu Asp Asp Asp Ile Tyr Asn Arg Leu Val Phe Lys Gly Met
                165                 170                 175 ggc ata tct cgg cca gat gct gtc att ggg aaa tgc aga atg att cgc      576
Gly Ile Ser Arg Pro Asp Ala Val Ile Gly Lys Cys Arg Met Ile Arg
            180                 185                 190 cac tcg cgt gat cgg aag aac gag ccc aac ccg gag agg ttt gac cgt      624
His Ser Arg Asp Arg Lys Asn Glu Pro Asn Pro Glu Arg Phe Asp Arg
        195                 200                 205 att gct cac acc agg gag acg atg agc tct gat ggc ttg aac tcg ctc      672
Ile Ala His Thr Arg Glu Thr Met Ser Ser Asp Gly Leu Asn Ser Leu
```

```
                   210                 215                 220
tcc tac gag gtg cta agg act gac agg ttc cct ctg tac acg agg atc         720
Ser Tyr Glu Val Leu Arg Thr Asp Arg Phe Pro Leu Tyr Thr Arg Ile
225                 230                 235                 240 aca gtg gat atc gga gcg ccc ggc agc tga                                 750
Thr Val Asp Ile Gly Ala Pro Gly Ser
                245
```

<210> SEQ ID NO 4
<211> LENGTH: 249
<212> TYPE: PRT
<213> ORGANISM: Gallus gallus

<400> SEQUENCE: 4

```
Leu Glu Glu Val Ala Ser Thr Asn Pro Glu Val Arg Glu Gly Gly Arg
1               5                   10                  15

Phe Ala Pro Lys Asp Cys Lys Ala Leu Gln Lys Val Ala Ile Ile Ile
                20                  25                  30

Pro Phe Arg Asn Arg Glu Glu His Leu Lys Tyr Trp Leu Tyr Tyr Met
            35                  40                  45

His Pro Ile Leu Gln Arg Gln Gln Leu Asp Tyr Gly Val Tyr Val Ile
        50                  55                  60

Asn Gln Asp Gly Asp Glu Glu Phe Asn Arg Ala Lys Leu Leu Asn Val
65                  70                  75                  80

Gly Phe Thr Glu Ala Leu Lys Glu Tyr Asp Tyr Asp Cys Phe Val Phe
                85                  90                  95

Ser Asp Val Asp Leu Ile Pro Met Asp Asp Arg Asn Thr Tyr Lys Cys
            100                 105                 110

Tyr Ser Gln Pro Arg His Leu Ser Val Ser Met Asp Lys Phe Gly Phe
        115                 120                 125

Arg Leu Pro Tyr Asn Gln Tyr Phe Gly Gly Val Ser Ala Leu Ser Lys
130                 135                 140

Glu Gln Phe Thr Lys Ile Asn Gly Phe Pro Asn Asn Tyr Trp Gly Trp
145                 150                 155                 160

Gly Gly Glu Asp Asp Asp Ile Tyr Asn Arg Leu Val Phe Lys Gly Met
                165                 170                 175

Gly Ile Ser Arg Pro Asp Ala Val Ile Gly Lys Cys Arg Met Ile Arg
            180                 185                 190

His Ser Arg Asp Arg Lys Asn Glu Pro Asn Pro Glu Arg Phe Asp Arg
        195                 200                 205

Ile Ala His Thr Arg Glu Thr Met Ser Ser Asp Gly Leu Asn Ser Leu
210                 215                 220

Ser Tyr Glu Val Leu Arg Thr Asp Arg Phe Pro Leu Tyr Thr Arg Ile
225                 230                 235                 240

Thr Val Asp Ile Gly Ala Pro Gly Ser
                245
```

<210> SEQ ID NO 5
<211> LENGTH: 121
<212> TYPE: DNA
<213> ORGANISM: artificial sequence
<220> FEATURE:
<223> OTHER INFORMATION: synthetic oligonucleotide (CASeco)

<400> SEQUENCE: 5

```
ggcgcgcctc gaggcgatcg cagatctatc gatgcatgcc atggtacccg ggagctcgaa      60
ttctagaagc ttctgcagac gcgtcgacgt catatggatc cgcgagagac ctcttaatta    120
```

```
<210> SEQ ID NO 6
<211> LENGTH: 366
<212> TYPE: DNA
<213> ORGANISM: artificial sequence
<220> FEATURE:
<223> OTHER INFORMATION: synthetic oligonucleotide (GGa1 N-terminus)
<220> FEATURE:
<221> NAME/KEY: CDS
<222> LOCATION: (22)..(366)

<400> SEQUENCE: 6
ctcgaggaga ccgaagacaa c atg aag gag cca gcc ctc cca ggt aca tca         51
                        Met Lys Glu Pro Ala Leu Pro Gly Thr Ser
                          1               5                  10 ctt cag agg gct tgc agg ctc ctc gtc gct ttc tgt gca ctt cac ctc         99
Leu Gln Arg Ala Cys Arg Leu Leu Val Ala Phe Cys Ala Leu His Leu
              15                  20                  25 tct gca act ctg ctc tac tac ctc gca ggt agt tct ctc acg cca cct        147
Ser Ala Thr Leu Leu Tyr Tyr Leu Ala Gly Ser Ser Leu Thr Pro Pro
          30                  35                  40 aga agt cct gaa cct cca cct aga cga cca cct cca gct aac ctc tct        195
Arg Ser Pro Glu Pro Pro Pro Arg Arg Pro Pro Pro Ala Asn Leu Ser
      45                  50                  55 ctt cca cca tct aga cca cct cct cca cct gct gca cgt cca cga cct        243
Leu Pro Pro Ser Arg Pro Pro Pro Pro Pro Ala Ala Arg Pro Arg Pro
  60                  65                  70 gga cct gtt tca gca caa cca cgt aac ctc cca gac tct gct cca tct        291
Gly Pro Val Ser Ala Gln Pro Arg Asn Leu Pro Asp Ser Ala Pro Ser
75                  80                  85                  90 gga ctt tgt cct gac cct tct cca ctt ctc gtc gga cca ctt aga gtt        339
Gly Leu Cys Pro Asp Pro Ser Pro Leu Leu Val Gly Pro Leu Arg Val
                  95                 100                 105 gag ttc tct cag cct gtg aac ctc gag                                    366
Glu Phe Ser Gln Pro Val Asn Leu Glu
              110                 115

<210> SEQ ID NO 7
<211> LENGTH: 115
<212> TYPE: PRT
<213> ORGANISM: artificial sequence
<220> FEATURE:
<223> OTHER INFORMATION: synthetic peptide

<400> SEQUENCE: 7

Met Lys Glu Pro Ala Leu Pro Gly Thr Ser Leu Gln Arg Ala Cys Arg
  1               5                  10                  15

Leu Leu Val Ala Phe Cys Ala Leu His Leu Ser Ala Thr Leu Leu Tyr
              20                  25                  30

Tyr Leu Ala Gly Ser Ser Leu Thr Pro Pro Arg Ser Pro Glu Pro Pro
          35                  40                  45

Pro Arg Arg Pro Pro Pro Ala Asn Leu Ser Leu Pro Pro Ser Arg Pro
      50                  55                  60

Pro Pro Pro Ala Ala Arg Pro Arg Pro Gly Pro Val Ser Ala Gln
 65                  70                  75                  80

Pro Arg Asn Leu Pro Asp Ser Ala Pro Ser Gly Leu Cys Pro Asp Pro
              85                  90                  95

Ser Pro Leu Leu Val Gly Pro Leu Arg Val Glu Phe Ser Gln Pro Val
             100                 105                 110
```

Asn Leu Glu
    115

<210> SEQ ID NO 8
<211> LENGTH: 1128
<212> TYPE: DNA
<213> ORGANISM: artificial sequence
<220> FEATURE:
<223> OTHER INFORMATION: synthetic oligonucleotide (HsGGal)
<220> FEATURE:
<221> NAME/KEY: CDS
<222> LOCATION: (1)..(1128)

<400> SEQUENCE: 8

| | | |
|---|---|---|
| atg agg ctt cgg gag cct ctc ctc agc ggc agc gcc gct atg aag gag<br>Met Arg Leu Arg Glu Pro Leu Leu Ser Gly Ser Ala Ala Met Lys Glu<br>1               5                   10                  15 | | 48 |
| cca gcc ctc cca ggt aca tca ctt cag agg gct tgc agg ctc ctc gtc<br>Pro Ala Leu Pro Gly Thr Ser Leu Gln Arg Ala Cys Arg Leu Leu Val<br>            20                  25                  30 | | 96 |
| gct ttc tgt gca ctt cac ctc tct gca act ctg ctc tac tac ctc gca<br>Ala Phe Cys Ala Leu His Leu Ser Ala Thr Leu Leu Tyr Tyr Leu Ala<br>        35                  40                  45 | | 144 |
| ggt agt tct ctc acg cca cct aga agt cct gaa cct cca cct aga cga<br>Gly Ser Ser Leu Thr Pro Pro Arg Ser Pro Glu Pro Pro Pro Arg Arg<br>    50                  55                  60 | | 192 |
| cca cct cca gct aac ctc tct ctt cca cca tct aga cca cct cct cca<br>Pro Pro Pro Ala Asn Leu Ser Leu Pro Pro Ser Arg Pro Pro Pro Pro<br>65                  70                  75                  80 | | 240 |
| cct gct gca cgt cca cga cct gga cct gtt tca gca caa cca cgt aac<br>Pro Ala Ala Arg Pro Arg Pro Gly Pro Val Ser Ala Gln Pro Arg Asn<br>                85                  90                  95 | | 288 |
| ctc cca gac tct gct cca tct gga ctt tgt cct gac cct tct cca ctt<br>Leu Pro Asp Ser Ala Pro Ser Gly Leu Cys Pro Asp Pro Ser Pro Leu<br>            100                 105                 110 | | 336 |
| ctc gtc gga cca ctt aga gtt gag ttc tct cag cct gtg aac ctc gag<br>Leu Val Gly Pro Leu Arg Val Glu Phe Ser Gln Pro Val Asn Leu Glu<br>        115                 120                 125 | | 384 |
| gag gtg gcg agc aca aac cct gag gtc agg gag gga ggt cgt ttt gct<br>Glu Val Ala Ser Thr Asn Pro Glu Val Arg Glu Gly Gly Arg Phe Ala<br>    130                 135                 140 | | 432 |
| cca aag gac tgc aag gcg ctg cag aaa gta gca atc atc ccg ttc<br>Pro Lys Asp Cys Lys Ala Leu Gln Lys Val Ala Ile Ile Pro Phe<br>145                 150                 155                 160 | | 480 |
| cga aac cga gag gag cat ctg aag tac tgg ctc tat tac atg cac cca<br>Arg Asn Arg Glu Glu His Leu Lys Tyr Trp Leu Tyr Tyr Met His Pro<br>                165                 170                 175 | | 528 |
| att ctt caa agg cag cag cta gat tat gga gtg tat gtc atc aac cag<br>Ile Leu Gln Arg Gln Gln Leu Asp Tyr Gly Val Tyr Val Ile Asn Gln<br>            180                 185                 190 | | 576 |
| gat gga gac gaa gaa ttt aac cgt gct aaa ctg ctg aat gta gga ttc<br>Asp Gly Asp Glu Glu Phe Asn Arg Ala Lys Leu Leu Asn Val Gly Phe<br>        195                 200                 205 | | 624 |
| acg gaa gct ttg aag gag tat gac tat gac tgc ttt gtg ttt agt gat<br>Thr Glu Ala Leu Lys Glu Tyr Asp Tyr Asp Cys Phe Val Phe Ser Asp<br>    210                 215                 220 | | 672 |
| gta gac ctg atc cca atg gat gac agg aac acc tac aag tgc tac agc<br>Val Asp Leu Ile Pro Met Asp Asp Arg Asn Thr Tyr Lys Cys Tyr Ser<br>225                 230                 235                 240 | | 720 |
| caa cca agg cac ctt tct gtc tcc atg gat aaa ttc gga ttt cgg tta<br>Gln Pro Arg His Leu Ser Val Ser Met Asp Lys Phe Gly Phe Arg Leu<br>                245                 250                 255 | | 768 |

-continued

```
ccc tac aat cag tat ttt gga ggt gtg tct gcc ttg agc aaa gaa caa      816
Pro Tyr Asn Gln Tyr Phe Gly Gly Val Ser Ala Leu Ser Lys Glu Gln
        260                 265                 270 ttc acg aag atc aat ggg ttc cca aac aat tac tgg ggc tgg gga ggc      864
Phe Thr Lys Ile Asn Gly Phe Pro Asn Asn Tyr Trp Gly Trp Gly Gly
    275                 280                 285 gaa gat gat gac atc tac aac agg ctg gtg ttc aaa ggc atg ggc ata      912
Glu Asp Asp Asp Ile Tyr Asn Arg Leu Val Phe Lys Gly Met Gly Ile
290                 295                 300 tct cgg cca gat gct gtc att ggg aaa tgc aga atg att cgc cac tcg      960
Ser Arg Pro Asp Ala Val Ile Gly Lys Cys Arg Met Ile Arg His Ser
305                 310                 315                 320 cgt gat cgg aag aac gag ccc aac ccg gag agg ttt gac cgt att gct     1008
Arg Asp Arg Lys Asn Glu Pro Asn Pro Glu Arg Phe Asp Arg Ile Ala
        325                 330                 335 cac acc agg gag acg atg agc tct gat ggc ttg aac tcg ctc tcc tac     1056
His Thr Arg Glu Thr Met Ser Ser Asp Gly Leu Asn Ser Leu Ser Tyr
    340                 345                 350 gag gtg cta agg act gac agg ttc cct ctg tac acg agg atc aca gtg     1104
Glu Val Leu Arg Thr Asp Arg Phe Pro Leu Tyr Thr Arg Ile Thr Val
355                 360                 365 gat atc gga gcg ccc ggc agc tga                                     1128
Asp Ile Gly Ala Pro Gly Ser
370                 375

<210> SEQ ID NO 9
<211> LENGTH: 375
<212> TYPE: PRT
<213> ORGANISM: artificial sequence
<220> FEATURE:
<223> OTHER INFORMATION: synthetic peptide

<400> SEQUENCE: 9

Met Arg Leu Arg Glu Pro Leu Leu Ser Gly Ser Ala Ala Met Lys Glu
1               5                   10                  15

Pro Ala Leu Pro Gly Thr Ser Leu Gln Arg Ala Cys Arg Leu Leu Val
            20                  25                  30

Ala Phe Cys Ala Leu His Leu Ser Ala Thr Leu Leu Tyr Tyr Leu Ala
        35                  40                  45

Gly Ser Ser Leu Thr Pro Pro Arg Ser Pro Glu Pro Pro Pro Arg Arg
    50                  55                  60

Pro Pro Pro Ala Asn Leu Ser Leu Pro Ser Arg Pro Pro Pro Pro Pro
65                  70                  75                  80

Pro Ala Ala Arg Pro Arg Pro Gly Pro Val Ser Ala Gln Pro Arg Asn
                85                  90                  95

Leu Pro Asp Ser Ala Pro Ser Gly Leu Cys Pro Asp Pro Ser Pro Leu
            100                 105                 110

Leu Val Gly Pro Leu Arg Val Glu Phe Ser Gln Pro Val Asn Leu Glu
        115                 120                 125

Glu Val Ala Ser Thr Asn Pro Glu Val Arg Glu Gly Gly Arg Phe Ala
    130                 135                 140

Pro Lys Asp Cys Lys Ala Leu Gln Lys Val Ala Ile Ile Pro Phe
145                 150                 155                 160

Arg Asn Arg Glu Glu His Leu Lys Tyr Trp Leu Tyr Met His Pro
                165                 170                 175

Ile Leu Gln Arg Gln Gln Leu Asp Tyr Gly Val Tyr Val Ile Asn Gln
            180                 185                 190
```

```
Asp Gly Asp Glu Glu Phe Asn Arg Ala Lys Leu Leu Asn Val Gly Phe
            195                 200                 205

Thr Glu Ala Leu Lys Glu Tyr Asp Tyr Asp Cys Phe Val Phe Ser Asp
    210                 215                 220

Val Asp Leu Ile Pro Met Asp Asp Arg Asn Thr Tyr Lys Cys Tyr Ser
225                 230                 235                 240

Gln Pro Arg His Leu Ser Val Ser Met Asp Lys Phe Gly Phe Arg Leu
                245                 250                 255

Pro Tyr Asn Gln Tyr Phe Gly Gly Val Ser Ala Leu Ser Lys Glu Gln
            260                 265                 270

Phe Thr Lys Ile Asn Gly Phe Pro Asn Asn Tyr Trp Gly Trp Gly Gly
    275                 280                 285

Glu Asp Asp Asp Ile Tyr Asn Arg Leu Val Phe Lys Gly Met Gly Ile
    290                 295                 300

Ser Arg Pro Asp Ala Val Ile Gly Lys Cys Arg Met Ile Arg His Ser
305                 310                 315                 320

Arg Asp Arg Lys Asn Glu Pro Asn Pro Glu Arg Phe Asp Arg Ile Ala
                325                 330                 335

His Thr Arg Glu Thr Met Ser Ser Asp Gly Leu Asn Ser Leu Ser Tyr
            340                 345                 350

Glu Val Leu Arg Thr Asp Arg Phe Pro Leu Tyr Thr Arg Ile Thr Val
                355                 360                 365

Asp Ile Gly Ala Pro Gly Ser
            370                 375

<210> SEQ ID NO 10
<211> LENGTH: 1131
<212> TYPE: DNA
<213> ORGANISM: artificial sequence
<220> FEATURE:
<223> OTHER INFORMATION: synthetic oligonucleotide (sialGGal)
<220> FEATURE:
<221> NAME/KEY: CDS
<222> LOCATION: (1)..(1131)

<400> SEQUENCE: 10 atg att cat acc aac ttg aag aaa aag ttc agc ctc ttc atc ctg gtc    48
Met Ile His Thr Asn Leu Lys Lys Lys Phe Ser Leu Phe Ile Leu Val
1               5                   10                  15 ttt ctc ctg ttc gca gtc atc tgt gtt tgg aag aaa ggg agc gac tat    96
Phe Leu Leu Phe Ala Val Ile Cys Val Trp Lys Lys Gly Ser Asp Tyr
                20                  25                  30 gag gcc ctt aca ctg caa gcc aag gag ttc cag atg ccc aag agc cag   144
Glu Ala Leu Thr Leu Gln Ala Lys Glu Phe Gln Met Pro Lys Ser Gln
            35                  40                  45 gag aaa gtg gcc atg acg cca cct aga agt cct gaa cct cca cct aga   192
Glu Lys Val Ala Met Thr Pro Pro Arg Ser Pro Glu Pro Pro Pro Arg
        50                  55                  60 cga cca cct cca gct aac ctc tct ctt cca cca tct aga cca cct cct   240
Arg Pro Pro Pro Ala Asn Leu Ser Leu Pro Pro Ser Arg Pro Pro Pro
65                  70                  75                  80 cca cct gct gca cgt cca cga cct gga cct gtt tca gca caa cca cgt   288
Pro Pro Ala Ala Arg Pro Arg Pro Gly Pro Val Ser Ala Gln Pro Arg
                85                  90                  95 aac ctc cca gac tct gct cca tct gga ctt tgt cct gac cct tct cca   336
Asn Leu Pro Asp Ser Ala Pro Ser Gly Leu Cys Pro Asp Pro Ser Pro
            100                 105                 110 ctt ctc gtc gga cca ctt aga gtt gag ttc tct cag cct gtg aac ctc   384
Leu Leu Val Gly Pro Leu Arg Val Glu Phe Ser Gln Pro Val Asn Leu
```

```
gag gag gtg gcg agc aca aac cct gag gtc agg gag gga ggt cgt ttt      432
Glu Glu Val Ala Ser Thr Asn Pro Glu Val Arg Glu Gly Gly Arg Phe
        130                 135                 140 gct cca aag gac tgc aag gcg ctg cag aaa gta gca atc atc atc ccg      480
Ala Pro Lys Asp Cys Lys Ala Leu Gln Lys Val Ala Ile Ile Ile Pro
145                 150                 155                 160 ttc cga aac cga gag gag cat ctg aag tac tgg ctc tat tac atg cac      528
Phe Arg Asn Arg Glu Glu His Leu Lys Tyr Trp Leu Tyr Tyr Met His
                165                 170                 175 cca att ctt caa agg cag cag cta gat tat gga gtg tat gtc atc aac      576
Pro Ile Leu Gln Arg Gln Gln Leu Asp Tyr Gly Val Tyr Val Ile Asn
            180                 185                 190 cag gat gga gac gaa gaa ttt aac cgt gct aaa ctg ctg aat gta gga      624
Gln Asp Gly Asp Glu Glu Phe Asn Arg Ala Lys Leu Leu Asn Val Gly
        195                 200                 205 ttc acg gaa gct ttg aag gag tat gac tat gac tgc ttt gtg ttt agt      672
Phe Thr Glu Ala Leu Lys Glu Tyr Asp Tyr Asp Cys Phe Val Phe Ser
    210                 215                 220 gat gta gac ctg atc cca atg gat gac agg aac acc tac aag tgc tac      720
Asp Val Asp Leu Ile Pro Met Asp Asp Arg Asn Thr Tyr Lys Cys Tyr
225                 230                 235                 240 agc caa cca agg cac ctt tct gtc tcc atg gat aaa ttc gga ttt cgg      768
Ser Gln Pro Arg His Leu Ser Val Ser Met Asp Lys Phe Gly Phe Arg
                245                 250                 255 tta ccc tac aat cag tat ttt gga ggt gtg tct gcc ttg agc aaa gaa      816
Leu Pro Tyr Asn Gln Tyr Phe Gly Gly Val Ser Ala Leu Ser Lys Glu
            260                 265                 270 caa ttc acg aag atc aat ggg ttt cca aac aat tac tgg ggc tgg gga      864
Gln Phe Thr Lys Ile Asn Gly Phe Pro Asn Asn Tyr Trp Gly Trp Gly
        275                 280                 285 ggc gaa gat gat gac atc tac aac agg ctg gtg ttc aaa ggc atg ggc      912
Gly Glu Asp Asp Asp Ile Tyr Asn Arg Leu Val Phe Lys Gly Met Gly
    290                 295                 300 ata tct cgg cca gat gct gtc att ggg aaa tgc aga atg att cgc cac      960
Ile Ser Arg Pro Asp Ala Val Ile Gly Lys Cys Arg Met Ile Arg His
305                 310                 315                 320 tcg cgt gat cgg aag aac gag ccc aac ccg gag agg ttt gac cgt att     1008
Ser Arg Asp Arg Lys Asn Glu Pro Asn Pro Glu Arg Phe Asp Arg Ile
                325                 330                 335 gct cac acc agg gag acg atg agc tct gat ggc ttg aac tcg ctc tcc     1056
Ala His Thr Arg Glu Thr Met Ser Ser Asp Gly Leu Asn Ser Leu Ser
            340                 345                 350 tac gag gtg cta agg act gac agg ttc cct ctg tac acg agg atc aca     1104
Tyr Glu Val Leu Arg Thr Asp Arg Phe Pro Leu Tyr Thr Arg Ile Thr
        355                 360                 365 gtg gat atc gga gcg ccc ggc agc tga                                  1131
Val Asp Ile Gly Ala Pro Gly Ser
        370                 375

<210> SEQ ID NO 11
<211> LENGTH: 376
<212> TYPE: PRT
<213> ORGANISM: artificial sequence
<220> FEATURE:
<223> OTHER INFORMATION: synthetic petide

<400> SEQUENCE: 11

Met Ile His Thr Asn Leu Lys Lys Lys Phe Ser Leu Phe Ile Leu Val
1               5                   10                  15
```

Phe Leu Leu Phe Ala Val Ile Cys Val Trp Lys Lys Gly Ser Asp Tyr
             20                  25                  30

Glu Ala Leu Thr Leu Gln Ala Lys Glu Phe Gln Met Pro Lys Ser Gln
         35                  40                  45

Glu Lys Val Ala Met Thr Pro Pro Arg Ser Pro Glu Pro Pro Pro Arg
     50                  55                  60

Arg Pro Pro Pro Ala Asn Leu Ser Leu Pro Ser Arg Pro Pro Pro
65                  70                  75                  80

Pro Pro Ala Ala Arg Pro Arg Pro Gly Pro Val Ser Ala Gln Pro Arg
             85                  90                  95

Asn Leu Pro Asp Ser Ala Pro Ser Gly Leu Cys Pro Asp Pro Ser Pro
            100                 105                 110

Leu Leu Val Gly Pro Leu Arg Val Glu Phe Ser Gln Pro Val Asn Leu
            115                 120                 125

Glu Glu Val Ala Ser Thr Asn Pro Glu Val Arg Glu Gly Gly Arg Phe
        130                 135                 140

Ala Pro Lys Asp Cys Lys Ala Leu Gln Lys Val Ala Ile Ile Ile Pro
145                 150                 155                 160

Phe Arg Asn Arg Glu Glu His Leu Lys Tyr Trp Leu Tyr Tyr Met His
                165                 170                 175

Pro Ile Leu Gln Arg Gln Gln Leu Asp Tyr Gly Val Tyr Val Ile Asn
            180                 185                 190

Gln Asp Gly Asp Glu Glu Phe Asn Arg Ala Lys Leu Leu Asn Val Gly
        195                 200                 205

Phe Thr Glu Ala Leu Lys Glu Tyr Asp Tyr Asp Cys Phe Val Phe Ser
210                 215                 220

Asp Val Asp Leu Ile Pro Met Asp Asp Arg Asn Thr Tyr Lys Cys Tyr
225                 230                 235                 240

Ser Gln Pro Arg His Leu Ser Val Ser Met Asp Lys Phe Gly Phe Arg
                245                 250                 255

Leu Pro Tyr Asn Gln Tyr Phe Gly Gly Val Ser Ala Leu Ser Lys Glu
            260                 265                 270

Gln Phe Thr Lys Ile Asn Gly Phe Pro Asn Asn Tyr Trp Gly Trp Gly
        275                 280                 285

Gly Glu Asp Asp Asp Ile Tyr Asn Arg Leu Val Phe Lys Gly Met Gly
    290                 295                 300

Ile Ser Arg Pro Asp Ala Val Ile Gly Lys Cys Arg Met Ile Arg His
305                 310                 315                 320

Ser Arg Asp Arg Lys Asn Glu Pro Asn Pro Glu Arg Phe Asp Arg Ile
                325                 330                 335

Ala His Thr Arg Glu Thr Met Ser Ser Asp Gly Leu Asn Ser Leu Ser
            340                 345                 350

Tyr Glu Val Leu Arg Thr Asp Arg Phe Pro Leu Tyr Thr Arg Ile Thr
        355                 360                 365

Val Asp Ile Gly Ala Pro Gly Ser
370                 375

<210> SEQ ID NO 12
<211> LENGTH: 1229
<212> TYPE: DNA
<213> ORGANISM: artificial sequence
<220> FEATURE:
<223> OTHER INFORMATION: synthetic oligonucleotide (cassette RAP40)

<400> SEQUENCE: 12

-continued

```
ggcgcgccaa gcttgaatta attctactcc aaaaatatca agatacagt  ctcagaagac      60 caaagggcaa ttgagacttt tcaacaaagg gtaatatccg gaaacctcct cggattccat     120
tgcccagcta tctgtcactt tattgtgaag atagtggaaa aggaaggtgg ctcctacaaa     180
tgccatcatt gcgataaagg aaaggccatc gttgaagatg cctctgccga cagtggtccc     240
aaagatggac ccccacccac gaggagcatc gtggaaaaag aagacgttcc aaccacgtct     300
tcaaagcaag tggattgatg tgataattcc gcatggagtc aaagattcaa atagaggacc     360
taacagaact cgccgtaaag actggcgaac agttcataca gagtctctta cgactcaatg     420
acaagaagaa aatcttcgtc aacatggtgg agcacgacac acttgtctac tccaaaaata     480
tcaaagatac agtctcagaa gaccaaaggg caattgagac ttttcaacaa agggtaatat     540
ccggaaacct cctcggattc cattgcccag ctatctgtca ctttattgtg aagatagtgg     600
aaaaggaagg tggctcctac aaatgccatc attgcgataa aggaaaggcc atcgttgaag     660
atgcctctgc cgacagtggt cccaaagatg acccccacc cacgaggagc atcgtggaaa     720
aagaagacgt tccaaccacg tcttcaaagc aagtggattg atgtgatatc tccactgacg     780
taagggatga cgcacaatcc cactatcctt cgcaagaccc ttcctctata taaggaagtt     840
catttcattt ggagagggtt tttattttta attttctttc aaatacttcc accatgggcg     900
agctcggtac ccggggatcc ccgggtaccg agctcgaatt ccccgatcg ttcaaacatt      960 tggcaataaa gtttcttaag attgaatcct gttgccggtc ttgcgatgat tatcatataa    1020
tttctgttga attacgttaa gcatgtaata attaacatgt aatgcatgac gttatttatg    1080
agatgggttt ttatgattag agtcccgcaa ttatacattt aatacgcgat agaaaacaaa    1140
atatagcgcg caaactagga taaattatcg cgcgcggtgt catctatgtt actagatcgg    1200
gaattccaga tctgcggccg cttaattaa                                       1229
```

<210> SEQ ID NO 13
<211> LENGTH: 1066
<212> TYPE: DNA
<213> ORGANISM: Danio rerio
<220> FEATURE:
<221> NAME/KEY: CDS
<222> LOCATION: (14)..(1066)

<400> SEQUENCE: 13

```
tctagaagac aac atg ccg gac tcc acc ggg aac ttc agc ctc ctg cag       49
           Met Pro Asp Ser Thr Gly Asn Phe Ser Leu Leu Gln
             1               5                  10 cgg acc tgc tct ctg gtg gtg ctg ctg tgc ttc tta cac atc ttt gtc      97
Arg Thr Cys Ser Leu Val Val Leu Leu Cys Phe Leu His Ile Phe Val
         15                  20                  25 acc gtc att tac tac atg agg aac tcg gac tct cgg cca gcc ttc gcc     145
Thr Val Ile Tyr Tyr Met Arg Asn Ser Asp Ser Arg Pro Ala Phe Ala
     30                  35                  40 cag aac cag cag cag aga ccg acg ata cac agg aaa ctg gcg gag cag     193
Gln Asn Gln Gln Gln Arg Pro Thr Ile His Arg Lys Leu Ala Glu Gln
 45                  50                  55                  60 agg ggc acc act gag gac agc aga ccc gcg gcc aac gcc tcg agc aac     241
Arg Gly Thr Thr Glu Asp Ser Arg Pro Ala Ala Asn Ala Ser Ser Asn
                 65                  70                  75 ggc cag gag ctg cag atc tgc cca gag gag ccg ccg cgc ctg gtg ggt     289
Gly Gln Glu Leu Gln Ile Cys Pro Glu Glu Pro Pro Arg Leu Val Gly
             80                  85                  90 cct ctg cgt gtg gag ttc tca gac ccg atc acg tta gaa atg gtg cgg     337
Pro Leu Arg Val Glu Phe Ser Asp Pro Ile Thr Leu Glu Met Val Arg
```

-continued

```
                    95                  100                 105
aca gag aac agt gtt ctg caa gag ggc gga cgc ttc aga ccc cca gac     385
Thr Glu Asn Ser Val Leu Gln Glu Gly Gly Arg Phe Arg Pro Pro Asp
    110                 115                 120 tgc ata gct cgg cag aag gtg gcc atg atc atc ccc ttc cgg aac cga     433
Cys Ile Ala Arg Gln Lys Val Ala Met Ile Ile Pro Phe Arg Asn Arg
125                 130                 135                 140 gac gag cac ctg aag ttc tgg ctc tat tac ctg cac ccc atc ctg cag     481
Asp Glu His Leu Lys Phe Trp Leu Tyr Tyr Leu His Pro Ile Leu Gln
            145                 150                 155 cgc caa cag ctc gac tac ggc gtc tac gtc atc aac cag gat ggc gag     529
Arg Gln Gln Leu Asp Tyr Gly Val Tyr Val Ile Asn Gln Asp Gly Glu
                160                 165                 170 gac acg ttt aat cga gct aaa ctc ctg aac atc ggc tat gcg gag gcg     577
Asp Thr Phe Asn Arg Ala Lys Leu Leu Asn Ile Gly Tyr Ala Glu Ala
        175                 180                 185 ctg aag gag tac gat tac gac tgt ttt gtg ttc agc gac gtg gac ctg     625
Leu Lys Glu Tyr Asp Tyr Asp Cys Phe Val Phe Ser Asp Val Asp Leu
    190                 195                 200 atc ccg atg gat gac cgc aac atc tac aag tgc tac aat cag ccc aga     673
Ile Pro Met Asp Asp Arg Asn Ile Tyr Lys Cys Tyr Asn Gln Pro Arg
205                 210                 215                 220 cac ctg gcc gtc tcc atg gac aag ttc ggc ttc agg ctg ccg tac aca     721
His Leu Ala Val Ser Met Asp Lys Phe Gly Phe Arg Leu Pro Tyr Thr
            225                 230                 235 cag tat ttc ggt ggc gtt tcg tcg ctc agc aaa gag cag ttc ctg aag     769
Gln Tyr Phe Gly Gly Val Ser Ser Leu Ser Lys Glu Gln Phe Leu Lys
                240                 245                 250 atc aac gga ttc ccc aac aac tac tgg ggc tgg ggc gga gag gac gac     817
Ile Asn Gly Phe Pro Asn Asn Tyr Trp Gly Trp Gly Gly Glu Asp Asp
        255                 260                 265 gac atc ttc aac agg atc tcc tcc aga ggg atg tcg ata tct agg cct     865
Asp Ile Phe Asn Arg Ile Ser Ser Arg Gly Met Ser Ile Ser Arg Pro
    270                 275                 280 gac gga ctc ctg ggt cgc tgt agg atg atc cgg cat gag aga gac aag     913
Asp Gly Leu Leu Gly Arg Cys Arg Met Ile Arg His Glu Arg Asp Lys
285                 290                 295                 300 cag aac gac cca aac cct caa aga ttt gac cga atc gcg cac aca agg     961
Gln Asn Asp Pro Asn Pro Gln Arg Phe Asp Arg Ile Ala His Thr Arg
            305                 310                 315 gaa acc atg gca act gat ggg atc aat tcg cta aaa tat aac gtg gta    1009
Glu Thr Met Ala Thr Asp Gly Ile Asn Ser Leu Lys Tyr Asn Val Val
                320                 325                 330 aaa atc gag aaa gac ctg ctc ttc acc aaa atc aca gtg gac gtg ggc    1057
Lys Ile Glu Lys Asp Leu Leu Phe Thr Lys Ile Thr Val Asp Val Gly
        335                 340                 345 aaa ccc tga                                                        1066
Lys Pro
    350
```

<210> SEQ ID NO 14
<211> LENGTH: 350
<212> TYPE: PRT
<213> ORGANISM: Danio rerio

<400> SEQUENCE: 14

```
Met Pro Asp Ser Thr Gly Asn Phe Ser Leu Leu Gln Arg Thr Cys Ser
1               5                   10                  15

Leu Val Val Leu Leu Cys Phe Leu His Ile Phe Val Thr Val Ile Tyr
            20                  25                  30
```

```
Tyr Met Arg Asn Ser Asp Ser Arg Pro Ala Phe Ala Gln Asn Gln Gln
        35                  40                  45

Gln Arg Pro Thr Ile His Arg Lys Leu Ala Glu Gln Arg Gly Thr Thr
 50                  55                  60

Glu Asp Ser Arg Pro Ala Ala Asn Ala Ser Ser Asn Gly Gln Glu Leu
 65                  70                  75                  80

Gln Ile Cys Pro Glu Glu Pro Pro Arg Leu Val Gly Pro Leu Arg Val
                 85                  90                  95

Glu Phe Ser Asp Pro Ile Thr Leu Glu Met Val Arg Thr Glu Asn Ser
            100                 105                 110

Val Leu Gln Glu Gly Gly Arg Phe Arg Pro Pro Asp Cys Ile Ala Arg
        115                 120                 125

Gln Lys Val Ala Met Ile Ile Pro Phe Arg Asn Arg Asp Glu His Leu
130                 135                 140

Lys Phe Trp Leu Tyr Tyr Leu His Pro Ile Leu Gln Arg Gln Gln Leu
145                 150                 155                 160

Asp Tyr Gly Val Tyr Val Ile Asn Gln Asp Gly Glu Asp Thr Phe Asn
                165                 170                 175

Arg Ala Lys Leu Leu Asn Ile Gly Tyr Ala Glu Ala Leu Lys Glu Tyr
            180                 185                 190

Asp Tyr Asp Cys Phe Val Phe Ser Asp Val Asp Leu Ile Pro Met Asp
        195                 200                 205

Asp Arg Asn Ile Tyr Lys Cys Tyr Asn Gln Pro Arg His Leu Ala Val
210                 215                 220

Ser Met Asp Lys Phe Gly Phe Arg Leu Pro Tyr Thr Gln Tyr Phe Gly
225                 230                 235                 240

Gly Val Ser Ser Leu Ser Lys Glu Gln Phe Leu Lys Ile Asn Gly Phe
                245                 250                 255

Pro Asn Asn Tyr Trp Gly Trp Gly Gly Glu Asp Asp Ile Phe Asn
            260                 265                 270

Arg Ile Ser Ser Arg Gly Met Ser Ile Ser Arg Pro Asp Gly Leu Leu
        275                 280                 285

Gly Arg Cys Arg Met Ile Arg His Glu Arg Asp Lys Gly Asn Asp Pro
290                 295                 300

Asn Pro Gln Arg Phe Asp Arg Ile Ala His Thr Arg Glu Thr Met Ala
305                 310                 315                 320

Thr Asp Gly Ile Asn Ser Leu Lys Tyr Asn Val Val Lys Ile Glu Lys
                325                 330                 335

Asp Leu Leu Phe Thr Lys Ile Thr Val Asp Val Gly Lys Pro
            340                 345                 350

<210> SEQ ID NO 15
<211> LENGTH: 1105
<212> TYPE: DNA
<213> ORGANISM: artificial sequnce
<220> FEATURE:
<223> OTHER INFORMATION: synthetic oligonucleotide (HsDGal)
<220> FEATURE:
<221> NAME/KEY: CDS
<222> LOCATION: (14)..(1105)

<400> SEQUENCE: 15
tctagaagac aac atg agg ctt cgg gag ccg ctc ctg agc ggc agc gcc      49
               Met Arg Leu Arg Glu Pro Leu Leu Ser Gly Ser Ala
                 1               5                  10 gcg atg ccg gac tcc acc ggg aac ttc agc ctc ctg cag cgg acc tgc     97
```

```
                Ala Met Pro Asp Ser Thr Gly Asn Phe Ser Leu Leu Gln Arg Thr Cys
                        15                  20                  25 tct ctg gtg gtg ctg ctg tgc ttc tta cac atc ttt gtc acc gtc att       145
Ser Leu Val Val Leu Leu Cys Phe Leu His Ile Phe Val Thr Val Ile
        30                  35                  40 tac tac atg agg aac tcg gac tct cgg cca gcc ttc gcc cag aac cag       193
Tyr Tyr Met Arg Asn Ser Asp Ser Arg Pro Ala Phe Ala Gln Asn Gln
45                  50                  55                  60 cag cag aga ccg acg ata cac agg aaa ctg gcg gag cag agg ggc acc       241
Gln Gln Arg Pro Thr Ile His Arg Lys Leu Ala Glu Gln Arg Gly Thr
                65                  70                  75 act gag gac agc aga ccc gcg gcc aac gcc tcg agc aac ggc cag gag       289
Thr Glu Asp Ser Arg Pro Ala Ala Asn Ala Ser Ser Asn Gly Gln Glu
        80                  85                  90 ctg cag atc tgc cca gag gag ccg ccg cgc ctg gtg ggt cct ctg cgt       337
Leu Gln Ile Cys Pro Glu Glu Pro Pro Arg Leu Val Gly Pro Leu Arg
                95                  100                 105 gtg gag ttc tca gac ccg atc acg tta gaa atg gtg cgg aca gag aac       385
Val Glu Phe Ser Asp Pro Ile Thr Leu Glu Met Val Arg Thr Glu Asn
        110                 115                 120 agt gtt ctg caa gag ggc gga cgc ttc aga ccc cca gac tgc ata gct       433
Ser Val Leu Gln Glu Gly Gly Arg Phe Arg Pro Pro Asp Cys Ile Ala
125                 130                 135                 140 cgg cag aag gtg gcc atg atc atc ccc ttc cgg aac␣cga gac gag cac       481
Arg Gln Lys Val Ala Met Ile Ile Pro Phe Arg Asn Arg Asp Glu His
                145                 150                 155 ctg aag ttc tgg ctc tat tac ctg cac ccc atc ctg cag cgc caa cag       529
Leu Lys Phe Trp Leu Tyr Tyr Leu His Pro Ile Leu Gln Arg Gln Gln
        160                 165                 170 ctc gac tac ggc gtc tac gtc atc aac cag gat ggc gag gac acg ttt       577
Leu Asp Tyr Gly Val Tyr Val Ile Asn Gln Asp Gly Glu Asp Thr Phe
                175                 180                 185 aat cga gct aaa ctc ctg aac atc ggc tat gcg gag gcg ctg aag gag       625
Asn Arg Ala Lys Leu Leu Asn Ile Gly Tyr Ala Glu Ala Leu Lys Glu
        190                 195                 200 tac gat tac gac tgt ttt gtg ttc agc gac gtg gac ctg atc ccg atg       673
Tyr Asp Tyr Asp Cys Phe Val Phe Ser Asp Val Asp Leu Ile Pro Met
205                 210                 215                 220 gat gac cgc aac atc tac aag tgc tac aat cag ccc aga cac ctg gcc       721
Asp Asp Arg Asn Ile Tyr Lys Cys Tyr Asn Gln Pro Arg His Leu Ala
                225                 230                 235 gtc tcc atg gac aag ttc ggc ttc agg ctg ccg tac aca cag tat ttc       769
Val Ser Met Asp Lys Phe Gly Phe Arg Leu Pro Tyr Thr Gln Tyr Phe
        240                 245                 250 ggt ggc gtt tcg tcg ctc agc aaa gag cag ttc ctg aag atc aac gga       817
Gly Gly Val Ser Ser Leu Ser Lys Glu Gln Phe Leu Lys Ile Asn Gly
                255                 260                 265 ttc ccc aac aac tac tgg ggc tgg ggc gga gag gac gac gac atc ttc       865
Phe Pro Asn Asn Tyr Trp Gly Trp Gly Gly Glu Asp Asp Asp Ile Phe
        270                 275                 280 aac agg atc tcc tcc aga ggg atg tcg ata tct agg cct gac gga ctc       913
Asn Arg Ile Ser Ser Arg Gly Met Ser Ile Ser Arg Pro Asp Gly Leu
285                 290                 295                 300 ctg ggt cgc tgt agg atg atc cgg cat gag aga gac aag cag aac gac       961
Leu Gly Arg Cys Arg Met Ile Arg His Glu Arg Asp Lys Gln Asn Asp
                305                 310                 315 cca aac cct caa aga ttt gac cga atc gcg cac aca agg gaa acc atg      1009
Pro Asn Pro Gln Arg Phe Asp Arg Ile Ala His Thr Arg Glu Thr Met
        320                 325                 330
```

```
gca act gat ggg atc aat tcg cta aaa tat aac gtg gta aaa atc gag    1057
Ala Thr Asp Gly Ile Asn Ser Leu Lys Tyr Asn Val Val Lys Ile Glu
            335                 340                 345 aaa gac ctg ctc ttc acc aaa atc aca gtg gac gtg ggc aaa ccc tga    1105
Lys Asp Leu Leu Phe Thr Lys Ile Thr Val Asp Val Gly Lys Pro
350                 355                 360
```

<210> SEQ ID NO 16
<211> LENGTH: 363
<212> TYPE: PRT
<213> ORGANISM: artificial sequence
<220> FEATURE:
<223> OTHER INFORMATION: synthetic peptide

<400> SEQUENCE: 16

```
Met Arg Leu Arg Glu Pro Leu Ser Gly Ser Ala Ala Met Pro Asp
1               5                   10                  15

Ser Thr Gly Asn Phe Ser Leu Leu Gln Arg Thr Cys Ser Leu Val Val
                20                  25                  30

Leu Leu Cys Phe Leu His Ile Phe Val Thr Val Ile Tyr Tyr Met Arg
            35                  40                  45

Asn Ser Asp Ser Arg Pro Ala Phe Ala Gln Asn Gln Gln Gln Arg Pro
50                  55                  60

Thr Ile His Arg Lys Leu Ala Glu Gln Arg Gly Thr Thr Glu Asp Ser
65                  70                  75                  80

Arg Pro Ala Ala Asn Ala Ser Ser Asn Gly Gln Glu Leu Gln Ile Cys
                85                  90                  95

Pro Glu Glu Pro Pro Arg Leu Val Gly Pro Leu Arg Val Glu Phe Ser
            100                 105                 110

Asp Pro Ile Thr Leu Glu Met Val Arg Thr Glu Asn Ser Val Leu Gln
        115                 120                 125

Glu Gly Gly Arg Phe Arg Pro Pro Asp Cys Ile Ala Arg Gln Lys Val
130                 135                 140

Ala Met Ile Ile Pro Phe Arg Asn Arg Asp Glu His Leu Lys Phe Trp
145                 150                 155                 160

Leu Tyr Tyr Leu His Pro Ile Leu Gln Arg Gln Gln Leu Asp Tyr Gly
                165                 170                 175

Val Tyr Val Ile Asn Gln Asp Gly Glu Asp Thr Phe Asn Arg Ala Lys
            180                 185                 190

Leu Leu Asn Ile Gly Tyr Ala Glu Ala Leu Lys Glu Tyr Asp Tyr Asp
        195                 200                 205

Cys Phe Val Phe Ser Asp Val Asp Leu Ile Pro Met Asp Asp Arg Asn
210                 215                 220

Ile Tyr Lys Cys Tyr Asn Gln Pro Arg His Leu Ala Val Ser Met Asp
225                 230                 235                 240

Lys Phe Gly Phe Arg Leu Pro Tyr Thr Gln Tyr Phe Gly Gly Val Ser
                245                 250                 255

Ser Leu Ser Lys Glu Gln Phe Leu Lys Ile Asn Gly Phe Pro Asn Asn
            260                 265                 270

Tyr Trp Gly Trp Gly Gly Glu Asp Asp Asp Ile Phe Asn Arg Ile Ser
        275                 280                 285

Ser Arg Gly Met Ser Ile Ser Arg Pro Asp Gly Leu Leu Gly Arg Cys
290                 295                 300

Arg Met Ile Arg His Glu Arg Asp Lys Gln Asn Asp Pro Asn Pro Gln
305                 310                 315                 320

Arg Phe Asp Arg Ile Ala His Thr Arg Glu Thr Met Ala Thr Asp Gly
```

```
                        325                 330                 335
        Ile Asn Ser Leu Lys Tyr Asn Val Val Lys Ile Glu Lys Asp Leu Leu
                    340                 345                 350

Phe Thr Lys Ile Thr Val Asp Val Gly Lys Pro
                    355                 360

<210> SEQ ID NO 17
<211> LENGTH: 1053
<212> TYPE: DNA
<213> ORGANISM: artificial sequence
<220> FEATURE:
<223> OTHER INFORMATION: synthetic oligonucleotide (sialDGal)
<220> FEATURE:
<221> NAME/KEY: CDS
<222> LOCATION: (1)..(1053)

<400> SEQUENCE: 17 atg att cat acc aac ttg aag aaa aag ttc agc ctc ttc atc ctg gtc        48
Met Ile His Thr Asn Leu Lys Lys Lys Phe Ser Leu Phe Ile Leu Val
1               5                   10                  15 ttt ctc ctg ttc gca gtc atc tgt gtt tgg aag aaa ggg agc gac tat        96
Phe Leu Leu Phe Ala Val Ile Cys Val Trp Lys Lys Gly Ser Asp Tyr
            20                  25                  30 gag gcc ctt aca ctg caa gcc aag gag ttc cag atg ccc aag agc cag       144
Glu Ala Leu Thr Leu Gln Ala Lys Glu Phe Gln Met Pro Lys Ser Gln
        35                  40                  45 gag aaa gtg gcc atg cac agg aaa ctg gcg gag cag agg ggc acc act       192
Glu Lys Val Ala Met His Arg Lys Leu Ala Glu Gln Arg Gly Thr Thr
    50                  55                  60 gag gac agc aga ccc gcg gcc aac gcc tcg agc aac ggc cag gag ctg       240
Glu Asp Ser Arg Pro Ala Ala Asn Ala Ser Ser Asn Gly Gln Glu Leu
65                  70                  75                  80 cag atc tgc cca gag gag ccg ccg cgc ctg gtg ggt cct ctg cgt gtg       288
Gln Ile Cys Pro Glu Glu Pro Pro Arg Leu Val Gly Pro Leu Arg Val
                85                  90                  95 gag ttc tca gac ccg atc acg tta gaa atg gtg cgg aca gag aac agt       336
Glu Phe Ser Asp Pro Ile Thr Leu Glu Met Val Arg Thr Glu Asn Ser
            100                 105                 110 gtt ctg caa gag ggc gga cgc ttc aga ccc cca gac tgc ata gct cgg       384
Val Leu Gln Glu Gly Gly Arg Phe Arg Pro Pro Asp Cys Ile Ala Arg
        115                 120                 125 cag aag gtg gcc atg atc atc ccc ttc cgg aac cga gac gag cac ctg       432
Gln Lys Val Ala Met Ile Ile Pro Phe Arg Asn Arg Asp Glu His Leu
    130                 135                 140 aag ttc tgg ctc tat tac ctg cac ccc atc ctg cag cgc caa cag ctc       480
Lys Phe Trp Leu Tyr Tyr Leu His Pro Ile Leu Gln Arg Gln Gln Leu
145                 150                 155                 160 gac tac ggc gtc tac gtc atc aac cag gat ggc gag gac acg ttt aat       528
Asp Tyr Gly Val Tyr Val Ile Asn Gln Asp Gly Glu Asp Thr Phe Asn
                165                 170                 175 cga gct aaa ctc ctg aac atc ggc tat gcg gag gcg ctg aag gag tac       576
Arg Ala Lys Leu Leu Asn Ile Gly Tyr Ala Glu Ala Leu Lys Glu Tyr
            180                 185                 190 gat tac gac tgt ttt gtg ttc agc gac gtg gac ctg atc ccg atg gat       624
Asp Tyr Asp Cys Phe Val Phe Ser Asp Val Asp Leu Ile Pro Met Asp
        195                 200                 205 gac cgc aac atc tac aag tgc tac aat cag ccc aga cac ctg gcc gtc       672
Asp Arg Asn Ile Tyr Lys Cys Tyr Asn Gln Pro Arg His Leu Ala Val
    210                 215                 220 tcc atg gac aag ttc ggc ttc agg ctg ccg tac aca cag tat ttc ggt       720
Ser Met Asp Lys Phe Gly Phe Arg Leu Pro Tyr Thr Gln Tyr Phe Gly
```

```
                225                 230                 235                 240
ggc gtt tcg tcg ctc agc aaa gag cag ttc ctg aag atc aac gga ttc        768
Gly Val Ser Ser Leu Ser Lys Glu Gln Phe Leu Lys Ile Asn Gly Phe
                    245                 250                 255 ccc aac aac tac tgg ggc tgg ggc gga gag gac gac gac atc ttc aac        816
Pro Asn Asn Tyr Trp Gly Trp Gly Gly Glu Asp Asp Asp Ile Phe Asn
                260                 265                 270 agg atc tcc tcc aga ggg atg tcg ata tct agg cct gac gga ctc ctg        864
Arg Ile Ser Ser Arg Gly Met Ser Ile Ser Arg Pro Asp Gly Leu Leu
            275                 280                 285 ggt cgc tgt agg atg atc cgg cat gag aga gac aag cag aac gac cca        912
Gly Arg Cys Arg Met Ile Arg His Glu Arg Asp Lys Gln Asn Asp Pro
        290                 295                 300 aac cct caa aga ttt gac cga atc gcg cac aca agg gaa acc atg gca        960
Asn Pro Gln Arg Phe Asp Arg Ile Ala His Thr Arg Glu Thr Met Ala
305                 310                 315                 320 act gat ggg atc aat tcg cta aaa tat aac gtg gta aaa atc gag aaa       1008
Thr Asp Gly Ile Asn Ser Leu Lys Tyr Asn Val Val Lys Ile Glu Lys
                    325                 330                 335 gac ctg ctc ttc acc aaa atc aca gtg gac gtg ggc aaa ccc tga           1053
Asp Leu Leu Phe Thr Lys Ile Thr Val Asp Val Gly Lys Pro
                340                 345                 350

<210> SEQ ID NO 18
<211> LENGTH: 350
<212> TYPE: PRT
<213> ORGANISM: artificial sequence
<220> FEATURE:
<223> OTHER INFORMATION: synthetic peptide

<400> SEQUENCE: 18

Met Ile His Thr Asn Leu Lys Lys Phe Ser Leu Phe Ile Leu Val
1               5                   10                  15

Phe Leu Leu Phe Ala Val Ile Cys Val Trp Lys Lys Gly Ser Asp Tyr
                20                  25                  30

Glu Ala Leu Thr Leu Gln Ala Lys Glu Phe Gln Met Pro Lys Ser Gln
            35                  40                  45

Glu Lys Val Ala Met His Arg Lys Leu Ala Glu Gln Arg Gly Thr Thr
        50                  55                  60

Glu Asp Ser Arg Pro Ala Ala Asn Ala Ser Ser Asn Gly Gln Glu Leu
65                  70                  75                  80

Gln Ile Cys Pro Glu Glu Pro Pro Arg Leu Val Gly Pro Leu Arg Val
                85                  90                  95

Glu Phe Ser Asp Pro Ile Thr Leu Glu Met Val Arg Thr Glu Asn Ser
            100                 105                 110

Val Leu Gln Glu Gly Gly Arg Phe Arg Pro Pro Asp Cys Ile Ala Arg
        115                 120                 125

Gln Lys Val Ala Met Ile Ile Pro Phe Arg Asn Arg Asp Glu His Leu
130                 135                 140

Lys Phe Trp Leu Tyr Tyr Leu His Pro Ile Leu Gln Arg Gln Gln Leu
145                 150                 155                 160

Asp Tyr Gly Val Tyr Val Ile Asn Gln Asp Gly Glu Asp Thr Phe Asn
                165                 170                 175

Arg Ala Lys Leu Leu Asn Ile Gly Tyr Ala Glu Ala Leu Lys Glu Tyr
            180                 185                 190

Asp Tyr Asp Cys Phe Val Phe Ser Asp Val Asp Leu Ile Pro Met Asp
        195                 200                 205
```

```
Asp Arg Asn Ile Tyr Lys Cys Tyr Asn Gln Pro Arg His Leu Ala Val
    210                 215                 220
Ser Met Asp Lys Phe Gly Phe Arg Leu Pro Tyr Thr Gln Tyr Phe Gly
225                 230                 235                 240
Gly Val Ser Ser Leu Ser Lys Glu Gln Phe Leu Lys Ile Asn Gly Phe
                245                 250                 255
Pro Asn Asn Tyr Trp Gly Trp Gly Glu Asp Asp Ile Phe Asn
            260                 265                 270
Arg Ile Ser Ser Arg Gly Met Ser Ile Ser Arg Pro Asp Gly Leu Leu
            275                 280                 285
Gly Arg Cys Arg Met Ile Arg His Glu Arg Asp Lys Gln Asn Asp Pro
290                 295                 300
Asn Pro Gln Arg Phe Asp Arg Ile Ala His Thr Arg Glu Thr Met Ala
305                 310                 315                 320
Thr Asp Gly Ile Asn Ser Leu Lys Tyr Asn Val Val Lys Ile Glu Lys
                325                 330                 335
Asp Leu Leu Phe Thr Lys Ile Thr Val Asp Val Gly Lys Pro
            340                 345                 350
```

<210> SEQ ID NO 19
<211> LENGTH: 159
<212> TYPE: DNA
<213> ORGANISM: artificial sequence
<220> FEATURE:
<223> OTHER INFORMATION: synthetic oligonucleotide (CTSsialT)
<220> FEATURE:
<221> NAME/KEY: CDS
<222> LOCATION: (1)..(159)

<400> SEQUENCE: 19

```
atg att cat acc aac ttg aag aaa aag ttc agc ctc ttc atc ctg gtc      48
Met Ile His Thr Asn Leu Lys Lys Lys Phe Ser Leu Phe Ile Leu Val
1               5                   10                  15 ttt ctc ctg ttc gca gtc atc tgt gtt tgg aag aaa ggg agc gac tat      96
Phe Leu Leu Phe Ala Val Ile Cys Val Trp Lys Lys Gly Ser Asp Tyr
                20                  25                  30 gag gcc ctt aca ctg caa gcc aag gaa ttc cag atg ccc aag agc cag      144
Glu Ala Leu Thr Leu Gln Ala Lys Glu Phe Gln Met Pro Lys Ser Gln
            35                  40                  45 gag aaa gtg gcc atg                                                  159
Glu Lys Val Ala Met
50
```

<210> SEQ ID NO 20
<211> LENGTH: 53
<212> TYPE: PRT
<213> ORGANISM: artificial sequence
<220> FEATURE:
<223> OTHER INFORMATION: Synthetic peptide

<400> SEQUENCE: 20

```
Met Ile His Thr Asn Leu Lys Lys Lys Phe Ser Leu Phe Ile Leu Val
1               5                   10                  15
Phe Leu Leu Phe Ala Val Ile Cys Val Trp Lys Lys Gly Ser Asp Tyr
                20                  25                  30
Glu Ala Leu Thr Leu Gln Ala Lys Glu Phe Gln Met Pro Lys Ser Gln
            35                  40                  45
Glu Lys Val Ala Met
50
```

```
<210> SEQ ID NO 21
<211> LENGTH: 13
<212> TYPE: PRT
<213> ORGANISM: artificial sequence
<220> FEATURE:
<223> OTHER INFORMATION: synthetic peptide

<400> SEQUENCE: 21

Met Arg Leu Arg Glu Pro Leu Leu Ser Gly Ser Ala Ala
1               5                   10

<210> SEQ ID NO 22
<211> LENGTH: 30
<212> TYPE: DNA
<213> ORGANISM: artificial sequence
<220> FEATURE:
<223> OTHER INFORMATION: synthetic oligonucleotide (primer)

<400> SEQUENCE: 22
gtgacctcga ggaggtggcg agcacaaacc                                     30

<210> SEQ ID NO 23
<211> LENGTH: 34
<212> TYPE: DNA
<213> ORGANISM: artificial sequence
<220> FEATURE:
<223> OTHER INFORMATION: synthetic oligonucleotide (primer)

<400> SEQUENCE: 23
gtgacggatc cttcagctgc cgggcgctcc gata                                34

<210> SEQ ID NO 24
<211> LENGTH: 76
<212> TYPE: DNA
<213> ORGANISM: artificial sequence
<220> FEATURE:
<223> OTHER INFORMATION: synthetic oligonucleotide (primer)

<400> SEQUENCE: 24
gtcaggtcga cgaagacaac atgaggcttc gggagcctct cctcagcggc agcgccgcta    60
tgaaggagcc agccct                                                    76

<210> SEQ ID NO 25
<211> LENGTH: 36
<212> TYPE: DNA
<213> ORGANISM: artificial sequence
<220> FEATURE:
<223> OTHER INFORMATION: synthetic oligonucleotide (primer)

<400> SEQUENCE: 25
gtgacggtct cacatgacgc cacctagaag tcctga                              36

<210> SEQ ID NO 26
<211> LENGTH: 40
<212> TYPE: DNA
<213> ORGANISM: artificial sequence
<220> FEATURE:
<223> OTHER INFORMATION: synthetic oligonucleotide (primer)

<400> SEQUENCE: 26
gtgactctag aagacaacat gccggactcc accgggaact                          40

<210> SEQ ID NO 27
<211> LENGTH: 32
<212> TYPE: DNA
<213> ORGANISM: artificial sequence
```

```
<220> FEATURE:
<223> OTHER INFORMATION: synthetic oligonucleotide (primer)

<400> SEQUENCE: 27
gtgacggatc cttcagggtt tgcccacgtc ca                                    32

<210> SEQ ID NO 28
<211> LENGTH: 36
<212> TYPE: DNA
<213> ORGANISM: artificial sequence
<220> FEATURE:
<223> OTHER INFORMATION: synthetic oligonucleotide (primer)

<400> SEQUENCE: 28
gtgacgaaga caacatgcac aggaaactgg cggagc                                36

<210> SEQ ID NO 29
<211> LENGTH: 73
<212> TYPE: DNA
<213> ORGANISM: artificial sequence
<220> FEATURE:
<223> OTHER INFORMATION: synthetic oligonucleotide (primer)

<400> SEQUENCE: 29
gtgactctag aagacaacat gaggcttcgg gagccgctcc tgagcggcag cgccgcgatg      60
ccggactcca ccg                                                        73

<210> SEQ ID NO 30
<211> LENGTH: 59
<212> TYPE: PRT
<213> ORGANISM: Homo sapiens

<400> SEQUENCE: 30
```

Met Arg Leu Arg Glu Pro Leu Leu Ser Gly Ser Ala Ala Met Pro Gly
1               5                   10                  15

Ala Ser Leu Gln Arg Ala Cys Arg Leu Leu Val Ala Val Cys Ala Leu
            20                  25                  30

His Leu Gly Val Thr Leu Val Tyr Tyr Leu Ala Gly Arg Asp Leu Ser
        35                  40                  45

Arg Leu Pro Gln Leu Val Gly Val Ser Thr Pro
    50                  55

```
<210> SEQ ID NO 31
<211> LENGTH: 59
<212> TYPE: PRT
<213> ORGANISM: Mus musculus

<400> SEQUENCE: 31
```

Met Arg Phe Arg Glu Gln Phe Leu Gly Gly Ser Ala Ala Met Pro Gly
1               5                   10                  15

Ala Thr Leu Gln Arg Ala Cys Arg Leu Leu Val Ala Val Cys Ala Leu
            20                  25                  30

His Leu Gly Val Thr Leu Val Tyr Tyr Leu Ser Gly Arg Asp Leu Ser
        35                  40                  45

Arg Leu Pro Gln Leu Val Gly Val Ser Ser Thr
    50                  55

```
<210> SEQ ID NO 32
<211> LENGTH: 59
<212> TYPE: PRT
<213> ORGANISM: Bos taurus
```

-continued

<400> SEQUENCE: 32

Met Lys Phe Arg Glu Pro Leu Leu Gly Gly Ser Ala Ala Met Pro Gly
1               5                   10                  15

Ala Ser Leu Gln Arg Ala Cys Arg Leu Leu Val Ala Val Cys Ala Leu
            20                  25                  30

His Leu Gly Val Thr Leu Val Tyr Tyr Leu Ala Gly Arg Asp Leu Arg
        35                  40                  45

Arg Leu Pro Gln Leu Val Gly Val His Pro Pro
    50                  55

<210> SEQ ID NO 33
<211> LENGTH: 42
<212> TYPE: PRT
<213> ORGANISM: Gallus gallus

<400> SEQUENCE: 33

Met Lys Glu Pro Ala Leu Pro Gly Thr Ser Leu Gln Arg Ala Cys Arg
1               5                   10                  15

Leu Leu Val Ala Phe Cys Ala Leu His Leu Ser Ala Thr Leu Leu Tyr
            20                  25                  30

Tyr Leu Ala Gly Ser Ser Leu Thr Pro Pro
        35                  40

<210> SEQ ID NO 34
<211> LENGTH: 44
<212> TYPE: PRT
<213> ORGANISM: Danio rerio

<400> SEQUENCE: 34

Met Pro Asp Ser Thr Gly Asn Phe Ser Leu Leu Gln Arg Thr Cys Ser
1               5                   10                  15

Leu Val Val Leu Leu Cys Phe Leu His Ile Phe Val Thr Val Ile Tyr
            20                  25                  30

Tyr Met Arg Asn Ser Asp Ser Arg Pro Ala Phe Ala
        35                  40

<210> SEQ ID NO 35
<211> LENGTH: 55
<212> TYPE: PRT
<213> ORGANISM: Xenopus tropicalis

<400> SEQUENCE: 35

Met Lys Glu Pro Gln Leu Pro Val Ser Asn Leu Thr Ala Ala Leu Pro
1               5                   10                  15

Gly Ala Ser Leu Gln Lys Ala Cys Lys Phe Val Val Val Phe Cys Ser
            20                  25                  30

Leu His Phe Cys Val Val Leu Ile Tyr Tyr Leu Ser Gly Ala Asp Phe
        35                  40                  45

Gly Ile Leu Gln Phe Phe Arg
    50                  55

<210> SEQ ID NO 36
<211> LENGTH: 56
<212> TYPE: PRT
<213> ORGANISM: Homo sapiens

<400> SEQUENCE: 36

Leu Gln Gly Gly Ser Asn Ser Ala Ala Ile Gly Gln Ser Ser Gly
1               5                   10                  15

Glu Leu Arg Thr Gly Gly Ala Arg Pro Pro Pro Leu Gly Ala Ser
            20                  25                  30

Ser Gln Pro Arg Pro Gly Gly Asp Ser Ser Pro Val Val Asp Ser Gly
        35                  40                  45

Pro Gly Pro Ala Ser Asn Leu Thr
    50                  55

<210> SEQ ID NO 37
<211> LENGTH: 56
<212> TYPE: PRT
<213> ORGANISM: Mus musculus

<400> SEQUENCE: 37

Leu Gln Gly Gly Thr Asn Gly Ala Ala Ala Ser Lys Gln Pro Pro Gly
1               5                   10                  15

Glu Gln Arg Pro Arg Gly Ala Arg Pro Pro Pro Leu Gly Val Ser
            20                  25                  30

Pro Lys Pro Arg Pro Gly Leu Asp Ser Ser Pro Gly Ala Ala Ser Gly
        35                  40                  45

Pro Gly Leu Lys Ser Asn Leu Ser
    50                  55

<210> SEQ ID NO 38
<211> LENGTH: 60
<212> TYPE: PRT
<213> ORGANISM: Bos taurus

<400> SEQUENCE: 38

Leu Gln Gly Ser Ser His Gly Ala Ala Ala Ile Gly Gln Pro Ser Gly
1               5                   10                  15

Glu Leu Arg Leu Arg Gly Val Ala Pro Pro Pro Leu Gln Asn Ser
            20                  25                  30

Ser Lys Pro Arg Ser Arg Ala Pro Ser Asn Leu Asp Ala Tyr Ser His
        35                  40                  45

Pro Gly Pro Gly Pro Gly Pro Gly Ser Asn Leu Thr
    50                  55                  60

<210> SEQ ID NO 39
<211> LENGTH: 40
<212> TYPE: PRT
<213> ORGANISM: Gallus gallus

<400> SEQUENCE: 39

Arg Ser Pro Glu Pro Pro Arg Pro Pro Ala Asn Leu Ser
1               5                   10                  15

Leu Pro Pro Ser Arg Pro Pro Pro Pro Ala Ala Arg Pro Arg Pro
            20                  25                  30

Gly Pro Val Ser Ala Gln Pro Arg
        35                  40

<210> SEQ ID NO 40
<211> LENGTH: 34
<212> TYPE: PRT
<213> ORGANISM: Danio rerio

<400> SEQUENCE: 40

Gln Asn Gln Gln Gln Arg Pro Thr Ile His Arg Lys Leu Ala Glu Gln
1               5                   10                  15

Arg Gly Thr Thr Glu Asp Ser Arg Pro Ala Ala Asn Ala Ser Ser Asn
            20                  25                  30

<210> SEQ ID NO 41
<211> LENGTH: 34
<212> TYPE: PRT
<213> ORGANISM: Xenopus tropicalis

<400> SEQUENCE: 41

```
Gln Asn Gln Gln Ser Gln Leu Ala Tyr Lys Gln Asn Tyr Thr Ile Ser
1               5                   10                  15

Asn Ala Thr Met Arg Ala Ile Ser Thr Lys Gly Arg Thr Lys Glu Pro
            20                  25                  30

Lys Glu
```

<210> SEQ ID NO 42
<211> LENGTH: 221
<212> TYPE: PRT
<213> ORGANISM: artificial sequence
<220> FEATURE:
<223> OTHER INFORMATION: synthetic peptide

<400> SEQUENCE: 42

```
Met Pro Asp Ser Thr Gly Asn Phe Ser Leu Leu Gln Arg Thr Cys Ser
1               5                   10                  15

Leu Val Leu Leu Cys Phe Leu His Ile Phe Val Thr Val Ile Tyr
            20                  25                  30

Tyr Met Arg Asn Ser Asp Ser Arg Pro Ala Phe Ala Gln Asn Gln Gln
            35                  40                  45

Gln Arg Pro Thr Ile His Arg Lys Leu Ala Glu Gln Arg Gly Thr Thr
        50                  55                  60

Glu Asp Ser Arg Pro Ala Ala Asn Ala Ser Ser Asn Gly Gln Glu Leu
65                  70                  75                  80

Gln Ile Cys Pro Glu Glu Pro Pro Arg Leu Val Gly Pro Leu Arg Val
            85                  90                  95

Glu Phe Ser Asp Pro Ile Thr Leu Glu Met Val Arg Thr Glu Asn Ser
            100                 105                 110

Val Leu Gln Glu Gly Gly Arg Phe Arg Pro Pro Asp Cys Ile Ala Arg
        115                 120                 125

Gln Lys Val Ala Met Ile Ile Pro Phe Arg Asn Arg Asp Glu His Leu
    130                 135                 140

Lys Phe Trp Leu Tyr Tyr Leu His Pro Ile Leu Gln Arg Gln Gln Leu
145                 150                 155                 160

Asp Tyr Gly Val Tyr Val Ile Asn Gln Asp Gly Glu Asp Thr Phe Asn
            165                 170                 175

Arg Ala Lys Leu Leu Asn Ile Gly Tyr Ala Glu Ala Leu Lys Glu Tyr
            180                 185                 190

Asp Tyr Asp Cys Phe Val Phe Ser Asp Val Asp Leu Ile Pro Met Asp
        195                 200                 205

Asp Arg Asn Ile Tyr Lys Cys Tyr Asn Gln Pro Arg His
    210                 215                 220
```

<210> SEQ ID NO 43
<211> LENGTH: 214
<212> TYPE: PRT
<213> ORGANISM: artificial sequence
<220> FEATURE:
<223> OTHER INFORMATION: synthetic peptide

```
<400> SEQUENCE: 43

Met Ser Glu Ser Val Gly Phe Phe Thr Lys Ala Cys Val Val Leu Val
1               5                   10                  15

Leu Leu Cys Gly Leu His Leu Ile Val Ala Leu Ile Phe Tyr Leu Ser
                20                  25                  30

Glu Ser Pro Leu Ala Lys Phe Arg Asn Tyr Arg His Ile Ser Phe Ile
            35                  40                  45

Ser Asp Met Val Asn Ser Gln Thr His Gly Glu Leu Gly Gln Ala Asp
        50                  55                  60

Asn Glu Thr Leu Asp Val Ala Val Tyr Lys Arg Ile Tyr Asn Asn Glu
65                      70                  75                  80

Thr Val Ile Ile Gly Asp Val Glu Lys Pro Ala Glu Val Leu Glu Ser
                85                  90                  95

Cys Pro Glu Thr Ser Pro Leu Leu Val Gly Gln Leu Arg Val Glu Phe
                100                 105                 110

Ser Thr Pro Val Asp Phe Asn Leu Val Arg Gln Gly Asn Lys His Leu
            115                 120                 125

Thr Met Gly Gly Arg Tyr Thr Pro Thr Lys Cys Val Ala Leu Gln Lys
        130                 135                 140

Val Ala Met Ile Thr Pro Tyr Arg Asn Arg Glu Glu His Leu Lys Tyr
145                 150                 155                 160

Trp Leu Tyr Tyr Leu His Pro Ile Leu Lys Arg Gln Leu Leu Asp Tyr
                165                 170                 175

Gly Ile Tyr Ile Ile Glu Gln Asp Gly Glu Asn Thr Pro Asn Lys Thr
            180                 185                 190

Leu Lys Ser Leu Thr Ile Cys Ile Leu Gly Leu Ser Leu Arg Ile Ser
        195                 200                 205

Val Thr Leu Met Val Glu
        210
```